United States Patent
Creech et al.

(10) Patent No.: US 12,018,097 B2
(45) Date of Patent: Jun. 25, 2024

(54) NON-CHROMATOGRAPHIC PURIFICATION OF MACROCYCLIC PEPTIDES BY A RESIN CATCH AND RELEASE

(71) Applicant: BRISTOL-MYERS SQUIBB COMPANY, Princeton, NJ (US)

(72) Inventors: Gardner S. Creech, North Holland (NL); Mahboubeh Kheirabadi, Cambridge, MA (US); Martin D. Eastgate, Titusville, NJ (US); David S. Nirschl, Yardley, PA (US); Percy H Carter, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 17/943,532

(22) Filed: Sep. 13, 2022

(65) Prior Publication Data

US 2024/0051996 A1    Feb. 15, 2024

Related U.S. Application Data

(62) Division of application No. 16/618,847, filed as application No. PCT/US2018/036614 on Jun. 8, 2018, now Pat. No. 11,479,581.

(60) Provisional application No. 62/517,731, filed on Jun. 9, 2017.

(51) Int. Cl.
| | |
|---|---|
| C07C 309/73 | (2006.01) |
| C07C 309/07 | (2006.01) |
| C07C 309/75 | (2006.01) |
| C07C 309/77 | (2006.01) |
| C07D 225/02 | (2006.01) |
| C07D 225/08 | (2006.01) |
| C07K 1/04 | (2006.01) |
| C07K 1/107 | (2006.01) |
| C07K 7/64 | (2006.01) |
| C07K 17/08 | (2006.01) |

(52) U.S. Cl.
CPC ............. *C07K 7/64* (2013.01); *C07C 309/07* (2013.01); *C07C 309/73* (2013.01); *C07C 309/75* (2013.01); *C07D 225/08* (2013.01); *C07K 1/042* (2013.01); *C07K 1/1077* (2013.01); *C07K 17/08* (2013.01)

(58) Field of Classification Search
CPC ... C07C 309/73; C07C 309/77; C07D 225/02; C07D 225/08
See application file for complete search history.

(56) References Cited

U.S. PATENT DOCUMENTS

| 11,168,115 | B2 | 11/2021 | Heath et al. |
| 11,479,581 | B2 * | 10/2022 | Creech ............. C07C 317/18 |
| 2007/0027303 | A1 | 2/2007 | Rybka et al. |
| 2017/0037084 | A1 | 2/2017 | Fasan |

OTHER PUBLICATIONS

Ambaye et al., "Uptake of a Cell Permeable G7-18NATE Construct Into Cells and Binding With the Grb-7-SH2 Domain", Biopolymers—Peptide Science, 2011, 96, 181-188.
Aucagne, V. et al., Towards the Simplification of Protein Synthesis: Iterative Sol id-Supported Ligations with Concomitant Purifications. Angewandte Chemie-InternationalEdition 2012, 51, 11320-11324.
B. Plapp. Mechanisms of Carboxymethylation of Bovine Pancreatic Nucleases by Haloacetates and Tosylglycolates. The Journal of Biological Chemistry. Jul. 25, 1973, vol. 248, No. 14, pp. 4896-4900. (Year: 1973).
Bashiruddin, N. K.; Suga, H. "Construction and screening of vast libraries of natural product-like macrocyclic peptides using in vitro display technologies." Curr. Opin. Chem. Biol. 2015, 24, 131-138.
Bijukumar, G. et al., Efficient Synthesis of Sivelestat Sodium Hydrate, Synth. Commun. 2008, 38, 1718-1724.
Biron, E. et al., Improving oral bioavailability of peptides by multiple N-methylation: Somatostatin analogues. Angewandte Chemie-InternationalEdition 2008, 47, 2595-2599.
Borel, J. F. et al., Biological Effects of Cyclosporin-A—New Antilymphocytic Agent. Agents Actions 1976, 6, 468-475.
Chatterjee, J. et al., NMethylation of Peptides: A New Perspective in Medicinal Chemistry. Accounts Chem. Res. 2008, 41, 1331-1342.
Frey, A. et al., Immunization of mice with peptomers covalently coupled to aluminum oxide nanoparticles. Vaccine 1999, 17, 3007-3019.
Golkowski et al. Strategy for catch and release of azide-tagged biomolecules utilizing a photolabile strained alkyne construct. Organic & Biomolecular Chemistry. 2012, vol. 10, pp. 4496-4499. (Year: 2012).
Gunasekera et al. "Chemical Synthesis and Biosynthesis of the Cyclotide Family of Circular Proteins," IUBMB Life, Jan. 3, 2008 (Jan. 3, 2008), vol. 58, Iss. 9, pp. 515-524.
Hayashi, Y. et al. In Vitro Selection of Anti-Akt2 Thioether-Macrocyclic Peptides Leading to Isoform-Selective Inhibitors. ACS Chem. Biol. 2012, 7, 607-613.

(Continued)

*Primary Examiner* — Jeffrey E. Russel
(74) *Attorney, Agent, or Firm* — BakerHostetler

(57) ABSTRACT

The disclosure is directed to the synthesis and improved methods for purifying macrocyclic peptides produced by solid phase peptide synthesis. The synthesized peptide is capped with an alkyne-functionalized or azide-functionalized compound of formula (I):

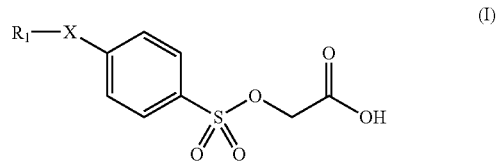

prior to cleavage of the peptide from the solid phase support.

2 Claims, 3 Drawing Sheets

Specification includes a Sequence Listing.

(56) References Cited

OTHER PUBLICATIONS

Hill, T. A. et al., Constraining Cyclic Peptides to Mimic Protein Structure Motifs. Angewandte Chemie-International Edition 2014, 53, 13020-13041.

Ito, K. et al., Technologies for the Synthesis of mRNA-Encoding Libraries and Discovery of Bioactive Natural Product-Inspired Non-Traditional Macrocyclic Peptides. Molecules 2013, 18, 3502-3528.

Iwasaki, K. et al. A Fluorescent Imaging Probe Based on a Macrocyclic Scaffold That Binds to Cellular EpCAM. J. Mol. Evol. 2015, 81, 210-217.

Kheirabadi et al. "Leveraging a "Catch-Release" Logic Gate Process for the Synthesis and Nonchromatographic Purification of Thioether- or Amine-Bridged Macrocyclic Peptides," The Journal of Organic Chemistry, Mar. 14, 2018 (Mar. 14, 2018), vol. 83, No. 8, pp. 4323-4335.

Kodan, A. et al:, Structural basis for gating mechanisms of a eukaryotic P-glycoprotein homolog. Proceedings of the National Academy of Sciences of the United States of America 2014, 111, 4049-4054.

Kotz, J. Macrocycles by the trillions, SciBX (Science-Business exchange), 2010, reprint from 2012, 3 pages.

McGeary, An 'inside-out' approach to suramin analogues, Tetrahedron. May 16, 2009;65(20):3990-3997.

Morimoto, J. et al. Discovery of Macrocyclic Peptides Armed with a Mechanism-Based Warhead: Isoform—Selective Inhibition of Human Deacetylase SIRT2. Angew. Chem.—Int. Edit. 2012, 51, 3423-3427.

Nessen, M. et al., Selective Enrichment of Azide-Containing Peptides from Complex Mixtures. Journal of Proteome Research 2009, 8, 3702-3711.

Osapay, et al., Lanthionine-somatostatin analogs: Synthesis, characterization, biological activity, and enzymatic stability studies. J. Med. Chem. 1997, 40, 2241-2251.

Rezai, T. et al. Conformational flexibility, internal hydrogen bonding, and passive membrane permeability: Successful in silico prediction of the relative permeabilities of cyclic peptides. J. Am. Chem. Soc. 2006, 128, 14073-14080.

Roberts, K. D. et al., Efficient synthesis of thioether-based cyclic peptide libraries. Tetrahedron Lett. 1998, 39, 8357-8360.

Robey, F. A. et al. Automated Synthesis of N-bromoacetyl-modified peptides for the preparation of synthetic peptide polymers, peptide protein conjugates, and cyclic-peptides. Anal. Biochem. 1989, 177, 373-377.

Schreiber, S. L.; Crabtree, G. R. The mechanism of action of cyclosporin A and FK506. Immun. Today 1992, 13, 136-142.

Tanaka, Y. et al. Structural basis for the drug extrusion mechanism by a MATE multi drug transporter. Nature 2013, 496, 247.

Teixido, M. el al., Solid-phase synthesis and characterization of N-methy 1-rich peptides. J. Pept. Res. 2005, 65, 153-166.

Turner et al. Click Chemistry as a Macrocyclization Tool in the Solid-Phase Synthesis of Small Cyclic Peptides. Organic Letters. 2007, vol. 9, No. 24, pp. 5011-5014. (Year: 2007).

Urban, J. et al. Lability of N-alkylated peptides towards TFA cleavage. Ini. J. Pept. Protein Res. 1996, 47, 182-189.

Valverde et al. "Multiple, successive azide-alkyne cycloadditions as a new ligation tool," Journal of Peptide Science, Oct. 7, 2008 (Oct. 7, 2008), vol. 14, Iss. S1, pp. 90-91.

Verdine, G. L. et al. The challenge of drugging undruggable targets in cancer: lessons learned from targeting BCL-2 family members. Clin. Cancer Res. 2007, 73, 7264-7270.

Wang, C. K. et al., Rational design and synthesis of an orally bioavailable peptide guided by NMR amide temperature coefficients. Proc. Natl. Acad. Sci. U. S. A. 2014, 111, 17504-17509.

White, T. R. et al., On-resin Nmethylation of cyclic peptides for discovery of orally bioavailable scaffolds. Nat. Chem. Biol. 2011, 7, 810-817.

Yamagata, K. et al. Structural Basis for Potent Inhibition of SIRT2 Deacetylase by a Macrocyclic Peptide Inducing Dynamic Structural Change. Structure 2014, 22, 345-352).

Yamagishi, Y. et al., Natural Product-Like Macrocyclic N-Methyl-Peptide Inhibitors against a Ubiquitin Ligase Uncovered from a Ribosome-Expressed De Novo Library. Chemistry & Biology 2011, 18, 1562-1570.

Yudin, A. K. "Macrocycles: lessons from the distant past, recent developments, and future directions." Chem. Sci. 2015, <5, 30-49.

Zhang, M. C. et al., Purification of Synthetic Peptides Using a Catching Full-Length Sequence by Polymerization Approach. Org. Lett. 2014, 16, 1290-1293.

\* cited by examiner

NON-CHROMATOGRAPHIC PURIFICATION OF MACROCYCLIC PEPTIDES BY A RESIN CATCH AND RELEASE

CROSS-REFERENCE TO RELATED APPLICATION

This application is a divisional of U.S. application Ser. No. 16/618,847, filed Dec. 3, 2019, which claims the priority of International Application No. PCT/US2018/036614, filed Jun. 8, 2018, which claims the benefit of U.S. Provisional Patent Application No. 62/517,731, filed on Jun. 9, 2017, the entirety of which are incorporated by reference herein.

SEQUENCE LISTING

The instant application contains a Sequence Listing XML, which is being submitted electronically in XML format and is hereby incorporated by reference in its entirety. Said XML copy, created on Oct. 5, 2023, is named 082867000372_Sequence_Listing.xml and is 183,838 bytes in size.

TECHNICAL FIELD

The disclosure is directed to the synthesis and improved methods for purifying macrocyclic peptides produced by solid phase peptide synthesis.

BACKGROUND

Macrocyclic peptides represent an attractive molecular paradigm for expanding the diversity of chemical matter capable of treating human disease. See Yudin, A. K. "Macrocycles: lessons from the distant past, recent developments, and future directions." *Chem. Sci.* 2015, 6, 30-49. Many potential therapies target protein-protein interactions, which have historically been perceived as "undruggable" due to the lack of success applying traditional small molecule approaches to these interactions. See Verdine, G. L. et al. The challenge of drugging undruggable targets in cancer: lessons learned from targeting BCL-2 family members. *Clin. Cancer Res.* 2007, 13, 7264-7270. In contrast to small molecule therapeutics, macrocyclic peptides possess a larger surface area, greater conformational flexibility and expanded chemical diversity, offering many potential weak binding sites to interact with the extended protein surface, interactions that can cumulatively lead to tight and highly specific binding. Thus, macrocyclic peptides are viewed as a potentially promising chemical modality to treat disease. See Hill, T. A. et al., Constraining Cyclic Peptides To Mimic Protein Structure Motifs. *Angewandte Chemie International Edition* 2014, 53, 13020-13041. Several cell permeable and orally bioavailable macrocyclic peptides have been developed by judicious use of modifications such as backbone N-methylation. See Chatterjee, J. et al., N-Methylation of Peptides: A New Perspective in Medicinal Chemistry. *Accounts Chem. Res.* 2008, 41, 1331-1342; see also Rezai, T. et al. Conformational flexibility, internal hydrogen bonding, and passive membrane permeability: Successful in silico prediction of the relative permeabilities of cyclic peptides. *J. Am. Chem. Soc.* 2006, 128, 14073-14080; Biron, E. et al., Improving oral bioavailability of peptides by multiple N-methylation: Somatostatin analogues. *Angewandte Chemie-International Edition* 2008, 47, 2595-2599; White, T. R. et al., On-resin N-methylation of cyclic peptides for discovery of orally bioavailable scaffolds. *Nat. Chem. Biol.* 2011, 7, 810-817; Wang, C. K. et al., Rational design and synthesis of an orally bioavailable peptide guided by NMR amide temperature coefficients. *Proc. Natl. Acad. Sci. U.S.A* 2014, 111, 17504-17509. One example in which these effects have been very well studied is cyclosporin A, a marketed immunosuppressive compound administered orally to prevent rejection in organ transplantation. See Borel, J. F. et al., Biological Effects Of Cyclosporin-A—New Antilymphocytic Agent. *Agents Actions* 1976, 6, 468-475; see also Schreiber, S. L.; Crabtree, G. R. The mechanism of action of cyclosporin A and FK506. *Immun. Today* 1992, 13, 136-142.

As a discovery platform, utilizing a nucleophilic cysteine displacement as a peptide macrocyclization motif is one of the most attractive ways for constructing and screening peptides. Bashiruddin, N. K.; Suga, H. "Construction and screening of vast libraries of natural product-like macrocyclic peptides using in vitro display technologies." *Curr. Opin. Chem. Biol.* 2015, 24, 131-138; Kotz, J. Macrocycles by the trillions. *SciBX* 2012, 5. Thioether peptide macrocycles, as a class of compounds, were shown to be non-immunogenic (see Frey, A. et al., Immunization of mice with peptomers covalently coupled to aluminum oxide nanoparticles. *Vaccine* 1999, 17, 3007-3019) with improved redox stability inside cells, as compared to disulfide macrocycles. See Osapay, et al., Lanthionine-somatostatin analogs: Synthesis, characterization, biological activity, and enzymatic stability studies. *J. Med. Chem.* 1997, 40, 2241-2251. This approach is highly amenable to library-based approaches when coupled to mRNA display technology via genetic code reprogramming with nonproteinogenic amino acids. See Ito, K. et al., Technologies for the Synthesis of mRNA-Encoding Libraries and Discovery of Bioactive Natural Product-Inspired Non-Traditional Macrocyclic Peptides. *Molecules* 2013, 18, 3502-3528. The thioether macrocycle forms spontaneously at pH>7.5 through chemoselective nucleophilic displacement of an N-terminal chloro- or bromoacetyl "cap", installed via translation with an N-haloacetyl amino acid initiator, by a downstream cysteine. See Roberts, K. D. et al., Efficient synthesis of thioether-based cyclic peptide libraries. *Tetrahedron Lett.* 1998, 39, 8357-8360; see also Robey, F. A. et al. Automated Synthesis of N-bromoacetyl-modified peptides for the preparation of synthetic peptide polymers, peptide protein conjugates, and cyclic-peptides. *Anal. Biochem.* 1989, 177, 373-377. Utilizing this technology, several backbone thioether macrocyclic peptides such as $CM_{11}$-1 (Yamagishi, Y. et al., Natural Product-Like Macrocyclic N-Methyl-Peptide Inhibitors against a Ubiquitin Ligase Uncovered from a Ribosome-Expressed De Novo Library. *Chemistry & Biology* 2011, 18, 1562-1570), Pakti-L1 (Hayashi, Y. et al. In Vitro Selection of Anti-Akt2 Thioether-Macrocyclic Peptides Leading to Isoform-Selective Inhibitors. *ACS Chem. Biol.* 2012, 7, 607-613), Epi-1 (Iwasaki, K. et al. A Fluorescent Imaging Probe Based on a Macrocyclic Scaffold That Binds to Cellular EpCAM. *J. Mol. Evol.* 2015, 81, 210-217), aCAP (Bashiruddin, N. K. et al. Construction and screening of vast libraries of natural product-like macrocyclic peptides using in vitro display technologies. *Curr. Opin. Chem. Biol.* 2015, 24, 131-138; Kodan, A. et al.; Structural basis for gating mechanisms of a eukaryotic P-glycoprotein homolog. *Proceedings of the National Academy of Sciences of the United States of America* 2014, 111, 4049-4054), S2iL5 (Morimoto, J. et al. Discovery of Macrocyclic Peptides Armed with a Mechanism-Based Warhead: Isoform-Selective Inhibition of Human Deacetylase SIRT2. *Angew. Chem.-Int. Edit.* 2012, 51, 3423-3427; Yamagata, K. et al. Structural Basis for Potent Inhibition of SIRT2 Deacetylase by a Macrocyclic Peptide Inducing Dynamic Structural Change. *Structure* 2014, 22, 345-352), MaL6 (Tanaka, Y. et al. Structural basis for the drug extrusion mechanism by a MATE multidrug transporter. *Nature* 2013, 496, 247), have been identified by selection against protein targets of interest, demonstrating the power of this platform for lead discovery. These results have made thioether macrocycles one of the lead chemotypes in this exciting new field.

Solid phase peptide synthesis (SPPS) is a key enabling technology to this new field. It provides a powerful tool for peptide synthesis and lead optimization of the thioether macrocyclic peptide hits generated by mRNA encoding libraries. However, while production on solid phase is facile, the crude peptide sequences often require significant purification, which places a substantial burden on purification platforms, which is frequently the rate-limiting step in the drug discovery process of peptide libraries. Additionally, peptides obtained from Fmoc-SPPS are often accompanied by several impurities traced back to each failed iterative step of the synthesis (denoted as failure sequences). While several potential mechanisms of impurity formation such as epimerization, insertion of additional amino acids, sequence deletions, aspartimide formation, sequential piperidine adduct formations, and degradation during resin cleavage can be minimized by judicious choice of SPPS conditions, it still remains that the generation of impurities is unavoidable. In particular, while the presence of backbone N-alkylation may imbue desirable pharmacokinetic/pharmacodynamics properties, their presence exacerbates impurity formation via two mechanisms: 1) each site of N-alkylation in the backbone involves coupling onto a secondary amine, increasing the likelihood of deletion/truncation products (see Teixido, M. et al., Solid-phase synthesis and characterization of N-methyl-rich peptides. *J. Pept. Res.* 2005, 65, 153-166), and 2) backbone N-alkylation has been shown to lead to hydrolysis of the adjacent peptide bond during global acidic deprotection. See Urban, J. et al. Lability of N-alkylated peptides towards TFA cleavage. *Int. J. Pept. Protein Res.* 1996, 47, 182-189. Accumulation of the aforementioned impurities, tert-butylation of free cysteine during global cleavage, and the side products generated during cyclization, place a necessary burden on chromatographic purification in high-throughput drug discovery—where two stage purification is often needed to obtain purities required for screening.

Others have demonstrated the concept of "solid-phase assisted purification" to enrich a desired linear peptide sequence for proceeding single pass purifications. See Nessen, M. et al., Selective Enrichment of Azide-Containing Peptides from Complex Mixtures. *Journal of Proteome Research* 2009, 8, 3702-3711; Aucagne, V. et al., Towards the Simplification of Protein Synthesis: Iterative Solid-Supported Ligations with Concomitant Purifications. *Angewandte Chemie-International Edition* 2012, 51, 11320-11324; Zhang, M. C. et al., Purification of Synthetic Peptides Using a Catching Full-Length Sequence by Polymerization *Approach. Org. Lett.* 2014, 16, 1290-1293. In addition to specific limitations of each approach, such as modification of the final peptide with cyclooctyne and linker, low recoveries, and limitation to linear peptides, they all have the commonality of removing only the truncated failure sequences.

Thus, there is a need for solid-phase assisted purification methods that are capable of handling the breadth of impurities that are observed in practice, that are compatible with peptide macrocycles, and that can be adapted to a high-throughput setting.

SUMMARY

The disclosure is directed to compounds and methods for preparing purified macrocyclic peptide using "catch-release" methods. These methods comprise (a) preparing a resin-bound linear peptide wherein said linear peptide comprises a free amino group and an amino acid residue having a nucleophilic side chain; (b) reacting the free amino group of the resin-bound linear peptide with an azide- or alkyne-functionalized cap to form a resin-bound capped linear peptide having an azide- or alkyne-functionalized cap; (c) cleaving said capped linear peptide from the resin to form a free capped linear peptide having an azide- or alkyne-functionalized cap; (d) reacting the free capped linear peptide having an azide-functionalized cap with an alkyne-functionalized catch resin, or reacting the free capped linear peptide having an akynyl-functionalized cap with an azide functionalized catch resin, to form a catch-resin bound capped linear peptide; (e) washing the catch-resin bound capped linear peptide to remove impurities; (f) reacting the catch-resin bound capped linear peptide under conditions sufficient to effect macrocyclization of the linear peptide and release of the macrocyclic peptide from the catch resin, wherein the macrocyclization and release results from reaction of the nucleophilic side chain of the amino acid residue in the linear peptide with an electrophilic leaving group moiety on the cap.

DETAILED DESCRIPTION OF ILLUSTRATIVE EMBODIMENTS

Figure 1:
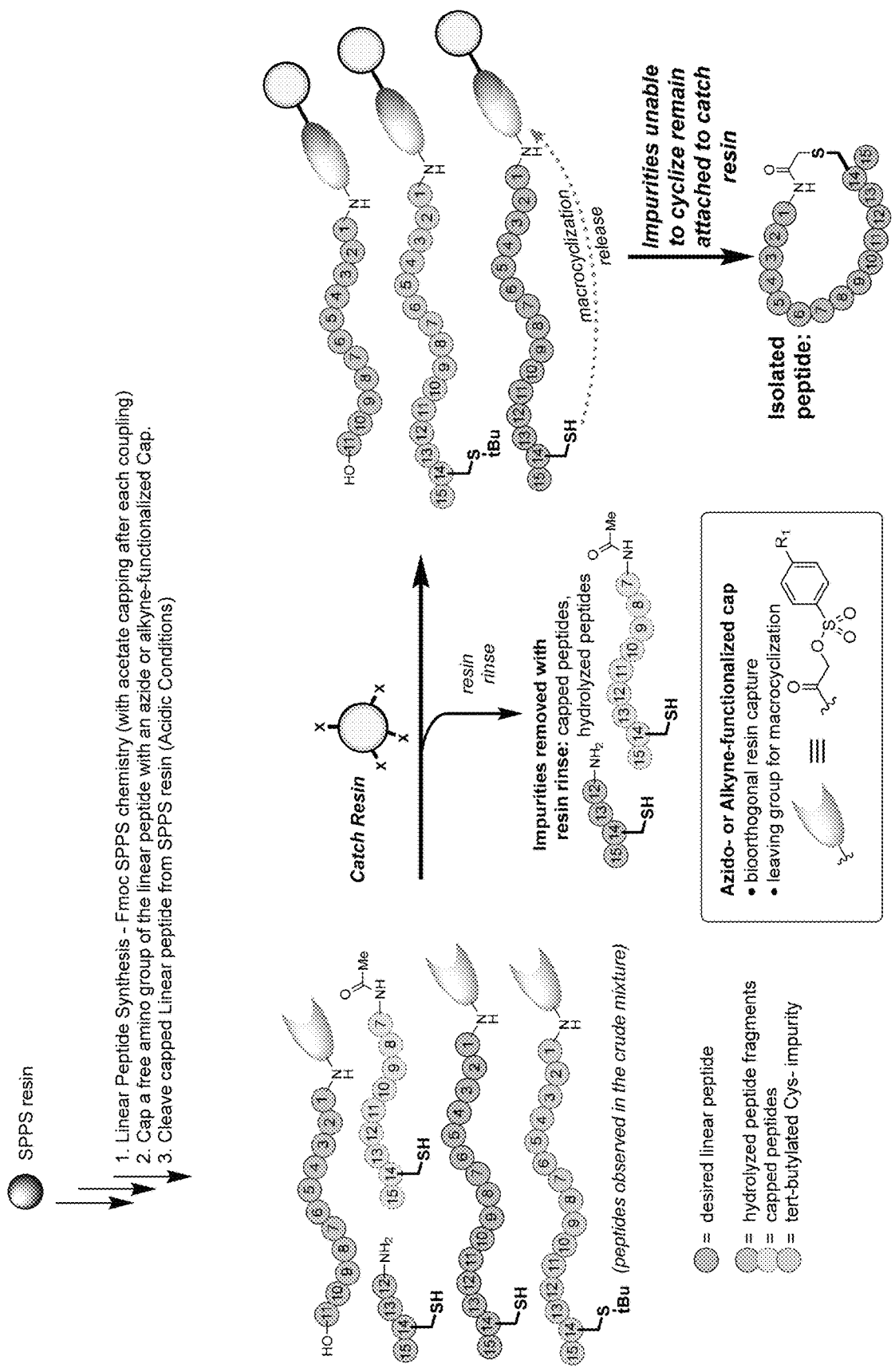
FIG. 1 shows a schematic illustration of a general catch-release purification method.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, when a range is given for the number of units that may be present in a group, the range is to be understood to representing the specified range, and all possible constituent subranges. For example, the range "n is 1-6" as used herein means that n is 1-6, 1-5, 1-4, 1-3, 1-2, 1, 2, 3, 4, 5, or 6.

The term "aryl" when used alone or as part of a substituent group refers to a mono- or bicyclic-aromatic hydrocarbon ring structure having 6 or 10 carbon atoms in the ring, wherein one or more of the carbon atoms in the ring is optionally substituted. The term "arylene" refers to an aryl diradical that is part of a substituent group. Preferred aryl groups include phenyl and napthalenyl.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_1$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like.

The term "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "$C_1$-$C_{12}$alk" when used alone or as part of a substituent group refers to an aliphatic linker having 1, 2, 3, 4, 5, 6, 7, 8, 9, 10, 11, or 12 carbon atoms and includes, for example, —$CH_2$—, —$CH(CH_3)$—, —$CH(CH_3)$—$CH_2$—, and —$C(CH_3)_2$—. In some aspects, the $C_1$-$C_6$alk or $C_1$-$C_{12}$alk can be substituted with one or more substituents.

In some aspects, the disclosure is directed to a catch-release method of preparing a purified macrocyclic peptide. The term "catch-release" describes the concept underlying the disclosed purification methods: "catching" a linear peptide on a catch resin, and macrocyclizing and "releasing," preferably in a simultaneous fashion, the macrocyclic peptide from the catch resin. In these methods, the macrocyclization reaction can be simultaneous with the release because the reaction that macrocyclizes the peptide, also effects release of the macrocyclic peptide from the catch resin.

Figure 2:
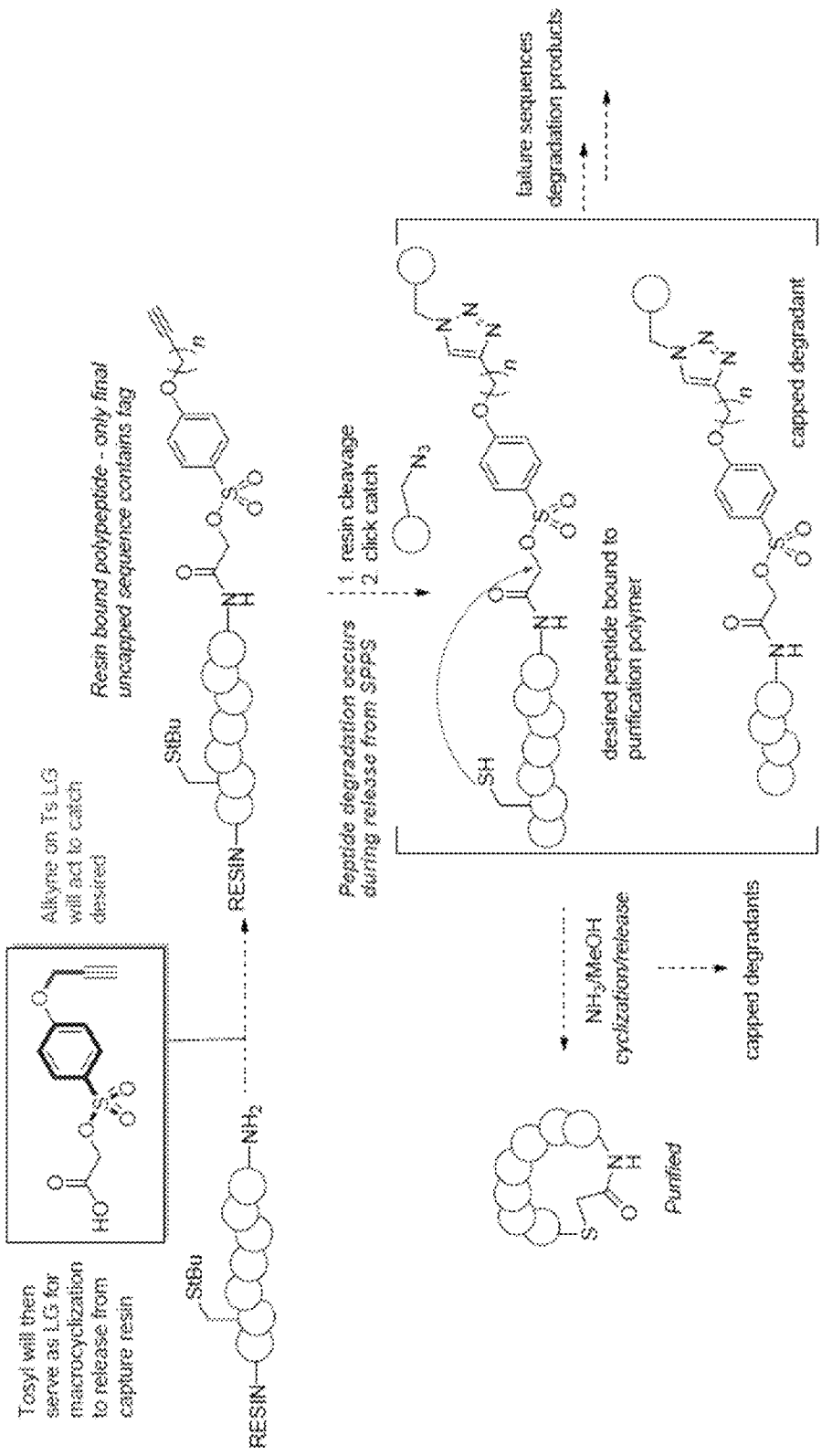
FIG. 2 shows a schematic illustration of a catch-release purification method using a specific alkyne-functionalized cap.

FIGS. 1 and 2 illustrate the basic concept underlying the catch-release method. As shown in FIG. 1, solid phase peptide synthesis (SPPS) is used to prepare a linear peptide. The N-terminus of the linear peptide is then capped with a tosyl hydroxyl acetate moiety. The capped linear peptide is then cleaved from the SPPS resin by acid. The linear peptide, along with impurities, are reacted with a catch resin (represented by the gray circle in FIG. 1). In the macrocyclization release step, a thiol group on a side chain of the linear peptide undergoes intramolecular nucleophilic displacement of the tosyl portion of the cap, resulting in simultaneous macrocyclization and release of the peptide. Purification results because only the macrocyclized peptide is released. Other peptides unable to undergo the macrocyclization are not released, and therefore remain bound to the catch resin and are removed by physical separation of the catch resin and the macrocyclic peptide.

FIG. 2 illustrates the catch-release concept of the present disclosure in the context of a specific functionalized cap. The alkyne functionalized cap is reacted with an amino group on the resin-bound linear peptide to form a resin-bound capped linear peptide. The capped linear peptide is cleaved from the resin, and then reacted with an azide functionalized catch resin. The azido group of the catch resin reacts with the alkynyl group of the cap to form a triazole ring, and thereby covalently link the catch resin and the linear peptide. In the macrocyclization and release step, a thiol group on the linear peptide nucleophilically displaces the tosyl portion of the cap, resulting in simultaneous macrocyclization and release of the peptide. As in FIG. 1, purification results because only the macrocyclized peptide is release. Other peptides unable to undergo the macrocyclization are not released, and therefore remain bound to the catch resin and are removed by physical separation of the catch resin and the macrocyclic peptide.

The catch-release method of the present disclosure comprises as a first step, designated as (a), preparing a resin-bound linear peptide wherein the linear peptide comprises a free amino group and an amino acid having a nucleophilic side chain. In principle, the resin used in this step may be any resin that is suitable for solid phase peptide synthesis ("SPPS"). Such resins are known to those of skill in the art, and include, for example, Wang resin, PHB resin, HMPA resin, HMPB resins, 2-chlorotrityl resins, 4-carboxytrityl resins, Rink acid resin, Rink amide resin, PAL resin, Sieber amide resin, FMP resin, Merrifield resin, PAM resin, BHA resin, MBHA resin, and brominated Wang resin. Preferred resins are those from which the capped linear peptide may be cleaved with minimal degradation. Particularly preferred resins are those from which the capped linear peptide may be cleaved under acid conditions.

Conditions for preparing resin bound linear peptides will be known by those of skill in the art, and include use of, for example, standard Fmoc chemistry using 1-[Bis(dimethylamino)methylene]-1H-1,2,3-triazolo[4,5-b]pyridinium 3-oxide hexafluorophosphate ("HATU")/N-methylmorpholine ("NMM") systems on an automated peptide synthesizer.

In the methods of the present disclosure, the resin-bound linear peptide may have from 3-25, preferably 5-25, amino acid residues. For example, the resin-bound linear peptide may have 3, 4, 5, 6, 7, 8, 9, 10, 11, 12, 13, 14, 15, 16, 17, 18, 19, 20, 21, 22, 23, 24, or 25 amino acid residues. In some embodiments, the resin-bound linear peptide has more than 25 amino acid residues, for example, 26-50, 51-75, or 76-100 amino acid residues. The amino acids that comprise the linear peptide may be naturally occurring amino acids, or non-naturally occurring amino acids of any stereochemical configuration. Examples of linear peptides include those having the amino acid sequences listed below in Tables 1, 4, and 5. Methods of synthesizing resin-bound linear peptides are known by those of skill in the art.

In the present disclosure, the resin bound linear peptides in step (a) comprise a free amino group. The free amino group may be the free —$NH_2$ group on the terminal amino acid of the linear peptide, or it may be a free —$NH_2$ group on a side chain of an amino acid residue of the resin-bound linear peptide.

The resin-bound linear peptides in step (a) of the present disclosure also comprise an amino acid residue having a nucleophilic side chain. In some aspects, the amino acid having a nucleophilic side chain includes those amino acids with side chains having a sulfur-containing group, an amine-containing group, or an oxygen-containing group. In other aspects, the amino acid residue having a nucleophilic side chain may be cysteine, methionine, Dap (2,3-diaminopropionic acid), lysine, Dab (diamino butyric acid), Ornithine, serine, aspartic acid, or glutamic acid. In some embodiments, the amino acid residue having a nucleophilic side chain is cysteine. In other embodiments, the amino acid having a nucleophilic side chain is Dap.

The catch-release methods of the present disclosure comprise as a second step, designated as (b), reacting the free amino group of the resin-bound linear peptide with an azide- or alkyne-functionalized cap to form a resin-bound capped linear peptide having an azide- or alkyne-functionalized cap.

In principle, the cap may be any azide or alkyne-functionalized molecule that is capable of reacting with a free amino group of the resin bound linear peptide, and is also capable of reacting with the nucleophilic side chain of the amino acid residue during the macrocyclization-release step of the methods. In some aspects, the azide- or alkyne-functionalized cap comprises a carboxylate group (—COOH) that condenses with the free amino group of the resin-bound linear peptide to form an amide bond in step (b) of the catch-release method of the present disclosure. In some aspects, the cap is an azide functionalized cap. In other aspects, the cap is an alkyne functionalized cap.

In some aspects, the cap is a compound of formula (I):

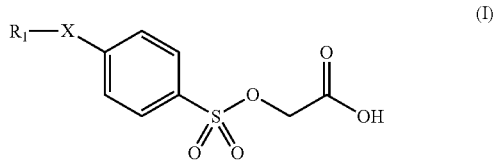

wherein
X is a bond, —O—, —C(O)—, —OC(O)—, —NH—, —N(C$_{1-6}$alkyl)-, —N(aryl)-, —NH—C(O)—, —N(C$_{1-6}$ alkyl)C(O)—, or —N(aryl)C(O)—; and
R$_1$ is

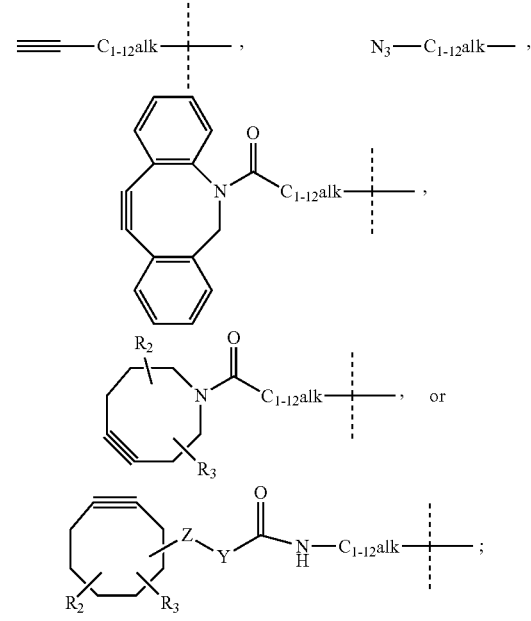

wherein R$_2$ and R$_3$ are each independently H, halo, C$_{1-6}$alkyl, or OC$_{1-6}$alkyl;
Z is C$_{1-6}$alk or —O—C$_{1-6}$alk-; and
Y is a bond or arylene.

In some embodiments, the cap is a compound of formula (I) wherein X is —O— and R$_1$ is

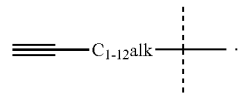

In other embodiments, the cap is a compound of formula (I) wherein X is —NH—C(O)— and R$_1$ is

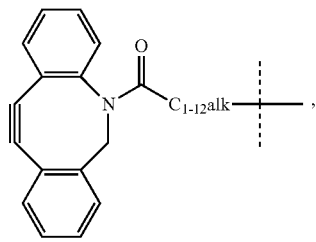

wherein R$_1$ is bonded to X through the nitrogen atom of X. In other embodiments, the cap is a compound of formula (I) wherein X is —OC(O)— and R$_1$ is wherein R$_1$ is N$_3$-C$_{1-12}$ alk-, bonded to X through the non-carbonyl oxygen atom of X. In yet other embodiments, the cap is a compound of formula (I) wherein X is —O— and R$_1$ is N$_3$-C$_{1-12}$alk-.

In some embodiments, the cap is

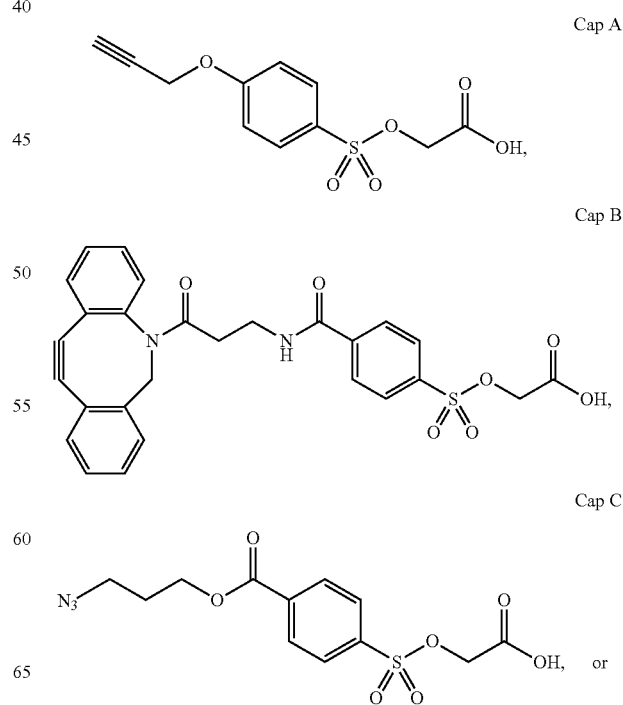

-continued

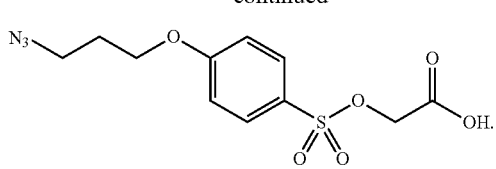
Cap D

In some embodiments, the cap is the alkyne functionalized Cap A:

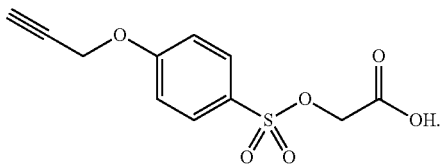
Cap A

In other embodiments, the cap is the alkyne functionalized Cap B:

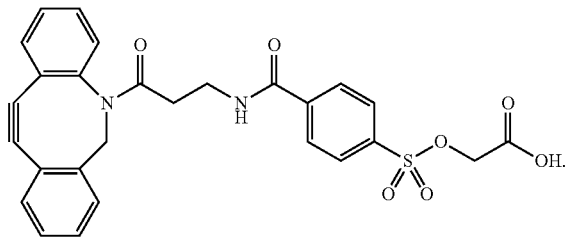
Cap B

In other embodiments, the cap is the azide functionalized Cap C:

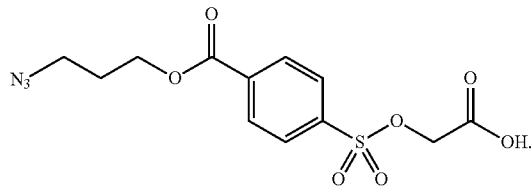
Cap C

In yet other embodiments, the cap is the azide functionalized Cap D:

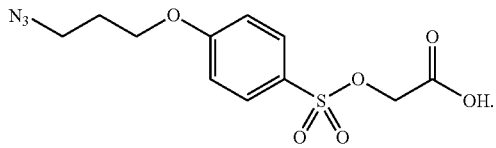
Cap D

In some embodiments of the catch-release method of the present disclosure, the carboxylate group of a Cap of formula (I) reacts with the free amino group of the resin bound linear peptide to form an amide bond, and thereby forms a resin-bound capped linear peptide having an azide- or alkyne-functionalized cap. In some embodiments, Cap A reacts with the free amino group of the resin bound linear peptide to form an amide bond, and thereby forms a resin-bound capped linear peptide having an alkyne-functionalized cap.

In other embodiments, Cap B reacts with the free amino group of the resin bound linear peptide to form an amide bond, and thereby forms a resin-bound capped linear peptide having an alkyne-functionalized cap.

In other embodiments, Cap C reacts with the free amino group of the resin bound linear peptide to form an amide bond, and thereby forms a resin-bound capped linear peptide having an azide-functionalized cap.

In yet other embodiments, Cap D reacts with the free amino group of the resin bound linear peptide to form an amide bond, and thereby forms a resin-bound capped linear peptide having an azide-functionalized cap.

Conditions capable of forming an amide bond between the carboxylate group of a Cap of formula (I) and the free amino group of the resin bound linear peptide will be known to those of skill in the art. In some aspects, the carboxylate group of a Cap of formula (I) is reacted with free amino group of the resin bound linear peptide to form an amide bond in the presence of HATU and N,N-diisopropylethylamine ("DIPEA") in N,N-dimethylformamide ("DMF") solvent.

The catch-release methods of the present disclosure comprise as a third step, designated as (c), cleaving the capped linear peptide from the resin to form a free capped linear peptide having an azide- or alkyne-functionalized cap. The conditions under which the capped linear peptide may be cleaved from the resin depend on the specific resin used, and the conditions required to cleave a peptide from a given resin will be well known by those skilled in the art. In some aspects, the capped linear peptide may be cleaved from the resin under acidic conditions. Thus, in some embodiments, the capped linear peptide is cleaved from the resin by treating the resin with acid. In some embodiments, the acid is trifluoroacetic acid ("TFA").

The catch-release methods of the present disclosure comprise as a fourth step, designated as (d), reacting the free capped linear peptide having the azide-functionalized cap (from step (c)) with an alkyne functionalized catch resin, or reacting the free capped linear peptide having the akynyl-functionalized cap (from step (c)) with an azide functionalized catch resin, to form a catch-resin bound capped linear peptide. This step is the "catch" step of the catch-release method of the present disclosure.

The "catch" step of the catch-release method of the present disclosure relies on "click chemistry" to covalently bond the free capped linear peptide to the catch resin. The term "click chemistry" generally refers to one pot reactions that couple two molecules, generate minimal and inoffensive byproducts, and are characterized by a high thermodynamic driving force that drives it quickly and irreversibly to high yield of a single reaction product, with high reaction specificity. The click chemistry of the catch step of the present method is a [3+2] cycloaddition reaction of an azido group with an alkyne to form a triazole.

In one aspect, the catch step of the catch-release methods of the present disclosure comprise reacting the free capped linear peptide having the azide-functionalized cap with an alkyne functionalized catch resin. In this aspect, the azido group of the cap reacts with the alkynyl group of the catch resin to form a triazole ring, and thereby covalently bonds the capped linear peptide to the catch resin.

In another aspect, the catch step of the catch-release method of the present disclosure comprises reacting the free capped linear peptide having the alkynyl-functionalized cap with an azido-functionalized catch resin. In this aspect, the alkynyl group of the cap reacts with the azido group of the catch resin to form a triazole ring, and thereby covalently bonds the capped linear peptide to the catch resin.

The catch resin that is used in the catch step of the catch-release methods of the present disclosure has the generic formula (II):

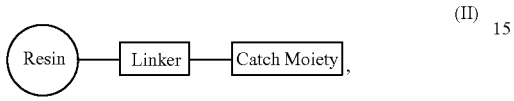
(II)

where the resin is a polyethylene glycol or polystyrene-based resin. In principle, any polyethylene glycol ("PEG")-based or polystyrene ("PS")-based resin containing functional groups for covalent attachment of other molecules (e.g., linkers) can be used to prepare a catch resin for use in the catch-release method of the present disclosure. In some aspects, the catch resin is a PEG-based resin. Suitable PEG-based resins include, for example, PEG-based Wang resin, PEG-based Rink amide resin, and PEG-based aminomethyl resin. Such resins may be used at any convenient loading, including, for example, PEG-based Wang resin (resin loading: mmol/g), PEG-based aminomethyl resin (resin loading: 0.226 mmol/g), PEG-based Rink amide resin (resin loading: 0.121 mmol/g) and PEG-based aminomethyl resin (resin loading: mmol/g). As noted above, the resin will be understood by those of skill in the art to include functional groups that are capable of forming covalent bonds with linkers of the general type used in solid phase peptide synthesis. Examples of functional groups with which the resin may be functionalized include:

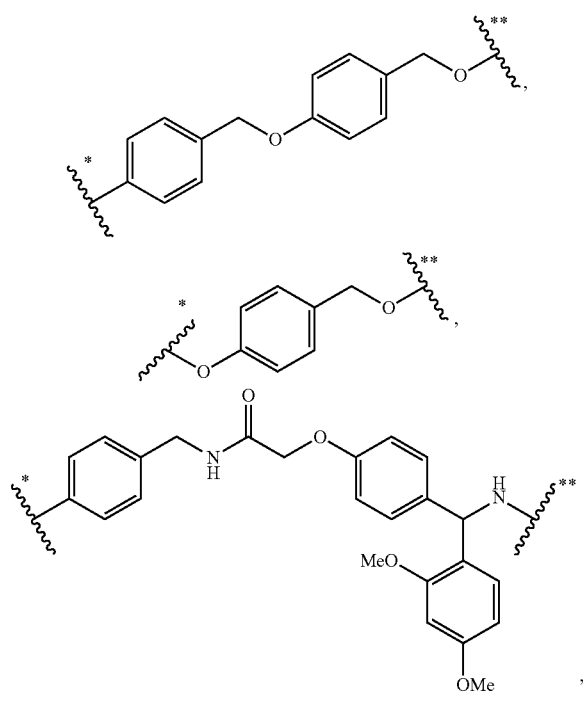

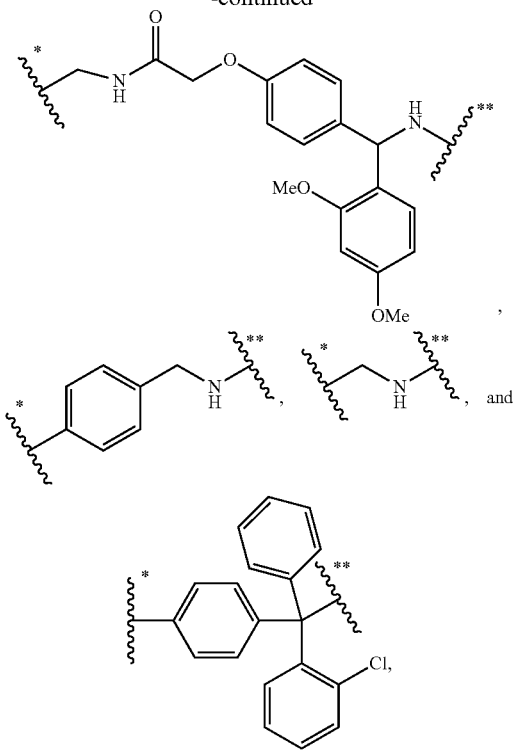

wherein $\xi^*$ denotes to the point of attachment to the resin and $\xi^{**}$ denotes to the point of attachment to a linker.

The linker in Formula II functionalizes the PEG or polystyrene resin to provide a reactive group to which a catch moiety may be attached. The linker may be any linker typically used in solid phase peptide synthesis which is also compatible with the azido or alkynyl functionalized catch moiety. Such linkers will be known by those of skill in the art. In some aspects, the linker is

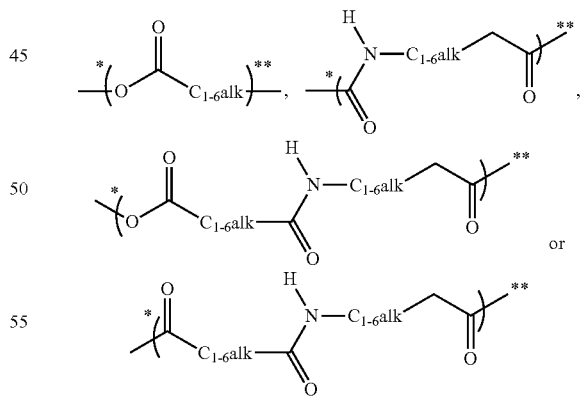

wherein *(denotes the point of attachment of the linker to the resin, and)** denotes the point of attachment of the linker to the catch moiety;

The catch moiety of the catch resin is a moiety having an alkyne or azido functional group. In some aspects, the catch moiety has an azido functional group. In other aspects, the catch moiety has an alkyne functional group. In some embodiments, the catch moiety is

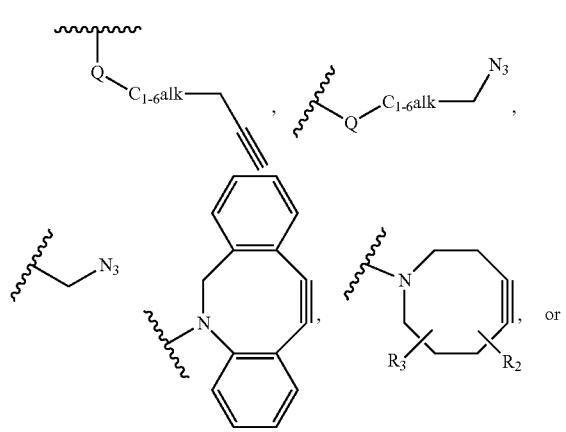
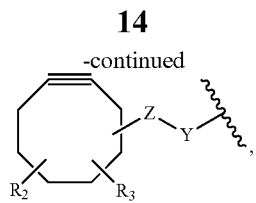
wherein Q is —O—, —NH—, or —CH₂—
R$_2$ and R$_3$ are each independently H, halo, C$_{1-6}$alkyl, or OC$_{1-6}$alkyl;
Z is C$_{1-6}$alk or —O—C$_{1-6}$alk-; and
Y is a bond or arylene.
In some embodiments, the PEG-based catch resin is
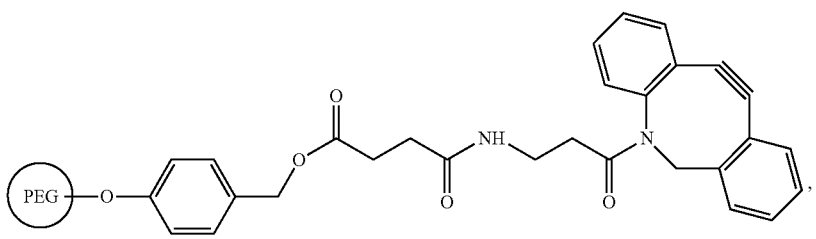
Catch Resin A
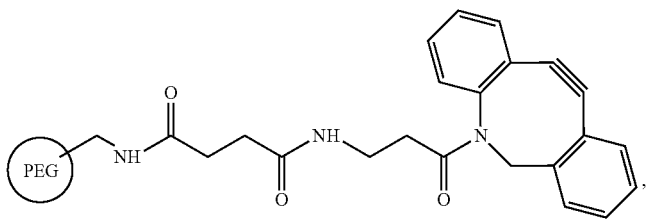
Catch Resin B
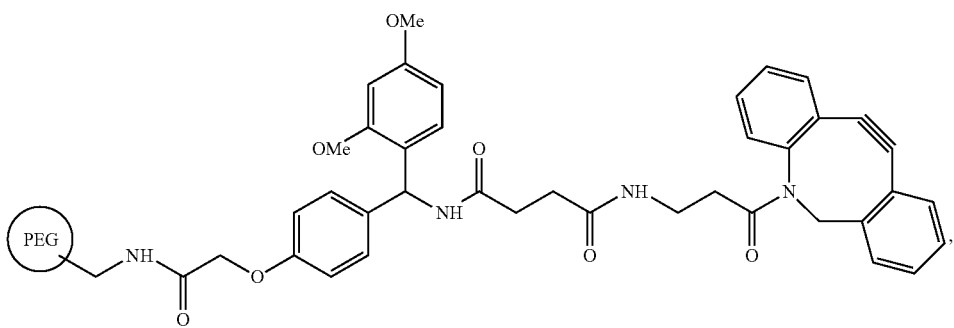
Catch Resin C
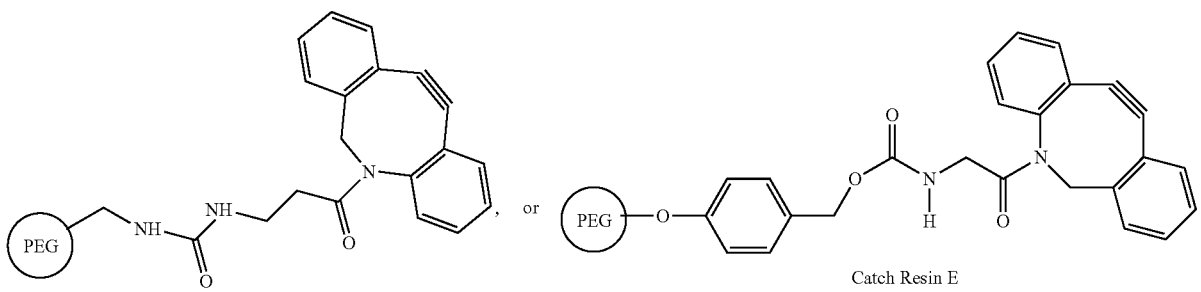
Catch Resin D                    Catch Resin E In some embodiments, therefore, the PEG-based catch resin is

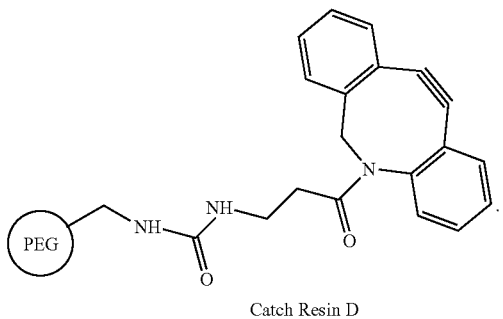 [SMILES: CCNC(=O)NCCC(=O)N1Cc2ccccc2C#Cc2ccccc21]

Catch Resin D

In other aspects, the catch resin is a PS-based resin. In some embodiments, the PS-based catch resin is

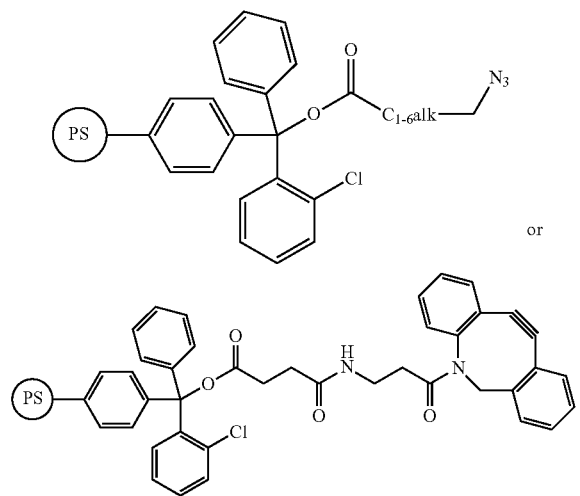

In some embodiments of the catch-release method of the present disclosure, additives may be added to the "catch" reaction to increase yield. Additives are particularly useful in cases wherein the amino acid having a nucleophilic side chain of the free capped linear peptide has a sulfur-containing moiety. In some aspects, the additives are reductants, and include 1,4-dithiothreitol ("DTT") in acetic acid ("AcOH"), sodium ascorbate in AcOH, tris(2-carboxyethyl)phosphine ("TCEP"), ascorbic acid, and $PPh_3$. A preferred additive is DTT in AcOH. Without intending to be bound by theory, these additives are believed to improve the yield of the catch-release methods of the present disclosure by preventing oxidation of thiol groups of nucleophilic amino acids.

In other embodiments of the catch-release method of the present disclosure, the "catch" step is performed in the presence of an excess of catch resin. In some embodiments about 1.1 to about 10 equivalents, preferably about 1.5 to about 7.5 equivalents, of catch resin is used in the catch step. For example, about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 equivalents of catch resin is used in the catch step. As used here, the number of equivalents refers to the moles of reactive functional group (i.e., alkyne or azide) in the catch resin versus the number of moles of reactive functional group in the cap. In preferred embodiments, the free capped linear peptide having the azido functional group is reacted with an excess of the alkyne-containing catch resin. Without intending to be bound by any particular theory, it is believed that the excess alkyne-containing catch resin increases the yield of the catch-release methods of the present disclosure by increasing the proportion of free capped linear peptide that is captured in the "catch" step.

In other embodiments, when an excess of alkyne-containing catch resin is used in the catch step, the excess alkyne group is "quenched" using a quenching agent following the catch reaction (i.e., the triazole-forming click reaction) and prior to the macrocyclization step (i.e., step (f)). The quenching agent may be, for example, any azide capable of reacting with the excess alkyne. In a preferred embodiment, the quenching agent is benzyl azide. Without intending to be bound by theory, it is believed that the use of a quenching agent to quench the excess alkyne-containing catch resin increases the yield of the catch-release methods of the present disclosure by making excess alkyne functionality unavailable for reaction with nucleophilic groups (e.g., thiol groups) of the linear peptide.

The catch-release methods of the present disclosure comprise as a fifth step, designated as step (e), washing the catch-resin bound capped linear peptide. This step can remove impurities. In some embodiments, the rinse comprises rinsing the catch resin-bound capped peptide with a solvent, preferably an organic solvent. In some embodiments, the solvent used to rinse the catch-resin-bound capped peptide is an alcoholic solvent, for example, methanol, ethanol, propanol, and the like, with methanol being particularly preferred. The impurities removed by the rinse step include hydrolyzed peptides and peptide fragments, and peptides that are not capped with an azido or alkyne-functionalized cap of the present disclosure.

The catch-release methods of the present disclosure comprise as a sixth step, designated as step (f), reacting the catch-resin bound capped linear peptide under conditions that cause macrocyclization of the linear peptide and release of the macrocyclic peptide from the catch resin. This step is referred to as the macrocyclization and "release" step. In some aspects, macrocyclization and release results from reaction of the nucleophilic side chain of the amino acid in the linear peptide with an electrophilic leaving group moiety on the cap. In some embodiments, the catch resin-bound capped peptide is treated with base, in a solvent (preferably an organic solvent), resulting in reaction between the nucleophilic side chain of and the leaving group of the cap to form a purified macrocyclic peptide. This reaction can also, preferably simultaneously, release the macrocyclic peptide from the catch resin. The macrocyclization-release step of the catch-release methods of the present disclosure removes peptides unable to undergo the macrocyclization. Such peptides are not released, and therefore remain bound to the catch resin and are removed by physical separation of the catch resin and the macrocyclic peptide. Examples of such impurities include peptides having tert-butylated Cysteine residues. See FIG. 1.

In some aspects, the macrocyclization and release step is initiated by treatment of the catch resin-bound capped linear peptide with a base, preferably an aqueous solution of the base. Exemplary bases include $NH_4OAc$, $NH_3$, DIPEA, NaOAc, HOAc, and NaOH. In some embodiments, the base used to initiate the macrocyclization and release is 0.1 M NH₄OAc-0.1 M NH₃, 0.2 M DIPEA, 0.2 M NH₄OAc, 0.2 M NaOAc, 0.2 M NH₄OAc—HOAc, or 0.1 M NaOH. In some embodiments, the base used to initiate the macrocyclization and release is 0.1 M NH₄OAc-0.1 M NH₃. The macrocyclization and release reaction may be conducted at any suitable pH, including any pH from about 6.7 to 14. In some embodiments, the macrocyclization and release reaction is conducted at pH 7, 8.0, 9.3, 9.8, 11.0, or 14.0.

In some aspects, the macrocyclization and release step is conducted in the presence of a solvent or mixture of solvents. In some embodiments, the solvent used for macrocyclization and release is methanol ("MeOH"), N,N-dimethylformamide ("DMF"), acetonitrile, dichloromethane ("DCM"), N-methyl-2-pyrrolidone, water, or mixtures of these solvents. In some aspects, the solvent is DMF-MeOH, DMF-acetonitrile, DMF-DCM, H₂O-acetonitrile, or water-MeOH. Where mixtures of solvents are used, the mixture may contain any ratio of the component solvents. When a mixture of two solvents is used, the mixture may contain a ratio of solvents from 1:1 to 1:9 (vol/vol.). In some embodiments, the solvent for the macrocyclization and release step is MeOH or aqueous MeOH. In other embodiments, the solvent for the macrocyclization and release step is DMF. In some embodiments, the solvent is 1:9 DMF-acetonitrile, 1:9 DMF-DCM, 1:9 DMF-MeOH, 1:1 H₂O-acetonitrile, or 1:1 water-MeOH.

In some embodiments, the macrocyclization and release step is conducted in 0.1 M NH₄OAc-0.1 M NH₃ in methanol.

In some aspects, the macrocyclization and release step is performed at a temperature that is at or above ambient temperature, for example, a temperature between 20° C. and 90° C. In some embodiments, the macrocyclization and release step is performed at 20-25° C. In other embodiments, the macrocyclization and release step is performed at 40-45° C. In yet other embodiments, the macrocyclization and release step is performed at 70-75° C.

Figure 3:
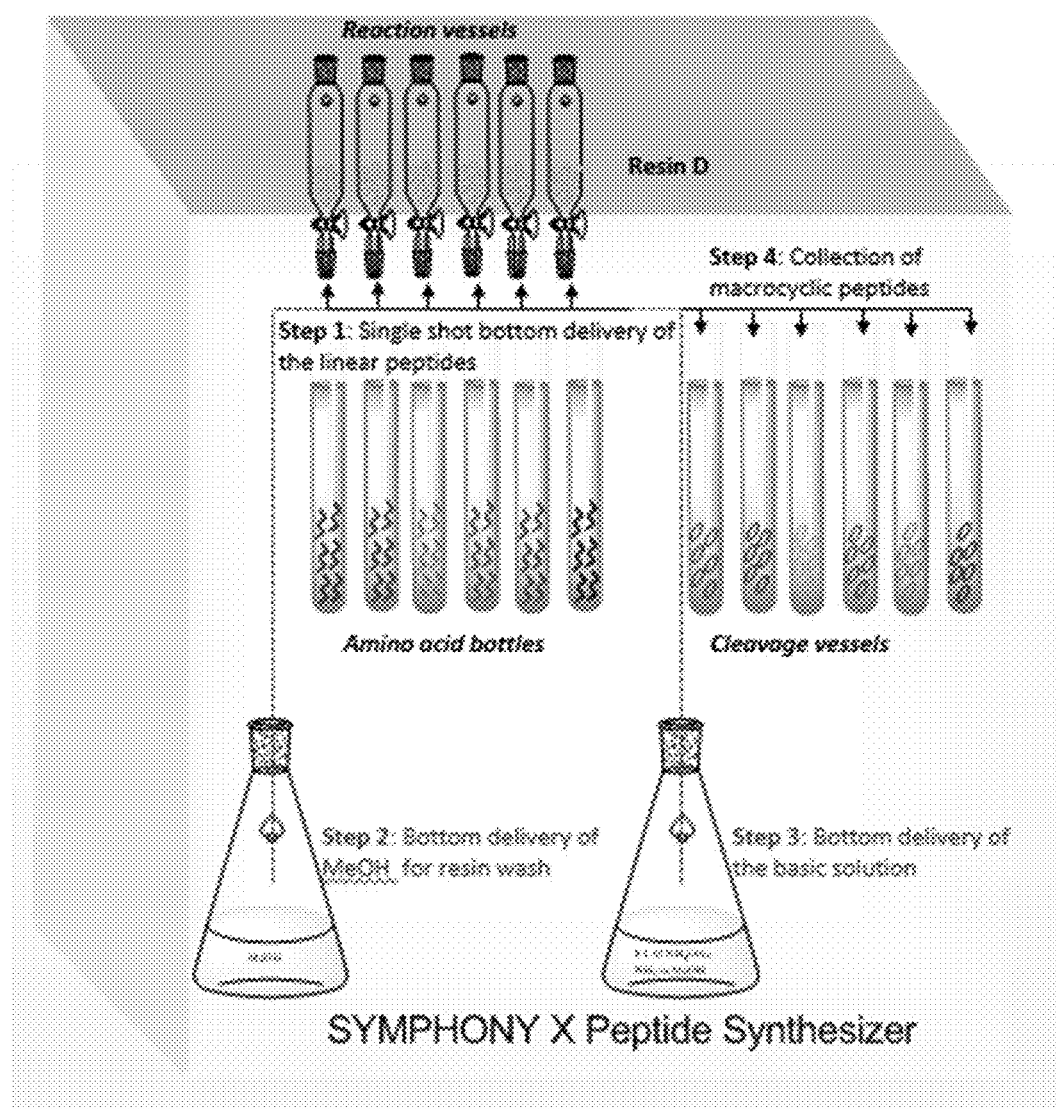
FIG. 3 shows a schematic illustration of an automated peptide synthesizer configured to perform steps of the catch-release purification method.

The present disclosure is also directed to an automated method of purification of a macrocyclic peptide. In this aspect of the invention, an instrument capable of automated peptide synthesis is outfitted to perform the catch-release purification method of the present disclosure. In some embodiments, the instrument is a multichannel peptide synthesizer. In some embodiments, the instrument is a Symphony X peptide synthesizer. Methods for automating solid phase peptide synthesis and manipulation are known in the art. FIG. 3 illustrates one method of automating the catch-release method of the present disclosure.

| Abbreviations | Full name |
|---|---|
| HATU | 1-[Bis(dimethylamino)methylene]-1H-1,2,3-triazolo[4,5-b] pyridinium 3-oxide hexafluorophosphate |
| DIC | N,N'-Diisopropylcarbodiimide |
| HOSU | N-Hydroxysuccinimide |
| DECP | Diethyl chlorophosphate |
| DIPEA | N,N-Diisopropylethylamine |
| Et₃N | Triethylamine |
| NMM | 4-Methylmorpholine |
| DMAP | 4-Dimethylaminopyridine |
| TFA | Trifluoroacetic acid |
| TFAA | Trifluoroacetic anhydride |
| TIS | Triisopropylsilane |
| DTT | 1,4-Dithiothreitol |
| BHT | 2,6-Di-tert-butyl-4-methylphenol |
| DTDP | 4,4'-Dithiodipyridine |

| Abbreviations | Full name |
|---|---|
| TCEP | Tris(2-carboxyethyl)phosphine |
| NH₄OAc | Ammonium acetate |
| AcOH | Acetic acid |
| Ac₂O | Acetic anhydride |
| NaOAc | Sodium acetate |
| DMF | N,N-Dimethylformamide |
| Et₂O | Diethyl ether |
| EtOAc | Ethyl acetate |
| DCM | Dichloromethane |
| MeOH | Methanol |
| MTBE | Methyl tert-butyl ether |
| Hex | Hexane |
| THF | Tetrahydrofuran |
| HSAB | Hard soft lewis acid and base |
| HL | High loading resin |
| LL | Low loading resin |

EXAMPLES

Synthesis of Compounds

2-{[4-(prop-2-yn-1-yloxy)benzenesulfonyl]oxy}acetic acid (Cap A)

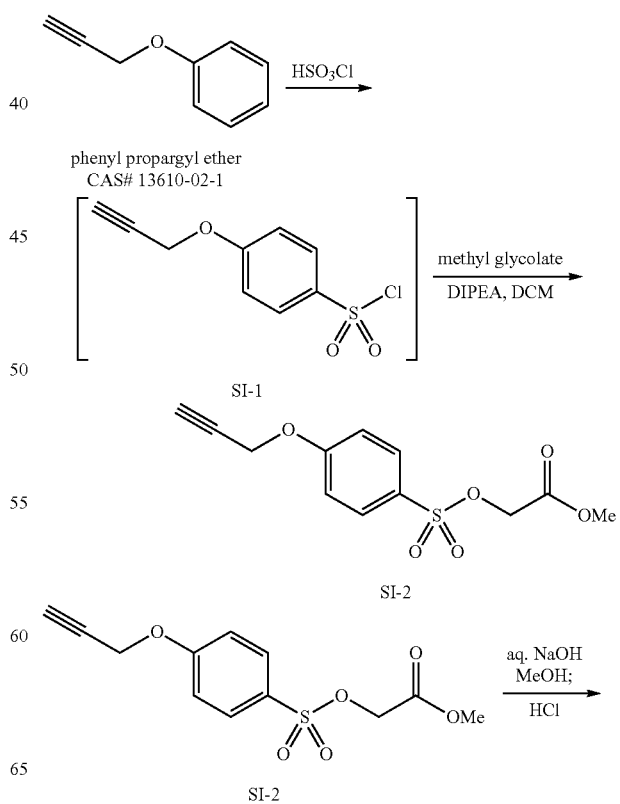

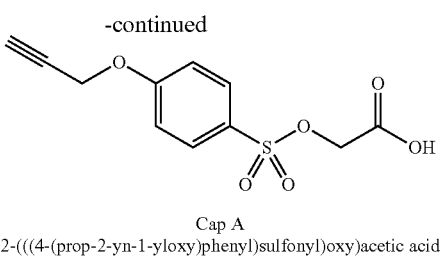

Cap A
2-(((4-(prop-2-yn-1-yloxy)phenyl)sulfonyl)oxy)acetic acid

Methyl 2-(((4-(prop-2-yn-1-yloxy)phenyl)sulfonyl)oxy)acetate (SI-2)

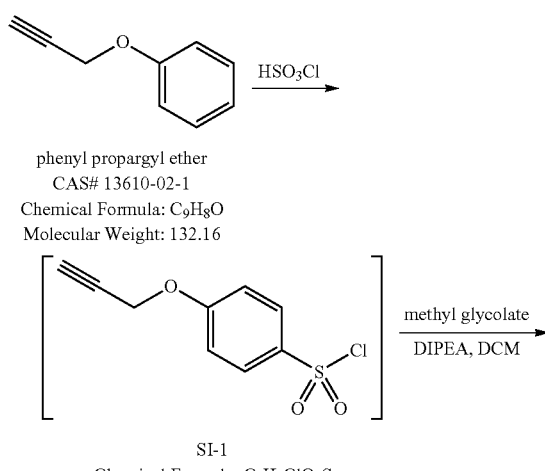

To a round bottom flask was added a magnetic stir bar, phenyl propargyl ether (2.02 g, 15.0 mmol), and the flask was sealed with a septum with positive pressure nitrogen. Dichloromethane (10 mL/g, 20 mL) was added through the septum to form a homogenous solution, and cooled in a 0° C. ice bath. Once equilibrated to temperature, chlorosulfonic acid (4.0 eq, 4.0 mL, 6.91 g) was charged to a glass syringe, pierced through the septum, and added dropwise. After 2.0 mL of the reagent had been added, dropwise over 30 seconds, the solution was black. The reaction progress was monitored by TLC (eluent: 100% EtOAc), with TLC every 0.5 mL of addition after 2.0 mL, monitoring for disappearance of baseline spot (assigned as the intermediate sulfonic acid; the desired sulfonyl chloride was observed with $R_f$ of 0.7, and a large baseline spot. The reaction was complete after the full 4.0 equivalents of chlorosulfonic acid.

To quench, the solution was poured into a separatory funnel with ice water (30 mL/g, 60 mL), diluted with dichloromethane (10 mL/g, 20 mL); saturated brine (15 mL/g, 30 mL) was added to assist in formation of the biphase. The rich organic was the bottom layer, and was drained. The lean aqueous was extracted twice with dichloromethane (10 mL/g each, 20 mL each). The combined organic layers were washed with saturated brine (10 mL/g, 20 mL), dried over magnesium sulfate, filtered, and concentrated. The crude sulfonyl chloride SI-1 was concentrated to a greenish oil with mass of 2.63 g, and used without further purification.

The crude SI-1 (2.63 g) was azeotroped with toluene (4 mL/g, 10 mL), then dissolved in tetrahydrofuran (10 mL/g, 26 mL), and a magnetic stir bar was added. The homogenous solution was allowed to cool in a 0° C. ice bath. To the solution was added triethylamine (4 eq, 3.49 g, 34.5 mmol) in one portion; the solution was homogenous and darkly colored. Methyl glycolate (1.2 eq, 0.946 g, 10.5 mmol) was added dropwise over 20 seconds, and the reaction was left to warm up overnight, after which complete conversion was observed by HPLC.

The crude reaction was diluted in ethyl acetate (20 mL/g, 53 mL), washed with half-saturated ammonium chloride (20 mL/g, 53 mL), then water (20 mL/g, 53 mL), and finally brine (10 mL/g, 26 mL). The rich organic layer was dried over magnesium sulfate, filtered, and concentrated in vacuo. The oil thus obtained was purified by column chromatography (silica, hexane/ethyl acetate). SI-2 was obtained after concentration as an oil with a yield of 41% over the two steps (1.03 g).

SI-2: $^1$H NMR (500 MHz, CD$_3$OD) δ 7.91 (d, J=8.7 Hz, 2H), 7.22 (d, J=8.7 Hz, 2H), 4.90 (s, 2H), 4.67 (s, 2H), 3.71 (s, 3H), 3.06 (m, 1H) ppm; $^{13}$C NMR (126 MHz, CDCl$_3$) δ 166.6, 161.9, 130.4, 127.8, 115.4, 77.2, 76.7, 64.5, 56.1, 54.6 ppm; HRMS (ESI-TOF): calc'd for C$_{12}$H$_{13}$O$_6$S [M+H]$^+$285.0427; found 285.0424.

2-(((4-(prop-2-yn-1-yloxy)phenyl)sulfonyl)oxy)acetic acid (Cap A)

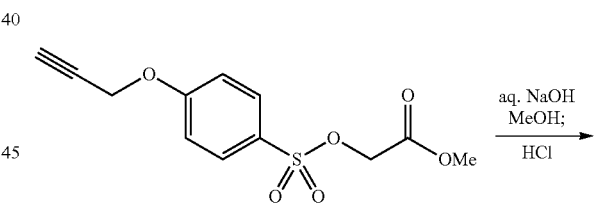

SI-2
methyl 2-(((4-(prop-2-yn-1-yloxy)phenyl)sulfonyl)oxy)acetate
Chemical Formula: C$_{12}$H$_{12}$O$_6$S
Molecular Weight: 284.28

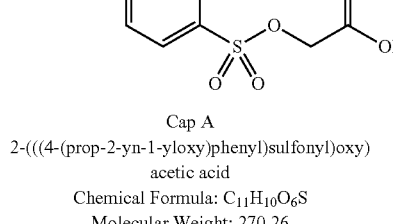

Cap A
2-(((4-(prop-2-yn-1-yloxy)phenyl)sulfonyl)oxy)acetic acid
Chemical Formula: C$_{11}$H$_{10}$O$_6$S
Molecular Weight: 270.26

To a round bottom flask containing SI-2 (1.03 g, 3.61 mmol) was added a magnetic stir bar. To this flask was added methanol (10 mL/g, 10.3 mL), and a homogenous solution formed with stirring. Then aqueous 1M sodium hydroxide (2.5 eq, 9.0 mL, 9.0 mmol) was added dropwise over 30 seconds. Reaction progress was monitored by HPLC, and complete conversion was observed in 5 minutes. The reaction was quenched with dropwise addition of aqueous 1M hydrochloric acid (3.0 eq, 10.8 mL, 10.8 mmol) over 30 seconds with rapid stirring (1000 rpm). The product was allowed to crystallize from the solution over 1 hour, and the product was isolated by filtration. The wet cake was washed further with water (2 mL), and dried with high vacuum. Cap A was obtained in 73% yield (729 mg), with a qNMR potency of 98% ($CD_3OD$, against a fumaric acid internal standard).

Cap A: $^1$H NMR (500 MHz, $CD_3OD$) δ 7.90 (d, J=8.9 Hz, 2H), 7.20 (d, J=8.9 Hz, 2H), 4.87 (d, J=2.1 Hz, 2H), 4.60 (s, 2H), 3.02 (t, J=2.1 Hz, 1H) ppm; $^{13}$C NMR (126 MHz, $CD_3OD$) δ 168.1, 162.2, 130.0, 127.8, 115.2, 77.3, 76.4, 64.4, 55.7 ppm; HRMS (ESI-TOF): calc'd for $C_{11}H_{14}NO_6S$ $[M+NH_4]^+$ 288.0536; found 288.0535.

2-({4-[(3-{2-azatricyclo[10.4.0.0$^{4,9}$]hexadeca-1(12), 4(9),5,7,13,15-hexaen-10-yn-2-yl}-3-oxopropyl) carbamoyl]benzenesulfonyl}oxy)acetic acid (Cap B)

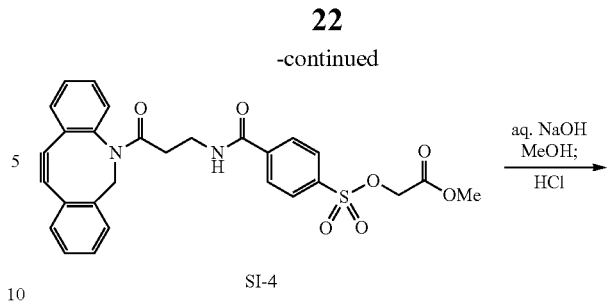

SI-4

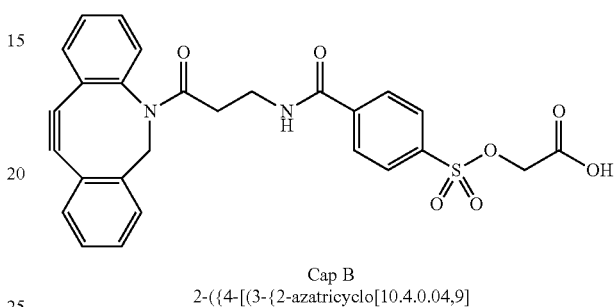

Cap B
2-({4-[(3-{2-azatricyclo[10.4.0.0$^{4,9}$] hexadeca-1(12),4(9),5,7,13,15-hexaen-10-yn-2-yl}-

4-(chlorosulfonyl)benzoyl chloride (SI-3)

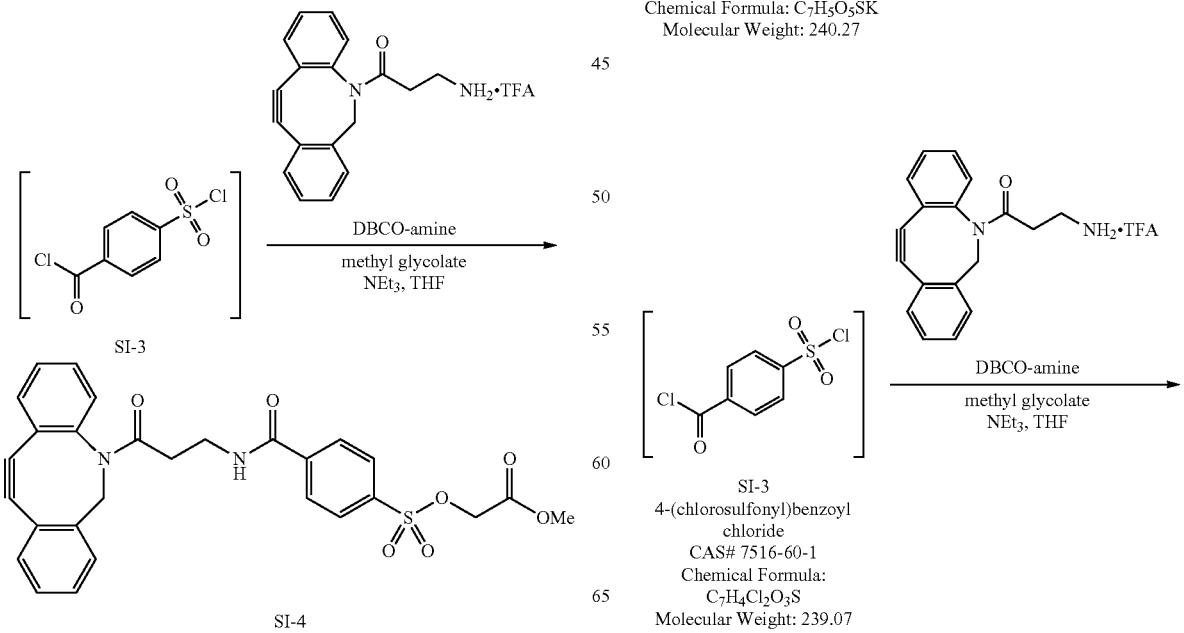

SI-3
4-(chlorosulfonyl)benzoyl chloride
CAS# 7516-60-1
Chemical Formula: $C_7H_4Cl_2O_3S$
Molecular Weight: 239.07

-continued

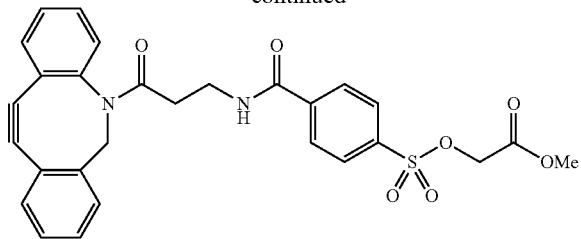

SI-4
methyl 2-({4-[(3-{2-azatricyclo[10.4.0.04,9]
hexadeca-1(12),4(9),5,7,13,15-hexaen-10-yn-2-yl}-
3-oxopropyl)carbamoyl]benzenesulfonyl}oxy)acetate
Chemical Formula: $C_{28}H_{24}N_2O_7S$
Molecular Weight: 532.57

To a round bottom flask with condenser and positive pressure nitrogen line was massed 4-sulfobenzoic acid potassium salt (1.0 grams, 4.2 mmol) and a magnetic stir bar. The flask was vacuum replenished with nitrogen. Then, thionyl chloride (10 mL/g, 10 mL) was added in one portion, and one drop of dimethylformamide. The reaction was a thick slurry, and the flask was heated to a gentle reflux; as the solution approached reflux, it dissolved to form a homogenous solution. The solution was refluxed for two hours, and then cooled to room temperature, and a fine precipitate formed. The solution was diluted with toluene (20 mL/g, 20 mL), filtered through a fritted funnel into a tared flask, and concentrated in vacuo. The oil thus obtained was then azeotroped with toluene (10 mL/g, 10 mL). Then, the oil thus obtained was placed on high vacuum for 1 hour, upon which it solidified to a colorless solid. The final crude SI-3, as a white powder, had a mass of 1.035 grams, and was used without further purification.

The spectroscopic data of SI-3 matches that in McGeary, R. P.; Bennett, A. J.; Tran, Q. B.; Prins, J.; Ross, B. P. *Tetrahedron* 2009, 65, 3990-3997. $^1$H NMR (500 MHz, CDCl$_3$) δ 8.37 (d, J=8.5 Hz, 2H), 8.21 (d, J=8.5 Hz, 2H).

Methyl 2-({4-[(3-{2-azatricyclo[10.4.0.04,9]hexadeca-1(12),4(9),5,7,13,15-hexaen-10-yn-2-yl}-3-oxopropyl)carbamoyl]benzenesulfonyl}oxy)acetate (SI-4)

The dibenzocyclooctyne (DBCO) reagent was purchased commercially as a trifluoroacetate salt, which was used directly. To a reaction vial was added a small stir bar, 4-chlorosulfonylbenzoyl chloride (SI-3, 1.03 eq, 0.512 g, 2.14 mmol), and DBCO-amine trifluoroacetate salt (limiting reagent, 0.807 g, 2.07 mmol). This flask was vacuum replenished with nitrogen, and placed in a dry ice/acetone cooling bath. Tetrahydrofuran (20 mL/g, 10 mL) was added, and allowed to equilibrate to temperature. Triethylamine (4 eq, 1.2 mL, 8.6 mmol) was added dropwise over 1 minute. Immediately following, methyl glycolate (5.0 eq, 0.80 mL, mmol) was added in one portion, and the cooling bath removed; the reaction was a thin slurry. Reaction progress was monitored by HPLC, and was deemed complete in 2 hours at room temperature.

The crude reaction was diluted in ethyl acetate (40 mL/g, 20 mL), washed twice with half-saturated ammonium chloride (40 mL/g each, 20 mL each), then water (40 mL/g, mL), and finally brine (40 mL/g, 20 mL). The rich organic layer was dried over magnesium sulfate, filtered, and concentrated in vacuo. The oil thus obtained was purified by column chromatography (silica, hexane/ethyl acetate). SI-4 was obtained after concentration as an oil with a yield of 53% (595 mg). The structure was confirmed with HSQC and HMBC spectroscopy; correlation was observed between the ethylene and the carboxylate carbon, confirming connectivity.

SI-4: $^1$H NMR (500 MHz, CDCl$_3$) δ 7.94 (d, J=8.2 Hz, 2H), 7.71 (d, J=7.0 Hz, 1H), 7.64 (d, J=8.5 Hz, 2H), 7.44-7.31 (m, 6H), 7.17 (d, J=7.0 Hz, 1H), 6.85 (br s, 1H), 5.17 (d, J=14.0 Hz, 1H), 4.66 (s, 2H), 3.75 (s, 3H), 3.72 (d, J=13.7 Hz, 1H), 3.57-3.46 (m, 2H), 2.54 (ddd, J=16.7, 7.9, 4.1 Hz, 1H), 2.11 (ddd, J=16.7, 7.9, 4.1 Hz, 1H); $^{13}$C NMR (126 MHz, CDCl$_3$) δ 172.2, 166.2, 165.1, 150.8, 147.8, 139.8, 137.9, 132.2, 129.0, 128.7, 128.6, 128.3, 128.3, 127.9, 127.8, 127.4, 125.6, 122.9, 122.5, 114.7, 107.8, 64.8, 55.6, 52.7, 35.9, 34.7 ppm; HRMS (ESI-TOF): calc'd for $C_{28}H_{25}N_2O_7S$ [M+H]$^+$ 533.1377; found 533.1380.

2-({4-[(3-{2-azatricyclo[10.4.0.04,9]hexadeca-1(12),4(9),5,7,13,15-hexaen-10-yn-2-yl}-3-oxopropyl)carbamoyl]benzenesulfonyl}oxy)acetic acid (Cap B)

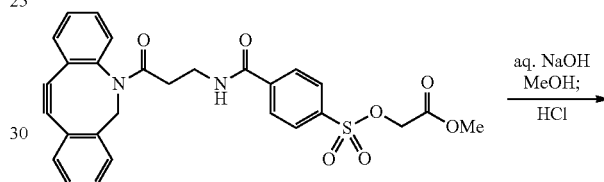

SI-4
Chemical Formula: $C_{28}H_{24}N_2O_7S$
Molecular Weight: 532.57

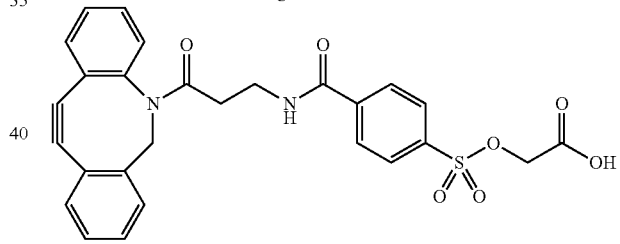

Cap B
2-({4-[(3-{2-azatricyclo[10.4.0.04,9]
hexadeca-1(12),4(9),5,7,13,15-hexaen-10-yn-2-yl}-
3-oxopropy)carbamoyl]benzenesulfonyl}oxy)acetic acid
Chemical Formula: $C_{27}H_{22}N_2O_7S$
Molecular Weight: 518.54

To a round bottom flask was added a magnetic stir bar, and SI-4 (595 mg, 1.12 mmol). To this flask was added methanol (12 mL/g, 7.1 mL), and a homogenous solution formed. With stirring, aqueous 1M sodium hydroxide (2.5 equiv, 2.8 mL) was added dropwise over 30 seconds. Reaction progress was monitored by HPLC, and complete conversion was observed in 5 minutes. The reaction was quenched with dropwise addition of aqueous 1M hydrochloric acid (3.0 eq, 3.4 mL) over 30 seconds, and transferred to a separatory funnel with ethyl acetate (34 mL/g, 20 mL). The solution was washed three times with water (17 mL/g each, mL each), then saturated brine (17 mL/g, 10 mL). The rich organic was dried over magnesium sulfate, filtered, concentrated in vacuo, and dried further on high vacuum. The target compound B was obtained in 98% yield (565 mg), and used without further purification.

B: $^1$H NMR (500 MHz, CD$_3$OD) δ 8.00 (d, J=7.5 Hz, 2H), 7.77 (d, J=7.5 Hz, 2H), 7.70 (d, J=7.9 Hz, 1H), 7.54-7.49 (m, 1H), 7.49-7.42 (m, 3H), 7.39 (t, J=7.3 Hz, 1H), 7.33 (t, J=7.3 Hz, 1H), 7.12 (d, J=7.6 Hz, 1H), 5.19 (d, J=13.7 Hz, 1H), 4.72 (s, 2H), 3.73 (d, J=13.9 Hz, 1H), 3.52-3.44 (m, 1H), 3.43-3.35 (m, 3H), 2.60-2.54 (m, 1H), 2.36-2.28 (m, 1H) ppm; $^{13}$C NMR (126 MHz, CDCl$_3$) δ 171.8, 167.8, 166.5, 151.2, 148.0, 139.3, 138.3, 132.1, 129.0, 128.6, 128.3, 127.9, 127.8, 127.8, 127.6, 126.8, 125.1, 122.9, 122.2, 114.2, 107.5, 64.9, 55.2, 36.2, 33.8 ppm; HRMS (ESI-TOF): calc'd for C$_{27}$H$_{23}$N$_2$O$_7$S [M+H]$^+$ 519.1220; found 519.1224.

Synthesis of 2-(((4-((3-azidopropoxy)carbonyl)phenyl)sulfonyl)oxy)acetic acid (Cap C)

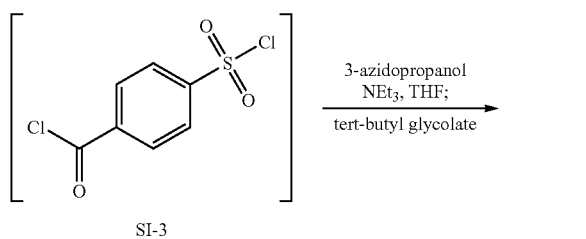

SI-3

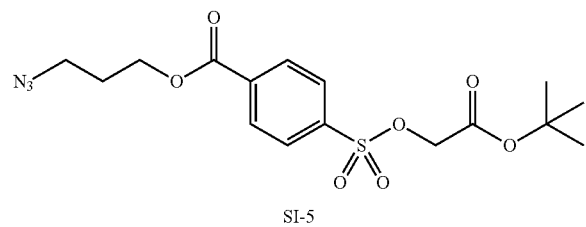

SI-5

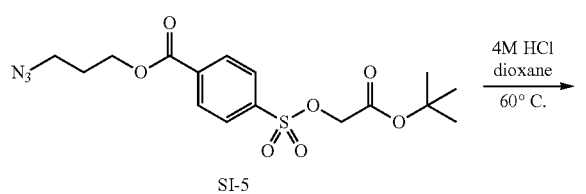

SI-5

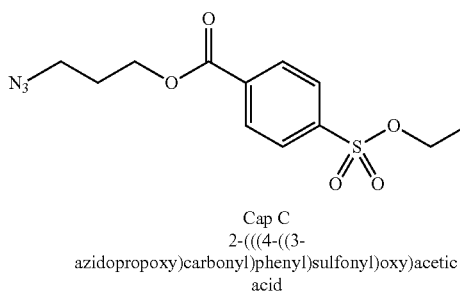

Cap C
2-(((4-((3-azidopropoxy)carbonyl)phenyl)sulfonyl)oxy)acetic acid

3-azidopropyl 4-((2-(tert-butoxy)-2-oxoethoxy)sulfonyl)benzoate (SI-5)

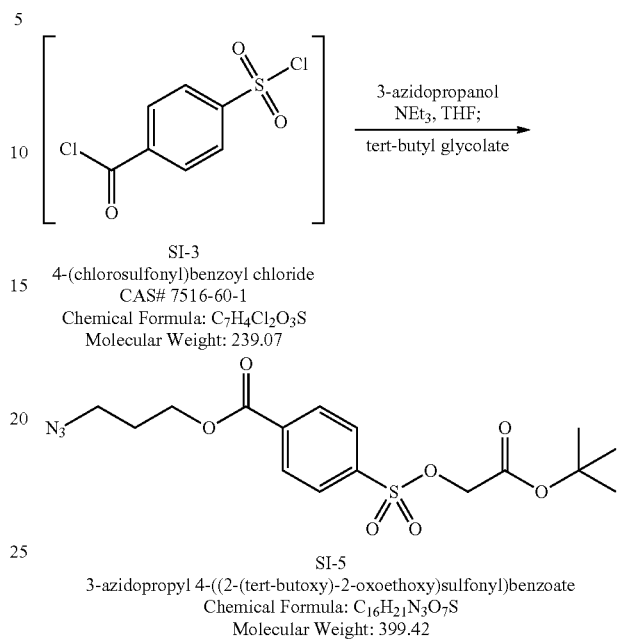

SI-3
4-(chlorosulfonyl)benzoyl chloride
CAS# 7516-60-1
Chemical Formula: C$_7$H$_4$Cl$_2$O$_3$S
Molecular Weight: 239.07

SI-5
3-azidopropyl 4-((2-(tert-butoxy)-2-oxoethoxy)sulfonyl)benzoate
Chemical Formula: C$_{16}$H$_{21}$N$_3$O$_7$S
Molecular Weight: 399.42

To a 20 mL reaction vial with magnetic stir bar was massed 4-chlorosulfonylbenzoyl chloride (See procedure above; SI-3, limiting reagent, 0.501 g, 2.10 mmol), and the vial was capped with a septum and positive pressure nitrogen line. Through the septum was added tetrahydrofuran (20 mL/g, 10 mL), and the vial was cooled in a dry ice/acetone bath. Upon equilibrating to temperature, triethylamine (2.0 eq, 0.58 mL, 4.2 mmol) was added in one portion, followed by 3-azidopropan-1-ol (1.0 eq, 0.219 grams, 0.20 mL, 2.09 mmol). The vial was allowed to react in the cooling bath. After one hour, complete conversion was observed (reaction progress monitored by HPLC), and tert-butyl glycolate (1.5 eq, 0.415 g, 3.14 mmol), and the cooling bath was removed and the vial was allowed to warm to room temperature. After one hour, conversion was observed to be 24%, and the reaction was allowed to stir overnight at room temperature to reach completion.

The crude reaction was diluted in ethyl acetate (40 mL/g, 20 mL), washed twice with water (20 mL/g each, 10 mL each), and finally brine (10 mL/g, 5 mL). The rich organic layer was dried over magnesium sulfate, filtered, and concentrated in vacuo. The oil thus obtained was purified by column chromatography (silica, heptane/ethyl acetate). SI-5 was obtained after concentration as a solid with a yield of 63% (526 mg). The structure was confirmed with HSQC and HMBC spectroscopy; correlation was observed between the azidopropyl methylene and the carboxylate carbon, confirming connectivity.

SI-5: $^1$H NMR (500 MHz, CDCl$_3$) δ 8.22 (d, J=7.9 Hz, 2H), 8.04 (d, J=8.2 Hz, 2H), 4.55 (s, 2H), 4.48 (t, J=6.1 Hz, 2H), 3.50 (t, J=6.4 Hz, 2H), 2.08 (quintet, J=6.3 Hz, 2H), 1.43 (s, 9H) ppm; $^{13}$C NMR (126 MHz, CDCl$_3$) δ 164.7, 164.6, 140.0, 134.9, 130.3, 128.1, 83.6, 65.5, 62.8, 48.2, 28.1, 27.9 ppm; HRMS (ESI-TOF): calc'd for C$_{16}$H$_{25}$N$_4$O$_7$S [M+NH$_4$]$^+$ 417.1438; found 417.1438.

2-(((4-((3-azidopropoxy)carbonyl)phenyl)sulfonyl)oxy)acetic acid (Cap C)

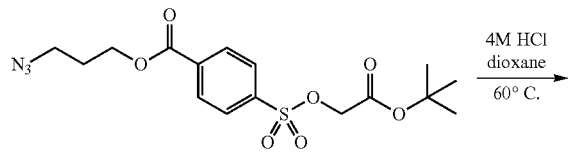

SI-5
3-azidopropyl 4-((2-(tert-butoxy)-2-oxoethoxy)sulfonyl)benzoate
Chemical Formula: C$_{16}$H$_{21}$N$_3$O$_7$S
Molecular Weight: 399.42

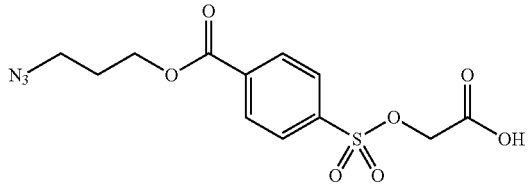

Cap C
2-(((4-((3-azidopropoxy)carbonyl)phenyl)sulfonyl)oxy)acetic acid
Chemical Formula: C$_{12}$H$_{13}$N$_3$O$_7$S
Molecular Weight: 343.31

To a 10 mL round bottom flask with condenser and positive pressure nitrogen line was massed 3-azidopropyl 4-((2-(tert-butoxy)-2-oxoethoxy)sulfonyl)benzoate (SI-5, 526 mg, 1.32 mmol), and a small magnetic stir bar. Hydrochloric acid (4M in dioxane) (20 eq, 6.6 mL, 26 mmol) was added in one portion to form a homogenous solution. The reaction was placed in a 60° C. reaction block, and reaction progress was monitored by HPLC; conversion was 50% in 1 hour. The reaction was stirred overnight at 60° C. Complete conversion was observed overnight, and the solution was concentrated directly in vacuo. The crude solid thus obtained was azeotroped from toluene, and placed on high vacuum. Cap C was obtained as a white powder with 93% yield (83.3 mg), and was used without further purification. The crude solid could also be crystallized from hot toluene to high purity in 76% yield, although this was not necessary.

Cap C: $^1$H NMR (500 MHz, CDCl$_3$) δ 8.24 (d, J=8.5 Hz, 2H), 8.05 (d, J=8.5 Hz, 2H), 4.72 (s, 2H), 4.50 (t, J=6.2 Hz, 2H), 3.52 (t, J=6.6 Hz, 2H), 2.10 (quintet, J=6.4 Hz, 2H) ppm; $^{13}$C NMR (126 MHz, CDCl$_3$) δ 170.2, 164.7, 139.5, 135.2, 130.5, 128.2, 64.4, 62.9, 48.2, 28.1 ppm; HRMS (ESI-TOF): calc'd for C$_{12}$H$_{17}$N$_4$O$_7$S [M+NH$_4$]$^+$ 361.0812; found 361.0811.

Synthesis of 2-(((4-(3-azidopropoxy)phenyl)sulfonyl)oxy)acetic acid (Cap D)

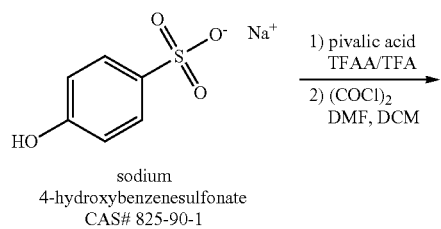

sodium 4-hydroxybenzenesulfonate
CAS# 825-90-1

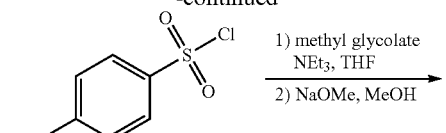

SI-7

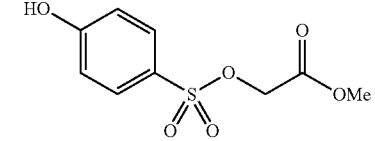

SI-8

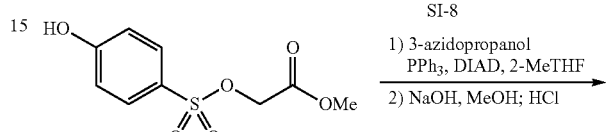

SI-9

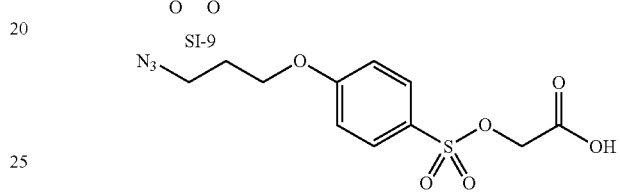

Cap D
2-(((4-(3-azidopropoxy)phenyl)sulfonyl)oxy)acetic acid

Sodium 4-pivaloylbenzenesulfonate (SI-6)

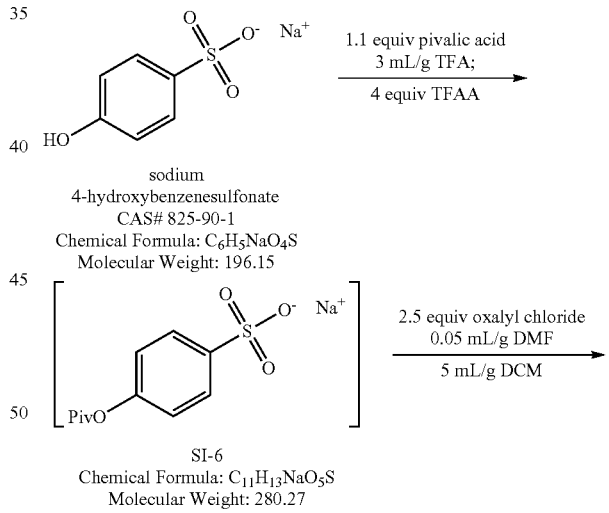

sodium 4-hydroxybenzenesulfonate
CAS# 825-90-1
Chemical Formula: C$_6$H$_5$NaO$_4$S
Molecular Weight: 196.15

SI-6
Chemical Formula: C$_{11}$H$_{13}$NaO$_5$S
Molecular Weight: 280.27

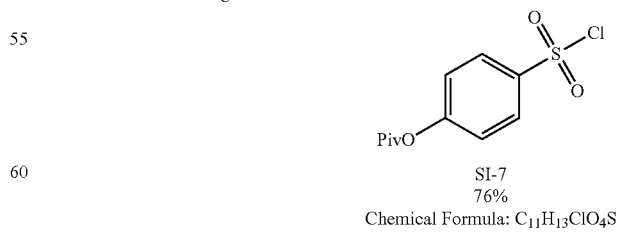

SI-7
76%
Chemical Formula: C$_{11}$H$_{13}$ClO$_4$S
Molecular Weight: 276.73

To a 500 mL round bottom flask was added a magnetic stir bar, sodium 4-hydroxybenzenesulfonate (limiting reagent, 25.02 g, 126.3 mmol), and pivalic acid (1.1 eq, 14.2 g, 139 mmol); the flask was capped with a septum and positive pressure nitrogen line. To this flask was added trifluoroacetic acid (3 mL/g, 75 mL), which formed a thick slurry upon stirring. Upon the addition of trifluoroacetic anhydride (4 eq, 71.4 mL, 505 mmol), dropwise, the solution became hot, and went homogenous. Then, the stir bar was removed, and the solution concentrated in vacuo in a 40° C. water bath to a white powder (crude mass of 54.7 grams). Acetonitrile (100 mL) was added, and the solution was evaporated again in vacuo, then placed on high vacuum for 3 hours. The final crude SI-6, as a white powder, had a mass of 38.66 g.

4-pivaloylbenzenesulfonyl chloride (SI-7)

To the flask containing SI-7 (126 mmol, MW 280.27, crude), as a white powder, was added a magnetic stir bar and capped with a septum and positive pressure nitrogen line. To this flask was added dichloromethane (5 mL/g, 177 mL), DMF (0.05 mL/mmol, 1.76 mL) through the septum. The solution formed a thick slurry upon stirring. To this solution was added oxalyl chloride (2.0 mol/L solution in DCM, 158 mL, 316 mmol). The solution was allowed to stir at ambient temperature overnight. Once complete, the crude reaction mixture was poured into ethyl acetate (20 mL/g, 697 mL), and washed with water (8 mL/g, 279 mL), then 20% brine (8 mL/g, 279 mL), then saturated brine (4 mL/g, 139 mL). The rich organic layer was dried over magnesium sulfate, filtered, and concentrated in vacuo to a solid. The crude solid was isolated by crystallization from 1.5:1 heptane:toluene (v/v, 4 mL/g, 139 mL) for a first crop, then a second crop of crystals was obtained from 3:1 heptane:toluene (v/v, 1.15 mL/g, 40 mL). The combined isolated yield of SI-7 was 76% (26.46 g, 95.6 mmol).

The spectroscopic data of SI-7 matches that of Bijukumar, G. et al., *Synth. Commun.* 2008, 38, 1718-1724 and commercial compound. SI-7: $^1$H NMR (500 MHz, CDCl$_3$) δ 8.09 (d, J=8.7 Hz, 2H), 7.37 (d, J=8.7 Hz, 2H), 1.41 (s, 9H) ppm.

4-((2-methoxy-2-oxoethoxy)sulfonyl)phenyl pivalate (SI-8)

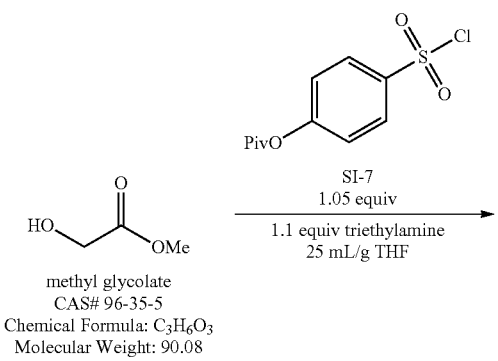

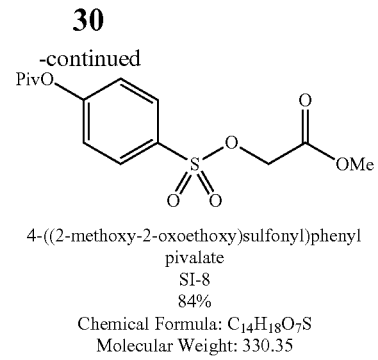

4-((2-methoxy-2-oxoethoxy)sulfonyl)phenyl pivalate
SI-8
84%
Chemical Formula: C$_{14}$H$_{18}$O$_7$S
Molecular Weight: 330.35

To a 300 mL round bottom flask was added a magnetic stir bar, 4-(chlorosulfonyl)phenyl pivalate (SI-7, 1.05 eq, 26.02 g, 94.0 mmol), and the flask was capped with a septum with positive pressure nitrogen line. To the flask was added tetrahydrofuran (25 g/mL relative to methyl glycolate, 202 mL), added via cannula through the septum, and the flask was cooled in a 0° C. ice bath. Upon equilibrating to temperature, methyl glycolate (limiting reagent, 8.06 g, 89.49 mmol) was added in a single portion, followed by dropwise addition of triethylamine (1.1 eq, 9.74 g, 96.3 mmol) over a minute.

The reaction was left to warm to room temperature overnight. Progress was monitored by HPLC, and the reaction was complete after 24 hours. To workup, the process stream was diluted with MTBE (10 mL/g relative to the input sulfonyl chloride, 260 mL), and subsequently washed with the following: twice with half-saturated aqueous ammonium chloride (8 mL/g, 208 mL each wash), then water (8 mL/g, 208 mL), then brine (4 mL/g, 104 mL). The rich organic stream was then dried over magnesium sulfate, filtered, and concentrated to dryness in vacuo to form a thick oil that solidified upon standing.

The crude SI-8 was crystallized from hot 3:1 heptane: MTBE (v/v, 4 mL/g of input sulfonyl chloride). Pure SI-8, as off-white crystals, was isolated upon cooling to 0° C. with rapid stirring. The isolated yield of SI-8 was 84% (24.73 g, 74.9 mmol).

SI-8: $^1$H NMR (500 MHz, CDCl$_3$) δ 7.98 (d, J=8.7 Hz, 2H), 7.27 (d, J=8.7 Hz, 2H), 4.64 (s, 2H), 3.73 (s, 3H), 1.37 (s, 9H) ppm; $^{13}$C NMR (126 MHz, CDCl$_3$) δ 176.2, 166.3, 155.6, 132.6, 129.8, 122.6, 64.8, 52.7, 39.3, 27.0 ppm; HRMS (ESI-TOF): calc'd for C$_{14}$H$_{19}$O$_7$S [M+H]$^+$ 331.0846; found 331.0845.

Methyl 2-(((4-hydroxyphenyl)sulfonyl)oxy)acetate (SI-9)

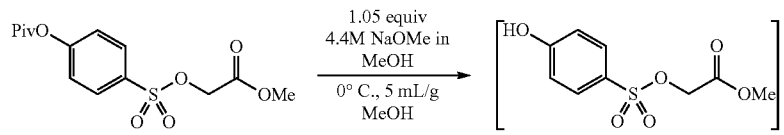

SI-8
Chemical Formula: C$_{14}$H$_{18}$O$_7$S
Molecular Weight: 330.35 methyl 2-(((4-hydrophenyl)sulfonyl)oxy)acetate
SI-9
Chemical Formula: C$_9$H$_{10}$O$_6$S
Molecular Weight: 246.23

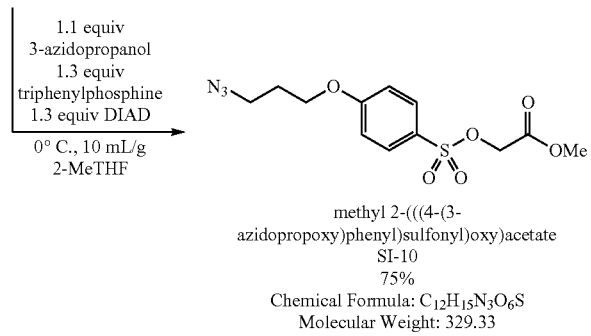

methyl 2-(((4-(3-azidopropoxy)phenyl)sulfonyl)oxy)acetate
SI-10
75%
Chemical Formula: C$_{12}$H$_{15}$N$_3$O$_6$S
Molecular Weight: 329.33

To a 500 mL flask with SI-8 (limiting reagent, 24.33 g, 73.64 mmol) was added a magnetic stir bar, and methanol (5 mL/g, 122 mL). The flask was cooled to 0° C. in an ice bath with moderate stirring, and formed a thin slurry upon cooling. Upon equilibration to temperature, sodium methoxide (25 wt % solution in MeOH, 1.05 eq, 17.7 mL, 77.3 mmol) was added slowly via syringe pump over 30 minutes.

The reaction reached homogeneity 10 minutes after completion of the sodium methoxide addition, and reaction completion was observed by HPLC. The reaction was quenched with the addition of aqueous hydrochloric acid (1 mol/L, 147 mL, 147 mmol). The process stream was extracted three times with dichloromethane (8 mL/g, 195 mL each), and the combined organic layers were washed with brine (5 mL/g, 122 mL), dried over magnesium sulfate, filtered and concentrated in vacuo. The crude product was then azeotroped with toluene to yield an off-white crystal. The solid SI-9 recovered, 17.13 g, was telescoped forward as is.

SI-9: $^1$H NMR (500 MHz, CD$_3$OD) δ 7.78 (d, J=7.5 Hz, 2H), 6.97 (d, J=7.6 Hz, 2H), 6.48 (s, 1H), 4.63 (s, 2H), 3.71 (s, 3H) ppm; $^{13}$C NMR (126 MHz, CD$_3$OD) δ 167.1, 163.0, 130.3, 125.1, 115.6, 64.4, 51.5 ppm; HRMS (ESI-TOF): calc'd for C$_9$H$_{11}$O$_6$S [M+H]$^+$247.0271; found 247.0279.

Methyl 2-(((4-(3-azidopropoxy)phenyl)sulfonyl)oxy)acetate (SI-10)

To the flask containing the crude SI-9 (limiting reagent, 15.20 g, 61.73 mmol) was added a magnetic stir bar, 2-methyltetrahydrofuran (10 mL/g, 152 mL), and cooled in a 0° C. bath. Upon equilibration to temperature, 3-azidopropan-1-ol (1.1 eq, 7.04 g, 69.6 mmol) was added. Then, triphenylphosphine (1.3 eq, 21.02 g, 80.14 mmol) was added in one portion, followed immediately by the dropwise addition of diisopropyl azodicarboxylate (1.3 eq, 16.32 g, mmol) over 1 minute.

The reaction was complete after one hour. The crude process stream was diluted in MTBE (10 mL/g, 152 mL), washed with half-saturated ammonium chloride (5 mL/g, 76 mL), then water (5 mL/g, 76 mL), and finally brine (5 mL/g, 76 mL). The rich organic layer was dried over magnesium sulfate, filtered, and concentrated in vacuo. The oil thus obtained was purified by column chromatography (silica, hexane/ethyl acetate, eluted at 35% ethyl acetate). SI-10 was obtained after concentration as a solid with a yield of 75% (26.13 g, 58% potency by qNMR (CD$_3$OD, fumaric acid internal standard), with 41% reduced-DIAD). This material was used without further purification.

SI-10: $^1$H NMR (500 MHz, CDCl$_3$) δ 7.88 (d, J=8.5 Hz, 2H), 7.02 (d, J=8.4 Hz, 2H), 4.59 (s, 2H), 4.14 (t, J=5.2 Hz, 2H), 3.74 (s, 3H), 3.54 (t, J=6.0 Hz, 2H), 2.09 (quin, J=5.9 Hz, 2H) ppm; $^{13}$C NMR (126 MHz, CDCl$_3$) δ 166.6, 163.2, 130.4, 127.1, 114.9, 64.5, 52.6, 48.0, 28.5 ppm; HRMS (ESI-TOF): calc'd for C$_{12}$H$_{19}$N$_4$O$_6$S [M+NH$_4$]$^+$347.1020; found 347.1013.

2-(((4-(3-azidopropoxy)phenyl)sulfonyl)oxy)acetic acid (Cap D)

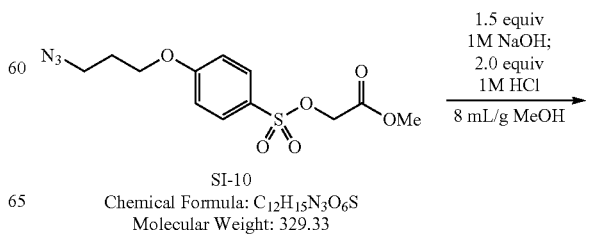

SI-10
Chemical Formula: C$_{12}$H$_{15}$N$_3$O$_6$S
Molecular Weight: 329.33

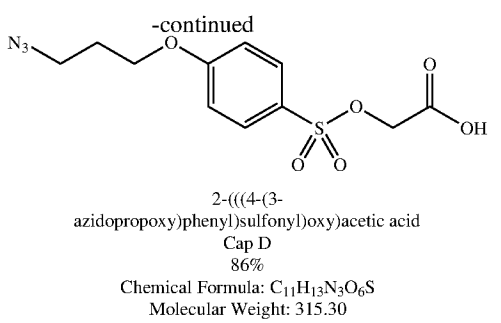

2-(((4-(3-azidopropoxy)phenyl)sulfonyl)oxy)acetic acid
Cap D
86%
Chemical Formula: $C_{11}H_{13}N_3O_6S$
Molecular Weight: 315.30

To a 500 mL reaction flask was added SI-10 (limiting reagent, 25.58 g, 45.3 mmol, 58.3% potency) and a magnetic stir bar. To this flask was added methanol (8 mL/g, 205 mL), which was heated gently while stirring. After reached homogeneity at a solution temperature of 32° C., the solution was then allowed to cool and placed in a 0° C. ice bath. The solution formed a thick slurry at a solution temp of 12° C.

At a solution temperature of 10° C., aqueous sodium hydroxide (1.0 mol/L, 1.5 eq, 68 mL, 68 mmol) was added dropwise over 2 minutes, maintaining an internal solution temperature below 12° C. Upon completion of the addition, the solution was homogenous, and reaction completion was observed. The solution was warmed to room temperature, and aqueous hydrochloric acid (1 mol/L, 2 eq, 90 mL, 90 mmol) was added in one portion. A thick slurry rapidly formed, and the reaction was gently warmed to an internal solution temperature of 32° C. to reach homogeneity. Then, the solution was cooled slowly over one hour to 0° C. to form a thick slurry, which was subsequently aged at 0° C. for one hour with stirring. The thick slurry was filtered, and the wet cake was rinsed with 1:1 water:methanol (v/v, 1 mL/mmol, 45 mL). The isolated Cap D thus obtained was collected and further dried over vacuum. The isolated yield of Cap D was 86% (12.26 g, 38.9 mmol). The potency of the solid obtained was 100% by qNMR ($CD_3OD$, fumaric acid internal standard). The $^{13}C$ NMR spectrum was acquired in $CDCl_3$ despite limited solubility; in $CD_3OD$, a signal was obscured by the solvent peak at 49 ppm.

Cap D: $^1H$ NMR (500 MHz, $CD_3OD$) δ 7.88 (d, J=8.9 Hz, 2H), 7.14 (d, J=9.0 Hz, 2H), 4.58 (s, 2H), 4.18 (t, J=6.0 Hz, 2H), 3.53 (t, J=6.6 Hz, 2H), 2.07 (quin, J=6.3 Hz, 2H) ppm;

$^{13}C$ NMR (126 MHz, $CDCl_3$) δ 171.0, 163.4, 130.5, 126.8, 115.0, 65.2, 63.8, 48.0, 28.5 ppm;

Loading of the Dibenzocyclooctyne (DBCO) onto Polyethylene Glycol (PEG) Resins

The catch resins were synthesized via the following procedures. Resin loading was then quantified by HPLC against an internal standard.

General Procedure for the Quantitation of the Resin Loading

The resin loading was determined by HPLC disappearance of an azide reagent relative to a known internal standard, as follows. Azide reagent, Cap D, prepared above, was massed into a 10 mL volumetric (MW 315.30, 40.0-50.0 mg), followed by Fmoc-proline-OH (internal standard, about 30 mg). This standard solution prepared with a diluent of methanol, to prepare a solution of 12.7 to 15.9 millimolar concentration of azide. An HPLC sample of the standard solution was taken as a reference (100 uL of standard solution diluted in 500 uL of methanol).

Two samples of the resin (40.0-50.0 mg) were massed into small vials, to run the quantitation in duplicate. The resin was swollen in methanol (0.20 mL), and then an aliquot of the standard azide solution (0.800 mL) was added to each vial. The vials were then vortexed and placed on a shaker to react. Samples of the supernatant of each vial were prepared after 6 hours (100 uL of supernatant diluted in 500 uL of methanol, then filtered for HPLC analysis).

The loading for each sample and time point can then be calculated with the following equation:

$$\text{loading } \frac{\text{mmol}}{\text{gram}} = \left(1 - \frac{A_4 \times \frac{A_1}{A_3}}{A_2}\right) \times \frac{0.80 \text{ mL} \times B}{C}$$

$A_1$=HPLC area of Fmoc-Pro-OH in the standard
$A_2$=HPLC area of Cap D in the standard
$A_3$=HPLC area of Fmoc-Pro-OH in the sample
$A_4$=HPLC area of Cap D in the sample
B=mmol/mL of Cap D in the standard
C=grams of resin massed in the sample Synthesis of Catch Resin A-SPAAC Alkyne Loaded to PEG-Wang Resin Via Succinamide Linker

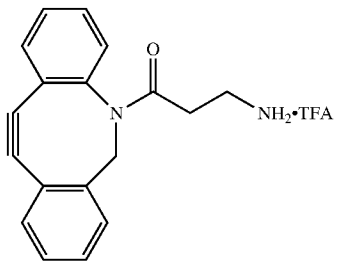

DBCO-amine
Chemical Formula: $C_{20}H_{17}F_3N_2O_3$
Molecular Weight: 390.36

1) succinic anhydride
DIPEA, DMF;
pentafluorophenyl trifluoroacetate
DMAP;
then washed resin,
swollen in DMF
2) capping: $Ac_2O$, DIPEA, DMF

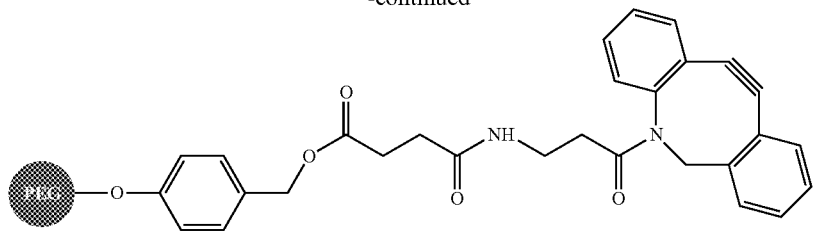

Catch Resin A
SPAAC resin, PEG-Wang resin,
succinamide linker

Preparation of the Wang-PEG resin. To a 25 mL fritted bottom reactor was added NovaPEG Wang resin (0.46 mmol/g, 1.63 g, 0.75 mmol). The resin was swollen in DMF with nitrogen bubbling through the fit for agitation. After 5 minutes of agitation, the DMF was drained through the frit by vacuum. Then, the resin was washed similarly, in the following protocol [5 minutes per wash, with nitrogen bubbling for agitation]: DMF, DCM (twice), DMF, 2% DIPEA in DMF (v/v) (twice), and finally DMF. After draining the last rinse, the swollen resin was suspended in DMF to prepare for the loading.

Activation of the DBCO-amine. The dibenzocyclooctyne (DBCO) reagent was purchased commercially as a trifluoroacetate salt, which was used directly as is. To an 8 mL vial was massed DBCO-amine trifluoroacetate salt (95% purity, 0.205 g, 0.500 mmol), which was dissolved in DMF (25 mL/g, 5.0 mL), and a magnetic stir bar was added. Then, DIPEA (2.5 eq, 0.22 mL, 1.25 mmol) was added, followed by succinic anhydride (1.0 eq, 0.050 g, 0.50 mmol) in one portion. HPLC analysis at 5 minutes shows complete conversion to the succinate-homologated intermediate. The solution was held until ready to load the resin.

Loading of the DBCO-amine. The NovaPEG Wang resin, which had been washed and suspended in DMF, was agitated by nitrogen bubbling. Diisopropyl carbodiimide (1.2 eq, 0.094 mL, 0.60 mmol) was added to the succinate-homologated DBCO intermediate solution, and then the solution was added immediately to the DMF-suspended resin. To the resin/DBCO solution was added 4-dimethylaminopyridine (0.16 eq, 10 mg). The solution was allowed to mix overnight with nitrogen bubbling for agitation.

After 24 hours of reaction time, the solvent was drained from the catch resin through the fit with vacuum. The catch resin was washed extensively with DMF, then DCM, and finally MTBE. The catch resin was dried in vacuum. The mass of catch resin after drying was 1.72 grams. The catch resin loading was quantified following the general procedure above, with loading determined to be 0.126 mmol/gram.

Synthesis of Catch Resin B—SPAAC Alkyne Loaded to PEG-Amino Resin Via Succinamide Linker

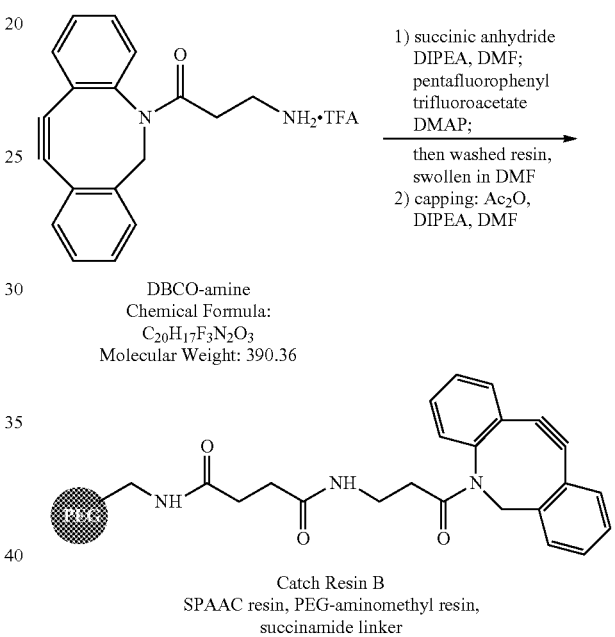

DBCO-amine
Chemical Formula:
$C_{20}H_{17}F_3N_2O_3$
Molecular Weight: 390.36

1) succinic anhydride DIPEA, DMF;
pentafluorophenyl trifluoroacetate
DMAP;
then washed resin, swollen in DMF
2) capping: $Ac_2O$, DIPEA, DMF Catch Resin B
SPAAC resin, PEG-aminomethyl resin,
succinamide linker Preparation of the amino-PEG resin. To a 25 mL fritted bottom reactor was added NovaPEG amino resin (0.66 mmol/g, 0.50 g, 0.33 mmol). The resin was swollen in DMF with nitrogen bubbling through the frit for agitation. After 5 minutes of agitation, the DMF was drained through the frit by vacuum. Then, the resin was washed similarly, in the following protocol [5 minutes per wash, with nitrogen bubbling for agitation]: DMF, DCM (twice), DMF, 2% DIPEA in DMF (v/v) (twice), and finally DMF. After draining the last rinse, the swollen resin was suspended in DMF to prepare for the loading.

Activation of the DBCO-amine. The dibenzocyclooctyne (DBCO) reagent was purchased commercially as a trifluoroacetate salt, which was used directly as is. To an 8 mL vial was massed DBCO-amine trifluoroacetate salt (95% purity, 0.255 g, 0.653 mmol), which was dissolved in DMF (10 mL/g, 2.6 mL), and a magnetic stir bar was added. Then, DIPEA (4.0 eq, 0.46 mL, 2.6 mmol) was added, followed by succinic anhydride (1.0 equiv, 0.068 g, 0.68 mmol) in one portion. HPLC analysis at 5 minutes shows complete conversion to the succinate-homologated intermediate. Then, 4-dimethylaminopyridine (1.0 eq, 81 mg, 0.66 mmol), followed by pentafluorophenyl trifluoroacetate (1.0 eq, 184 mg, 0.657 mmol) were added, and HPLC analysis showed complete conversion to the activated pentafluorophenyl ester in 1 minute.

Loading of the DBCO-amine. The NovaPEG amino resin, which had been washed and suspended in DMF, was agitated by nitrogen bubbling. The activated pentafluorophenyl ester solution of DBCO was added directly to the resin, and the solution was allowed to mix overnight with nitrogen bubbling for agitation.

After agitation overnight, the solvent was drained from the resin through the frit with vacuum, and the resin was rinsed with DMF. Then, an acetate capping solution was prepared in an Erlenmeyer flask by the addition of DMF (8 mL), DIPEA (1.15 mL, 6.6 mmol), and acetic anhydride (0.62 mL, 6.6 mmol). The resin was suspended in minimal DMF, and the capping solution was added in one portion, and allowed to mix with nitrogen agitation for 30 minutes. Then, the capping solution was drained, and the catch resin was washed extensively with DMF, then DCM, and finally MTBE. The catch resin was dried in vacuum. The mass of catch resin after drying was 0.53 grams. The catch resin loading was quantified following the general procedure above, with loading determined to be 0.226 mmol/gram.

Synthesis of Catch Resin C—SPAAC Alkyne Loaded to PEG-Rink Resin Via Succinamide Linker DMF, 2% DIPEA in DMF (v/v) (twice), and finally DMF. After draining the last rinse, the swollen resin was suspended in DMF to prepare for the loading.

Activation of the DBCO-amine. The dibenzocyclooctyne (DBCO) reagent was purchased commercially as a trifluoroacetate salt, which was used directly as is. To an 8 mL vial was massed DBCO-amine trifluoroacetate salt (95% purity, 0.156 g, 0.400 mmol), which was dissolved in DMF (11 mL/g, 1.7 mL), and a magnetic stir bar was added. Then, DIPEA (2.5 eq, 0.174 mL, 1.0 mmol) was added, followed by succinic anhydride (1.0 eq, 0.040 g, 0.40 mmol) in one portion. HPLC analysis at 5 minutes shows complete conversion to the succinate-homologated intermediate. Then, 4-dimethylaminopyridine (1.0 eq, 49 mg, 0.40 mmol), followed by pentafluorophenyl trifluoroacetate (1.0 eq, 112 mg, 0.40 mmol) were added, and HPLC analysis showed complete conversion to the activated pentafluorophenyl ester in 1 minute.

Loading of the DBCO-amine. The Rink Amide-PEG resin, which had been washed and suspended in DMF, was agitated by nitrogen bubbling. The activated pentafluorophenyl ester solution of DBCO was added directly to the resin, and the solution was allowed to mix overnight with nitrogen bubbling for agitation.

After agitation overnight, the solvent was drained from the resin through the frit with vacuum, and the resin was

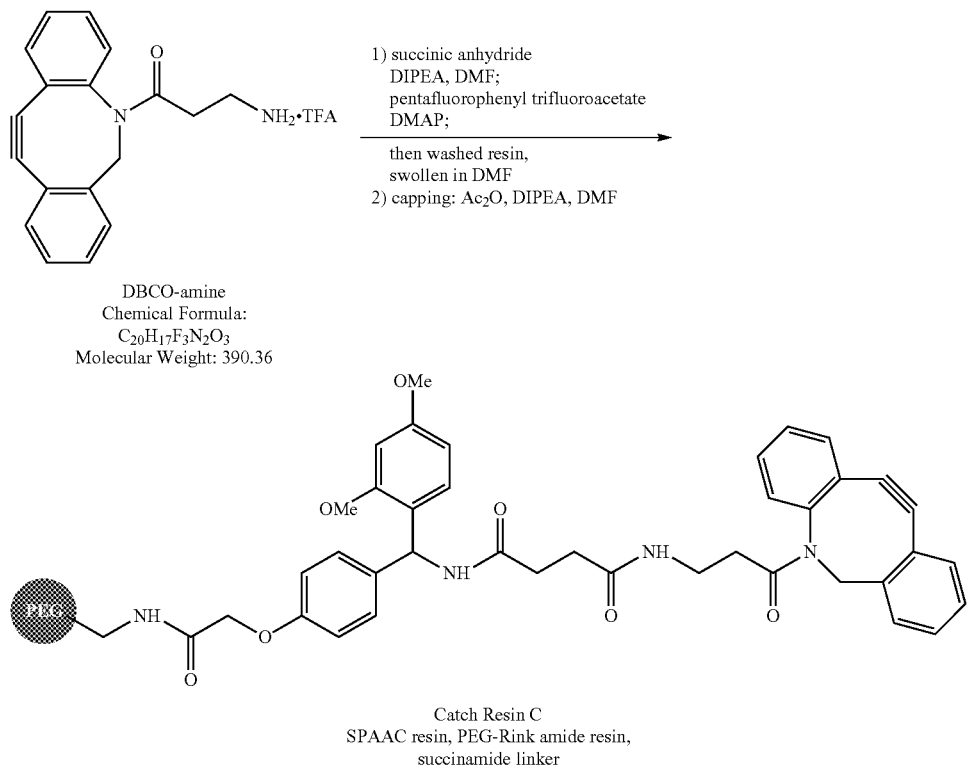

Preparation of the Rink amide-PEG resin. To a 100 mL fritted bottom reactor was added NovaPEG Rink Amide resin (0.180 mmol/g, 1.11 g, 0.2 mmol). The resin was swollen in DMF with nitrogen bubbling through the frit for agitation. After 5 minutes of agitation, the DMF was drained through the fit by vacuum. Then, the resin was washed similarly, in the following protocol [5 minutes per wash, with nitrogen bubbling for agitation]: DMF, DCM (twice), washed with DMF, DCM, and finally MTBE. The resin was dried under vacuum. The resin passed a ninhydrin test for the presence of free amine, and thus was not capped with acetic anhydride. The mass of catch resin after drying was 1.04 grams. The catch resin loading was quantified following the general procedure above, and loading was determined to be 0.121 mmol/gram.

Synthesis of Catch Resin D—SPAAC Alkyne Loaded to PEG Via Urea Linker

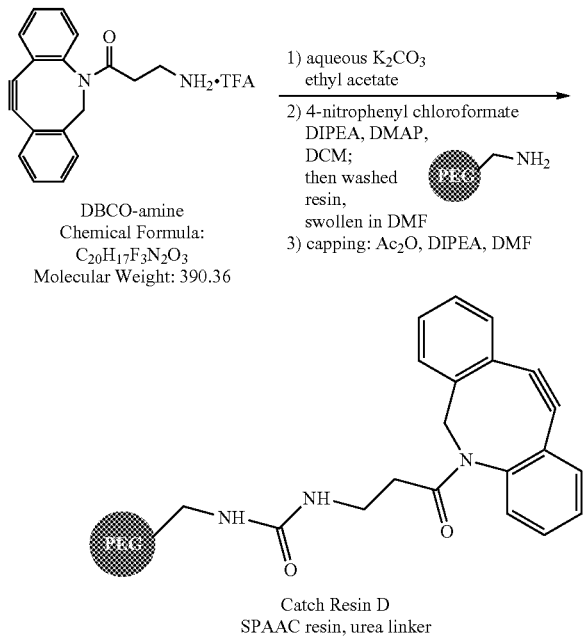

Catch Resin D
SPAAC resin, urea linker

Freebase of DBCO-amine. The dibenzocyclooctyne (DBCO) reagent was purchased commercially as a trifluoroacetate salt, which was freebased before activation. The DBCO-amine trifluoroacetate salt (95% purity, 1.64 g, 4.2 mmol) was added to a separatory funnel, followed by ethyl acetate (50 mL/g, 82 mL). A slurry formed, to which was added 0.4M aqueous potassium carbonate (25 mL/g, 41 mL, 16.4 mmol, 4 eq), and then saturated sodium chloride (25 mL/g, 41 mL). The separatory funnel was shaken, and a homogenous bilayer rapidly formed. The lean aqueous was drained, and the rich organic layer was dried over magnesium sulfate, filtered, concentrated in vacuo to a thick oil. The thick oil was azeotroped with toluene (25 mL/g, 41 mL). The oil thus obtained was used directly, without purification.

Preparation of the amino-PEG resin. To a 500 mL fritted bottom reactor was added Aminomethyl-PEG resin (0.56 mmol/g, 15.0 g, 8.4 mmol). The resin was swollen in DMF with nitrogen bubbling through the frit for agitation. After 5 minutes of agitation, the DMF was drained through the frit by vacuum. Then, the resin was washed similarly, in the following protocol [5 minutes per wash, with nitrogen bubbling for agitation]: DMF, DCM (twice), DMF, 2% DIPEA in DMF (v/v) (twice), and finally DMF. After draining the last rinse, the swollen resin was suspended in DMF to prepare for the loading.

Activation of the DBCO-amine. To the freebase DBCO-amine oil (4.2 mmol) was added dichloromethane (10 mL/g, 16.4 mL), and a magnetic stir bar, and the solution was cooled in a 0° C. ice bath. Upon equilibrating to temperature, DIPEA (1.1 eq, 0.80 mL, 4.6 mmol) was added, followed by 4-nitrophenyl chloroformate (1.0 eq, 0.88 g, 4.2 mmol) in one portion. The solution turned yellow immediately. Activation was verified by HPLC, to observe the 4-nitrophenyl carbonate intermediate.

Loading of the DBCO-amine. To the solution of activated DBCO-amine, was added 4-dimethylaminopyridine (0.10 eq, 0.052 g, 0.42 mmol). The amino-PEG resin, which had been washed and suspended in DMF, was agitated by nitrogen bubbling. The activated DBCO-amine solution was added directly to the resin, and the solution was allowed to mix overnight with nitrogen bubbling for agitation.

After agitation overnight, HPLC showed complete consumption of the 4-nitrophenyl carbonate intermediate. The solvent was drained from the resin through the frit with vacuum, and the resin was washed with DMF, DCM, and DMF. Then, an acetate capping solution was prepared in an Erlenmeyer flask by the addition of DMF (66 mL), DIPEA (22 mL, 126 mmol), and acetic anhydride (12 mL, 127 mmol). The resin was suspended in minimal DMF, and the capping solution was added in one portion, and allowed to mix with nitrogen agitation for 30 minutes. Then, the capping solution was drained, and the catch resin was washed extensively with DMF, then DCM, and finally MTBE. The catch resin was dried on vacuum with a slow nitrogen bleed for 16 hours. The mass of catch resin after drying was 15.30 grams. The catch resin loading was quantified following the general procedure above.

General LC-MS and HRMS Methods

Methods for LC-MS analysis: Waters CORTECS C18 (2.7 mm, 4.6×150 mm) analytical column using mobile phase water-acetonitrile with 0.05% TFA (v/v) modifier, with a flow rate 1.3 mL/min, 60° C. column oven temperature, and monitoring at 220 nm wavelength. ESI-MS was used for peptide characterization.

The solvent gradient was as follows:

| time | % water (v/v) | % acetonitrile (v/v) |
|---|---|---|
| 0 min | 95% | 5% |
| 3 min | 72.5% | 27.5% |
| 17 min | 45.5% | 54.5% |
| 19 min | 5% | 95% |
| 20 min | 5% | 95% |

The HRMS analysis was performed on all of the final macrocyclic peptides on an LTQ Orbitrap mass spectrometer (positive electrospray ionization, 4.5 kV) in line with UPLC, which allowed collection of molecular ion data with accuracy of <5 ppm.

General Procedure for SPPS

Linear peptides were assembled on a 100 mmole scale by standard Fmoc chemistry using HATU/NMM systems on an automated peptide synthesizer (Symphony® X, Protein Technologies). Rink amide AM resin with 0.54 mmol/g loading was used. The concentrations of reagents were as follows: 0.075 M Fmoc-protected amino acid (delivered 2 mL), 0.15 M HATU (delivered 1 mL), and 0.15 M NMM (delivered 2 mL) in DMF. Coupling time was adopted to 20 min across all couplings. Double coupling was performed for hindered, unnatural, and N-methylated amino acids. The couplings were followed by double treatment with $Ac_2O$-DIPEA with 5 mL, 10 to 2 ratio in DMF for 10 min. Fmoc deprotections were carried out as double treatments with 20% piperidine in IMF (5 ml) for 5 min. After each coupling and deprotection step, the resin was washed with DMF (5 mL, 5×30 sec).

General Procedure for Chloroacetate and Cap D Capping

Swelling of the Fmoc-protected peptide-bound resin was conducted as pre-treatment with DMF (3×10 min). After draining of DMF, the Fmoc group was deprotected by adding 20% piperidine in DMF solution (2×4 mL, 5 min each). The solution was drained and the resin was washed with DMF-DCM sequentially (5×4 mL).

Chloroacetate capping on a 25-umole scale: in two separate vials were weighed chloroacetic acid (24 mg, 0.25 mmol) and DIC (32 mg, 0.25 mmol). Each compound was dissolved in 1 mL of DMF. The two solutions were mixed for 1 min and immediately added to the Fmoc-deprotected resin and then bubbled with nitrogen for 1 h. After which, the solution was drained and the resin was washed sequentially with DMF-DCM (5×4 mL), and finally with diethyl ether to dry the resin.

Cap D peptide capping on a 75-umole scale: In three separate vials were weighed Cap D (71 mg, 0.23 mmol), HATU (86 mg, 0.23 mmol), and DIPEA (30 mg, 0.23 mmol). Each compound was dissolved in 700 mL of DMF. To the Fmoc-deprotected resin was added sequentially DIPEA, Cap D, and finally HATU. The solution was bubbled with nitrogen for 1 h. After which, the solution was drained and the resin was washed sequentially with DMF-DCM (5×4 mL), and finally with diethyl ether to dry the resin.

General Procedure for Cleavage of the Capped Linear Peptide

To the dry resin (~120 mg), was added 3 mL of the cleavage cocktail: 97% TFA, 2.5% TIS, 0.5% DTT. Resins were stirred for 1 h at room temperature. After which, the resin was filtered and the solution was dripped into 30 mL of cold diethyl ether. Peptide was precipitated as white solids. The mixture was centrifuged (5 min, 3000 rpm, 0° C.), decanted and the remaining peptide pellet was washed twice with 15 mL of cold ether as described above. The crude peptide was dissolved in 10-20% water-acetonitrile, and a sample solution was injected in LCMS for analysis of the corresponding linear peptide. The above water-acetonitrile solution was then lyophilized overnight and the weight of the obtained linear peptide was recorded and the ratio of the obtained peptide (mg) vs. the Fmoc resin (mg) was calculated.

General Procedure for Solution Phase Cyclization of Linear Peptides

With MeOH as the solvent: The lyophilized peptide (20-30 mg) was dissolved in MeOH (4.5 mL) in a scintillation vial. Then a solution of 0.2 M $NH_4OAc$—$NH_3$ (pH=9.3, 4.5 mL) was added slowly to the MeOH solution. For the cyclizations with nucleophilic sulfur, mixture was stirred at room temperature for 12-18 h. For the cyclizations with nucleophilic amine, mixture was stirred at 72° C. for 12-18 h. The reaction mixture was transferred into a specific volumetric flask, the vial was washed, the solutions were combined and diluted with MeOH to the desired volume. The resulting solution was directly injected in LCMS for analysis of area under curve (AUC) and area percent (AP) values.

With DMF as the solvent: The lyophilized peptide (20-30 mg) was dissolved in DMF (4.5 mL) in a scintillation vial. Then a solution of 0.2 M DIPEA (pH=11, 4.5 mL) was added slowly to the DMF solution. For the cyclizations with nucleophilic sulfur, the mixture was stirred at room temperature for 12-18 h. For the cyclizations with nucleophilic amine, the mixture was stirred at 72° C. for 12-18 h. The solvent was removed using Genevac and the peptide residue was redissolved in MeOH. The solution was transferred into a specific volumetric flask, the vial was washed, and the solutions were combined and diluted with MeOH to the desired volume. The resulting solution was directly injected in LCMS for analysis of area under curve (AUC) and area percent (AP) values.

Optimized Procedure for Catch-Release Purification of Crude Linear Peptides

Catch of the linear peptide. A fresh stock solution of 0.5% DTT and 10% acetic acid in MeOH was prepared. In a 12-ml syringe equipped with a polypropylene frit, the anchored strained cyclooctyne resin (DBCO)—catch resin D—(200-250 mg, loading 0.16 mmol/g, 4 eq respect to the crude peptide) was weighed and swelled with DCM for 30 min. The solution was drained. The lyophilized peptide (20-30 mg) was dissolved in 250 mL of MeOH and sonicated. The resin was suspended in 750 mL of the stock solution. The above peptide solution was added slowly to the resin suspension. The peptide vial was washed twice with 250 mL of the stock solution and added to the resin. Final concentration of the peptide was in the range of 10-13 mg/mL. The resulting mixture was stirred at room temperature for 3-5 h and monitored by LCMS to confirm the completion of the reaction. For more diluted reactions, click reaction was slow and was allowed to proceed 18 h.

After the click reaction was completed, the solution was drained and the resin was washed with the stock solution (3×4 mL). The resin was suspended in the stock solution (1 mL) and the excess alkyne catch resin D was quenched with 20 mL of benzyl azide for 30 min. The solution was drained and the resin was washed successively with the stock solution (5×4 mL), then MeOH (2×4 mL).

Macrocyclization release of the peptide macrocycle. The resin was suspended in MeOH (4.5 mL), then a solution of 0.2 M $NH_4OAc$—$NH_3$ in MeOH (4.5 mL) was added. For the cyclizations with nucleophilic sulfur, the reaction mixture was stirred at room temperature for 18 h. For the cyclizations with nucleophilic amines, the reaction mixture was stirred at 40° C. for 18 h. Then the resin was filtered and the solution was collected in a 100-ml round-bottomed flask. The resin was washed with 0.1 M $NH_4OAc$—$NH_3$ solution in MeOH (7×5 mL), then MeOH (2×2 mL), and finally 50% acetonitrile-water (2×2 mL). The solvents were reduced using a rotavap at 23° C. and the peptide residue was re-dissolved in MeOH. The resulting solution was transferred into a volumetric flask (if performing a head-to-head comparison with the solution phase reaction, then the same size as that was used in the solution phase cyclization), and diluted to the desired volume. The solution was directly injected in LCMS for further analysis and direct comparison with chloroacetate solution phase cyclization.

Since the injection and final dilution volumes are the same for the chloroacetate solution cyclization and catch-release protocol, the recovery ratio of cyclized product was calculated for each sample using the following equation:

$$\text{Recovery} = \left(\frac{AUC_{CR} \times P_{CR}}{R_{CR} \times S_{CR}}\right) \div \left(\frac{AUC_{Cl} \times P_{Cl}}{R_{Cl} \times S_{Cl}}\right)$$

AUC=HPLC area under the curve
R: mg Fmoc resin that was capped
S: mg peptide for each experiment
P: total mg peptide obtained after cleavage
Subscript CR denote values for the catch-release experiment
Subscript Cl denote values for the chloroacetate experiment The efficiency of the catch-release method for macrocycle purification was demonstrated by a head-to-head comparison of the catch-release method with the chloroacetate cyclization (Table 1). Peptide $CM_{11}$-1 (Entry 10, table 1) was chosen as the model peptide. The library was generated with the goal of producing peptide macrocycles from 5 to 20 amino acids in size, to evaluate the robustness of the protocol with respect to macrocycle size. Shorter peptide sequences (Entries 1-8) were designed by sequential deletion of the amino acids in $CM_{11}$-1 proceeding the C-terminal downstream Cys, while longer sequences were designed by sequential addition of amino acids following the $^{Me}$Ala (Entries 11-17). The library was synthesized on a multichannel peptide synthesizer with acetic anhydride capping after each coupling to reduce single-site deletion sequence impurities. The sidechain-protected peptide on resin was then either capped with chloroacetic acid or Cap D at the N-terminus for direct comparison of macrocyclization protocols. The peptides were then subjected to macrocyclization and release under the optimized protocols, and the resulting solutions were analyzed by quantitative HPLC for the relative macrocycle concentration. The relative HPLC area (macrocycle "recovery") serves as a useful surrogate for "yield" of the catch-release method.

TABLE 1

A head-to-head comparison of the optimized catch-release method with chloroacetate cyclization for direct comparison of purity and relative macrocycle recovery.

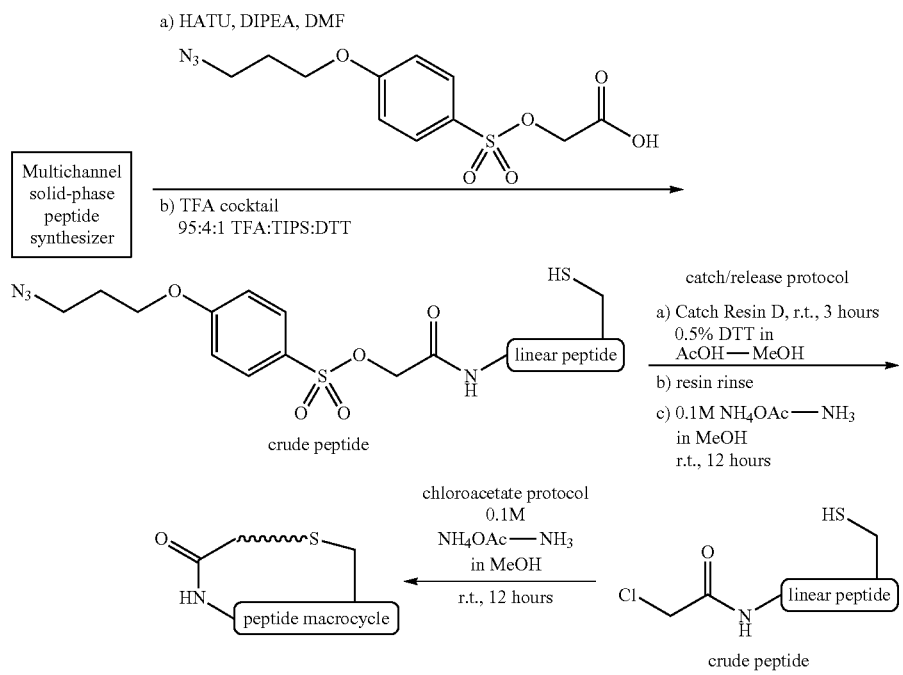

| Entry | Linear Peptide Sequence | Ring Size (in amino acids) | Relative Recovery (%, CR/Cl)[a] | Chloroacetate Macrocycle Purity (%)[b] | Catch-Release (CR) Macrocycle Purity (%)[b] |
|---|---|---|---|---|---|
| 1 | dW$^{Me}$ADVCG (SEQ ID NO: 26) | 5 | 83 | 89 | 95 |
| 2 | dW$^{Me}$ADV$^{Me}$SCG (SEQ ID NO: 27) | 6 | 66 | 49 | 88 |
| 3 | dW$^{Me}$ADV$^{Me}$SGCG (SEQ ID NO: 28) | 7 | N/O | 70 | 88 |
| 4 | dW$^{Me}$ADV$^{Me}$SGRCG (SEQ ID NO: 29) | 8 | 98 | 64 | 91 |
| 5 | dW$^{Me}$ADV$^{Me}$SGR$^{Me}$FCG (SEQ ID NO: 30) | 9 | 146 | 17 | 80 |
| 6 | dW$^{Me}$ADV$^{Me}$SGR$^{Me}$F$^{Me}$GCG (SEQ ID NO: 31) | 10 | 64 | 30 | 78 |
| 7 | dW$^{Me}$ADV$^{Me}$SGR$^{Me}$F$^{Me}$GYCG (SEQ ID NO: 32) | 11 | 72 | 20 | 69 |
| 8 | dW$^{Me}$ADV$^{Me}$SGR$^{Me}$F$^{Me}$GY$^{Me}$FCG (SEQ ID NO: 33) | 12 | 105 | 7 | 69 |
| 9 | dW$^{Me}$ADV$^{Me}$SGR$^{Me}$F$^{Me}$GY$^{Me}$FPCG (SEQ ID NO: 34) | 13 | 50 | 13 | 61 |
| 10 | dWCDV$^{Me}$SGR$^{Me}$F$^{Me}$GY$^{Me}$FPCG (SEQ ID NO: 35) | 13 | 28 | 12 | 91 |
| 11 | dWP$^{Me}$ADV$^{Me}$SGR$^{Me}$F$^{Me}$GY$^{Me}$FPCG (SEQ ID NO: 36) | 14 | 33 | 6 | 60 |
| 12 | dWDP$^{Me}$ADV$^{Me}$SGR$^{Me}$F$^{Me}$GY$^{Me}$FPCG (SEQ ID NO: 37) | 15 | 74 | 8 | 81 |
| 13 | dWGDP$^{Me}$ADV$^{Me}$SGR$^{Me}$F$^{Me}$GY$^{Me}$FPCG (SEQ ID NO: 38) | 16 | 51 | 7 | 74 |
| 14 | dW$^{Me}$SGDP$^{Me}$ADV$^{Me}$SGR$^{Me}$F$^{Me}$GY$^{Me}$FPCG (SEQ ID NO: 39) | 17 | 29 | 6 | 70 |
| 15 | dW D$^{Me}$SGDP$^{Me}$ADV$^{Me}$SGR$^{Me}$F$^{Me}$GY$^{Me}$FPCG (SEQ ID NO: 40) | 18 | 50 | 5 | 75 |

TABLE 1-continued

A head-to-head comparison of the optimized catch-release method with chloroacetate cyclization for direct comparison of purity and relative macrocycle recovery.

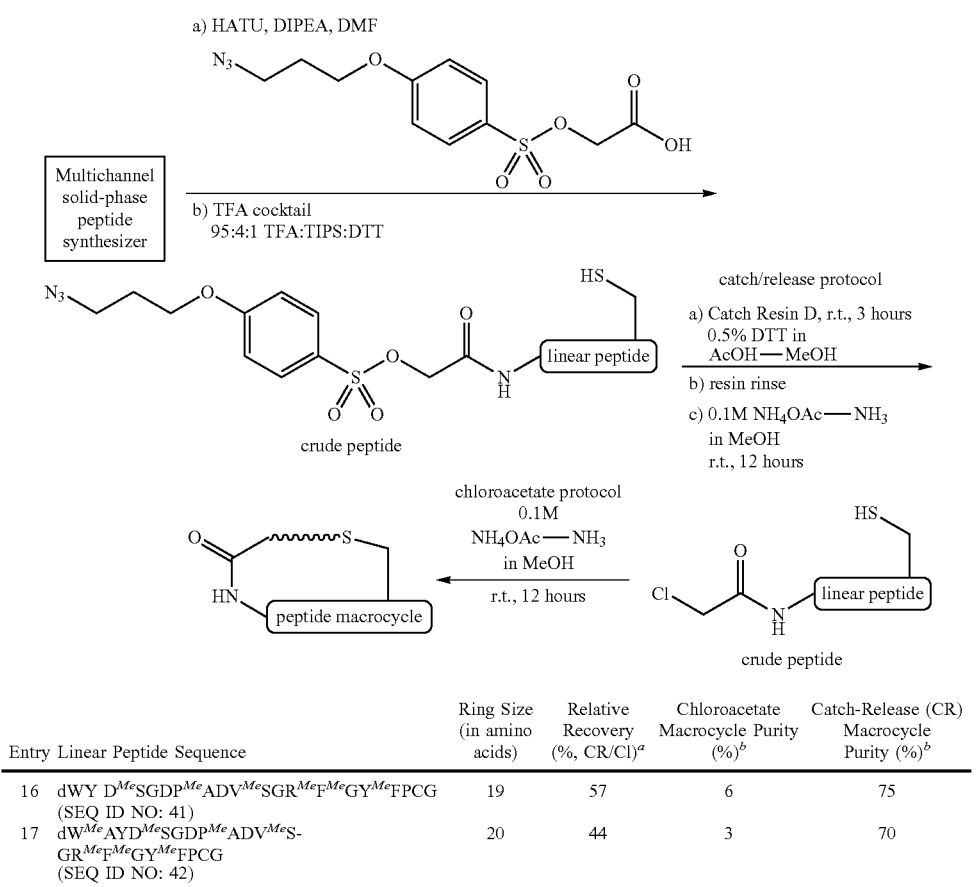

| Entry | Linear Peptide Sequence | Ring Size (in amino acids) | Relative Recovery (%, CR/Cl)[a] | Chloroacetate Macrocycle Purity (%)[b] | Catch-Release (CR) Macrocycle Purity (%)[b] |
|---|---|---|---|---|---|
| 16 | dWY D$^{Me}$SGDP$^{Me}$ADV$^{Me}$SGR$^{Me}$F$^{Me}$GY$^{Me}$FPCG (SEQ ID NO: 41) | 19 | 57 | 6 | 75 |
| 17 | dW$^{Me}$AYD$^{Me}$SGDP$^{Me}$ADV$^{Me}$S-GR$^{Me}$F$^{Me}$GY$^{Me}$FPCG (SEQ ID NO: 42) | 20 | 44 | 3 | 70 |

[a]The recovery of the catch-release process is analogous to the yield, and was determined by quantitative HPLC analysis of the relative macrocycle concentration in the resulting solutions.
[b]Purity was determined by HPLC area percent.
$^{Me}$AA: N-methylated amino acids;
dAA: D-amino acids Automation of the catch-release method was also demonstrated. A twelve member library of the thioether cyclic peptides based on G7-18NATE (Ambaye, N. D. et al. Uptake of a Cell Permeable G7-18NATE Construct Into Cells and Binding With the Grb7-SH2 Domain. *Biopolymers* 2011, 96, 181-188) was generated as shown in Table 4. The "cleavage" functionality of a multichannel peptide synthesizer was used to demonstrate the catch-release method in an automated high-throughput setting. Catch resin D (DBCO) was loaded into the reaction vessels. The extra amino acid positions of the peptide synthesizer were used to hold a solution of the linear peptide in 9:1 MeOH:AcOH with 0.5% DTT, and used the basic "release solution" (0.1M NH$_4$OAc/NH$_3$ in MeOH) in the cleavage solution reservoir. In this fashion, the instrument was programmed for consistent and reproducible peptide and solvent delivery, with automated macrocyclization release and collection of the final cyclized product in the cleavage vessels. The workflow is depicted visually in FIG. 3. The complete peptide synthesis program is shown in Tables 2 and 3.

TABLE 2

The automated synthesis program to swell the resin prior to delivering the peptide.

| Step | Operation | RV/PV | Bottle | Vol. (μL) | Mix type | Time (HH:MM:SS) | temp. (° C.) | Drain | Repitions |
|---|---|---|---|---|---|---|---|---|---|
| 1 | Bottom Delivery | RV | MeOH | 5000 | | 00:00:00 | | No | 1 |
| 2 | Mix | RV | | | N2 | 00:10:00 | 25 | Yes | |
| 3 | Bottom Delivery | RV | MeOH | 5000 | | 00:00:00 | | No | 1 |

TABLE 2-continued

The automated synthesis program to swell the resin prior to delivering the peptide.

| Step | Operation | RV/PV | Bottle | Vol. (µL) | Mix type | Time (HH:MM:SS) | temp. (° C.) | Drain | Repitions |
|---|---|---|---|---|---|---|---|---|---|
| 4 | Mix | RV | | | N2 | 00:10:00 | 25 | Yes | |
| 5 | Bottom Delivery | RV | MeOH | 5000 | | 00:00:00 | | No | 1 |
| 6 | Mix | RV | | | N2 | 00:10:00 | 25 | Yes | |

TABLE 3

The automated synthesis program for the delivery of the peptide and the catch-release.

| Step | Operation | RV/PV | Bottle | Vol. (µL) | Mix type | Time (HH:MM:SS) | Temp (° C.) | Drain | Rep |
|---|---|---|---|---|---|---|---|---|---|
| 1 | AA Delivery | RV | Cycle AA | 5000 | N2 | 03:00:00 | 25 | No | 1 |
| 2 | Pause | | | | | | | | |
| 3 | Drain Dry | RV | | | | 00:00:30 | | | |
| 4 | Vent Wash | RV | DMF | | | | | | 5 |
| 5 | Top Delivery | RV | DMF | 5000 | N2 | 00:00:30 | 25 | Yes | 3 |
| 6 | Drain Dry | RV | | | | 00:00:30 | | | |
| 7 | Bottom Delivery | RV | MeOH | 10000 | | 00:00:00 | | No | 1 |
| 8 | Mix | RV | | | N2 | 00:00:30 | 25 | Yes | |
| 9 | Bottom Delivery | RV | MeOH | 10000 | | 00:00:00 | | No | 1 |
| 10 | Mix | RV | | | N2 | 00:00:30 | 25 | Yes | |
| 11 | Bottom Delivery | RV | MeOH | 10000 | | 00:00:00 | | No | 1 |
| 12 | Mix | RV | | | N2 | 00:00:30 | 25 | Yes | |
| 13 | Top Delivery | RV | 1 | 5000 | N2 | 00:30:00 | 25 | Yes | 1 |
| 14 | Vent Wash | RV | DMF | | | | | | 5 |
| 15 | Top Delivery | RV | DMF | 5000 | N2 | 00:00:30 | 25 | Yes | 5 |
| 16 | Drain Dry | RV | | | | 00:05:00 | | | |
| 17 | Bottom Delivery | RV | MeOH | 10000 | | 00:00:00 | | No | 1 |
| 18 | Mix | RV | | | N2 | 00:00:30 | 25 | Yes | |
| 19 | Bottom Delivery | RV | MeOH | 10000 | | 00:00:00 | | No | 1 |
| 20 | Mix | RV | | | N2 | 00:00:30 | 25 | Yes | |
| 21 | Bottom Delivery | RV | MeOH | 10000 | | 00:00:00 | | No | 1 |
| 22 | Mix | RV | | | N2 | 00:00:30 | 25 | Yes | |
| 23 | Bottom Delivery | RV | MeOH | 10000 | | 00:00:00 | | No | 1 |
| 24 | Mix | RV | | | N2 | 00:00:30 | 25 | Yes | |
| 25 | Bottom Delivery | RV | MeOH | 10000 | | 00:00:00 | | No | 1 |
| 26 | Mix | RV | | | N2 | 00:00:30 | 25 | Yes | |
| 27 | Bottom Delivery | RV | BMeOH | 5000 | | 01:00:00 | | No | 1 |
| 28 | Collect | RV | | | | | | | |
| 29 | Bottom Delivery | RV | BMeOH | 5000 | | 02:00:00 | | No | 1 |
| 30 | Collect | RV | | | | | | | |
| 31 | Bottom Delivery | RV | BMeOH | 5000 | | 03:00:00 | | No | 1 |
| 32 | Collect | RV | | | | | | | |
| 33 | Bottom Delivery | RV | BMeOH | 5000 | | 04:00:00 | | No | 1 |
| 34 | Collect | RV | | | | | | | |
| 35 | Bottom Delivery | RV | MeOH | 5000 | | 00:02:00 | | No | 1 |
| 36 | Collect | RV | | | | | | | |
| 37 | Bottom Delivery | RV | MeOH | 2500 | | 00:02:00 | | No | 1 |
| 38 | Collect | RV | | | | | | | |
| 39 | Bottom Delivery | RV | MeOH | 2500 | | 00:02:00 | | No | 1 |
| 40 | Collect | RV | | | | | | | |
| 41 | Bottom Delivery | RV | MeOH | 2500 | | 00:02:00 | | No | 1 |
| 42 | Collect | RV | | | | | | | |

The model peptide library, composed of sequences 5-16 amino acids in length, was delivered by the peptide synthesizer onto the catch resin D, followed by a programmed delay for the catch click reaction to proceed. This automation protocol includes nitrogen sparging for mixing, and effective peptide immobilization was achieved as monitored by LCMS. The instrument was programmed to drain the peptide solution, wash the resin with MeOH, quench the excess catch resin with 0.1 M benzyl azide, and then deliver the basic "release" solution and collect the macrocyclic peptide solution in the cleavage vessels. The results of this high-throughput automation on the representative library are summarized in Table 4. While the HPLC purity of the linear peptides ranged from 8-72% purity, the subsequent automated catch-release protocol produced cyclic peptides with purities higher than 92% for all sequences, a purity level generally acceptable for direct evaluation of activity in a biological assay without further purification.

TABLE 4

Automation of the optimized catch-release protocol on a multichannel peptide synthesizer

| Entry | Linear Peptide Sequence | Linear Purity[a] (%) | Macrocycle Purity[a] (%) |
|---|---|---|---|
| 1 | FVE[Me]GCG (SEQ ID NO: 1) | 72 | 93 |
| 2 | FVE[Me]GYCG (SEQ ID NO: 2) | 62 | 98 |
| 3 | FVE[Me]GY[Me]FCG (SEQ ID NO: 3) | 64 | 92 |
| 4 | FVE[Me]GY[Me]F[Me]GCG (SEQ ID NO: 4) | 62 | 97 |
| 5 | FVE[Me]GY[Me]F[Me]GTCG (SEQ ID NO: 5) | 60 | 96 |
| 6 | FVE[Me]GY[Me]F[Me]GT[Me]FCG (SEQ ID NO: 6) | 12 | 96 |
| 7 | FVE[Me]GY[Me]F[Me]GT[Me]FPCG (SEQ ID NO: 7) | 31 | 92 |
| 8 | FVE[Me]GY[Me]F[Me]GWT[Me]FPCG (SEQ ID NO: 8) | 12 | 96 |
| 9 | FVE[Me]GY[Me]F[Me]GRWT[Me]FPCG (SEQ ID NO: 9) | 18 | 98 |
| 10 | FVE[Me]GY[Me]F[Me]GRAWT[Me]FPCG (SEQ ID NO: 10) | 8 | 97 |
| 11 | FVE[Me]GY[Me]F[Me]GRAYWT[Me]FPCG (SEQ ID NO: 11) | 11 | 93 |
| 12 | FVE[Me]GY[Me]F[Me]GRNAYWT[Me]FPCG (SEQ ID NO: 12) | 8 | 95 |

[a]Purity by HPLC area percent.
[Me]AA: N-methylated amino acids

In both the alternate macrocyclization pathways, the side products were analyzed by LC-MS/MS. In the latter case, the side products were N-terminal glycolates with intersequence Asp(OMe), presumably formed via a two-step mechanism of Asp-macrocyclization and macrolactone opening by methanol. In larger ring-sized macrocycles with 13 to 17 amino acids (entries 11-15), the product purity obtained from the catch-release protocol was dramatically higher than the chloroacetate macrocyclization, whereas, in the chloroacetate protocol, it became difficult to discern the product from the complex reaction mixture. In this sense, the solid-phase assisted purification was observed to be an enabling technology for the synthesis of backbone amine peptide macrocycles.

TABLE 5

Extension of the catch-release protocol to nitrogen-based nucleophilic macrocyclization to form backbone secondary amine macrocycles.

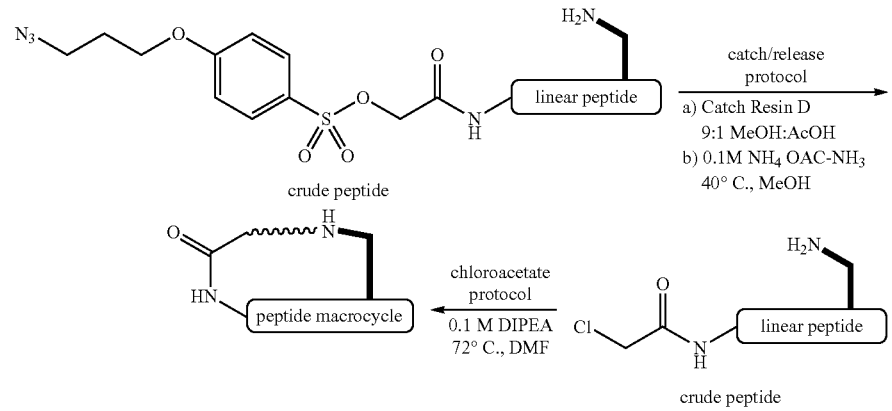

| Entry | Linear Peptide Sequence | Ring Size (in amino acids) | Recovery (CR/Cl, %)[a] | Chloroacetate Macrocycle Purity (%)[b] | Catch-Release (CR) Macrocycle Purity (%)[b] |
|---|---|---|---|---|---|
| 1 | [Me]GY[Me]FPDapG (SEQ ID NO: 13) | 5 | 46 | 70 | 96 |
| 2 | [Me]F[Me]GY[Me]FPDapG (SEQ ID NO: 14) | 6 | 87 | 49 | 93 |

TABLE 5-continued

Extension of the catch-release protocol to nitrogen-based nucleophilic macrocyclization to form backbone secondary amine macrocycles.

| Entry | Linear Peptide Sequence | Ring Size (in amino acids) | Recovery (CR/Cl, %)[a] | Chloroacetate Macrocycle Purity (%)[b] | Catch-Release (CR) Macrocycle Purity (%)[b] |
|---|---|---|---|---|---|
| 3 | K(Alloc)$^{Me}$F$^{Me}$GY$^{Me}$FPDapG (SEQ ID NO: 15) | 7 | 30 | 8 | >98 |
| 4 | GK(Alloc)$^{Me}$F$^{Me}$GY$^{Me}$FPDapG (SEQ ID NO: 16) | 8 | 47 | 5 | >98 |
| 5 | SGK(Alloc)$^{Me}$F$^{Me}$GY$^{Me}$FPDapG (SEQ ID NO: 17) | 9 | 58 | 6 | 86 |
| 6 | VSGK(Alloc)$^{Me}$F$^{Me}$GY$^{Me}$FPDapG (SEQ ID NO: 18) | 10 | 71 | 6 | 76 |
| 7 | $^{Me}$ADVSGK(Alloc)$^{Me}$F$^{Me}$GY$^{Me}$FPDapG (SEQ ID NO: 19) | 12 | 87 | 6 | 55 |
| 8 | dW$^{Me}$AYVSGK(Alloc)$^{Me}$F$^{Me}$GY$^{Me}$FPDapG (SEQ ID NO: 43) | 13 | 86 | 17 | 68 |
| 9 | dW$^{Me}$ADVSGR$^{Me}$F$^{Me}$GY$^{Me}$FPDapG (SEQ ID NO: 44) | 13 | 232 | 7 | 87 |
| 10 | F$^{Me}$AYVSGK(Alloc)$^{Me}$F$^{Me}$GY$^{Me}$FPDapG (SEQ ID NO: 20) | 13 | 54 | 5 | 76 |
| 11 | F$^{Me}$AYVSGR$^{Me}$F$^{Me}$GY$^{Me}$FPDapG (SEQ ID NO: 21) | 13 | 40 | 7 | >98 |
| 12 | FP$^{Me}$AYVSGK(Alloc)$^{Me}$F$^{Me}$GY$^{Me}$FPDapG (SEQ ID NO: 22) | 14 | 60 | <5 | >98 |
| 13 | F$^{Me}$GP$^{Me}$AYVSGK(Alloc)$^{Me}$F$^{Me}$GY$^{Me}$FPDapG (SEQ ID NO: 23) | 15 | 37 | <5 | >98 |
| 14 | FL$^{Me}$GP$^{Me}$AYVSGK(Alloc)$^{Me}$F$^{Me}$GY$^{Me}$FPDapG (SEQ ID NO: 24) | 16 | 36 | <5[c] | >98 |
| 15 | FYL$^{Me}$GP$^{Me}$AYVSGK(Alloc)$^{Me}$F$^{Me}$GY$^{Me}$FPDapG (SEQ ID NO: 25) | 17 | 28 | <5 | >98 |

[a]The recovery of the catch-release process is analogous to the yield, and was determined by quantitative HPLC analysis of the relative macrocycle concentration in the resulting solutions.
[b]Purity was determined by HPLC.
[c]This experiment was done in methanol.
Alloc = allyloxycarbonyl,
Dap = 2,3-diaminopropionic acid,
$^{Me}$AA: N-methylated amino acids;
dAA: D-amino acids.

TABLE 6
Characterization data for linear and cyclized products of TABLE 1 entries.
| Capped Linear Peptide | Macrocyclization Product |
|---|---|
| Linear peptides Sequence: dW$^{Me}$ADV CG (SEQ ID NO: 45) | |
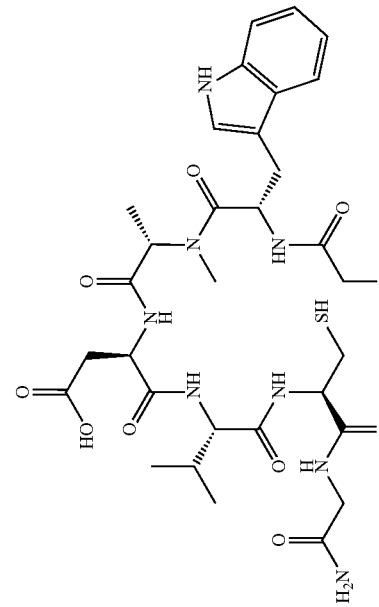
X:Cl; HPLC analysis: tR = broad peak 5.77-6.14, AP 91%.
X: OSO$_2$Ph-p-O—(CH$_2$)$_3$N$_3$; HPLC analysis: tR = broad peak 10.86-11.75, AP 83.0%.
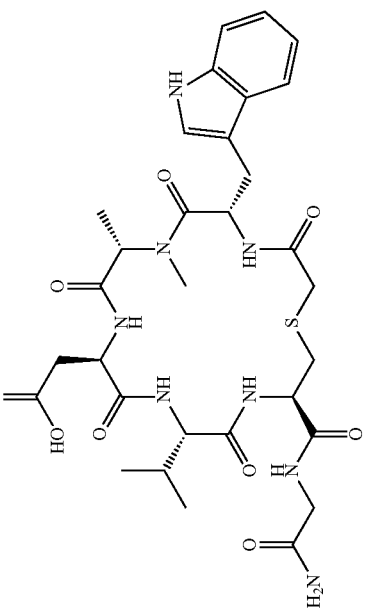
HPLC analysis: tR = 5.16 min, AP 95%.
HRMS-ESI: m/z calcd for C$_{31}$H$_{42}$O$_9$N$_8$S
(M + H)$^+$ 703.28682, found 703.28577.
1

TABLE 6-continued

Characterization data for linear and cyclized products of TABLE 1 entries.

| | Capped Linear Peptide | Macrocyclization Product |
|---|---|---|
| 2 | Linear peptides Sequence: dW $^{Me}$ADV $^{Me}$SCG (SEQ ID NO: 46) X: Cl; HPLC analysis: tR = broad peak at 5.27-5.78 min, AP 96%. X: OSO$_2$PhO—(CH$_2$)$_3$-N$_3$; HPLC analysis: tR = broad peak 10.25-11.07, AP 82.0%. | HPLC analysis: tR = 4.68 min, AP 88.0%. HRMS-ESI: m/z calcd for C$_{35}$H$_{49}$O$_{11}$N$_9$S (M + H)$^+$ 804.33450, found 804.33383. |
| 3 | Linear peptides Sequence: dW $^{Me}$ADV $^{Me}$SGCG (SEQ ID NO: 47) | HPLC analysis: tR = 4.84 min, AP 88%. HRMS-ESI: m/z calcd for C$_{37}$H$_{52}$O$_{12}$N$_{10}$S (M + H)$^+$ 861.35651, |

TABLE 6-continued

Characterization data for linear and cyclized products of TABLE 1 entries.

| | Capped Linear Peptide | Macrocyclization Product |
|---|---|---|
| 4 | <br>X:Cl; HPLC analysis: tR = 5.55 min, AP 70%.<br>X: OSO$_2$PhO—(CH$_2$)$_3$-N$_3$; HPLC analysis: broad peak tR = 9.94-10.72 min, AP 84%.<br>Linear peptides Sequence: dW $^{Me}$ADV $^{Me}$SGRCG (SEQ ID NO: 48)<br>X:Cl; HPLC analysis: tR = broad peak at 4.32-5.01 min, AP 84%.<br>X: OSO$_2$PhO—(CH$_2$)$_3$-N$_3$; HPLC analysis: tR = broad peak at 8.73-9.34 min, AP 75%. | found 861.35504.<br>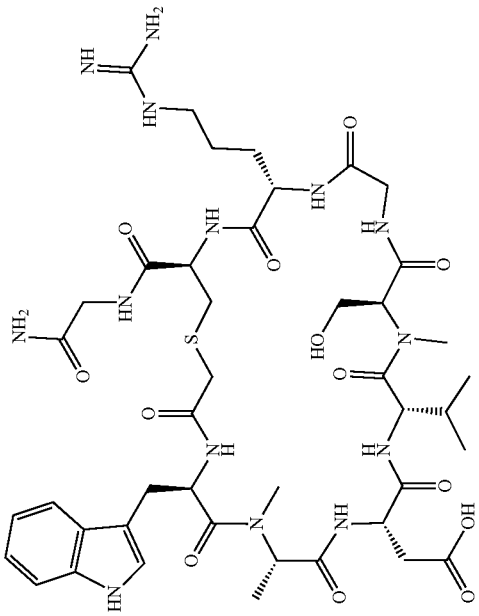<br>HPLC analysis: tR = 4.49 min, AP 91%.<br>HRMS-ESI: m/z calcd for C$_{43}$H$_{64}$O$_{13}$N$_{14}$S (M + H)$^+$ 1017.45708, found 1017.45667. |

TABLE 6-continued

Characterization data for linear and cyclized products of TABLE 1 entries.

| Capped Linear Peptide | Macrocyclization Product |
|---|---|

Linear peptides Sequence: dW $^{Me}$ADV $^{Me}$SGR $^{Me}$FCG (SEQ ID NO: 49)

5

X:Cl: HPLC analysis: tR = broad peak at 6.05-6.40 min, AP 37%.
X: OSO$_2$PhO—(CH$_2$)$_3$N$_3$; HPLC analysis: tR = 10.83 min, AP 28%.

HPLC analysis: tR = 5.71 min, AP 80.0%.
HRMS-ESI: m/z calcd for
C$_{53}$H$_{75}$O$_{14}$N$_{15}$S (M + H)$^+$ 1178.54114,
found 1178.54053.

TABLE 6-continued

Characterization data for linear and cyclized products of TABLE 1 entries.

| | Capped Linear Peptide | Macrocyclization Product |
|---|---|---|
| 6 | Linear peptides Sequence: dW $^{Me}$ADV $^{Me}$SGR$^{Me}$F$^{Me}$GCG (SEQ ID NO: 50) | |

X:Cl; HPLC analysis: tR = 6.36 min, AP 51%.
X: OSO$_2$PhO—(CH$_2$)$_3$N$_3$; HPLC analysis: tR = 10.90 min, AP 50%.

HPLC analysis: tR = 5.31 min, AP 78%.
HRMS-ESI: m/z calcd for C$_{56}$H$_{80}$O$_{15}$N$_{16}$S (M + H)$^+$ 1249.57880, found 1249.57886.

TABLE 6-continued

Characterization data for linear and cyclized products of TABLE 1 entries.

| Capped Linear Peptide | Macrocyclization Product |
|---|---|

Linear peptides Sequence: dW $^{Me}$ADV $^{Me}$SGR$^{Me}$F$^{Me}$GYCG (SEQ ID NO: 51)

7

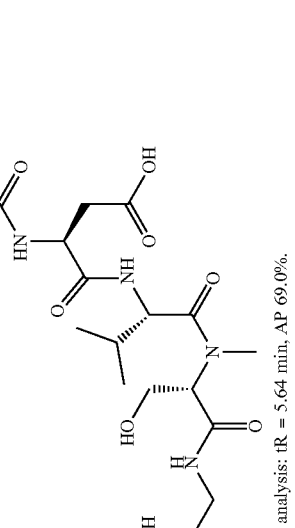

X:Cl; HPLC analysis: tR = 6.86 min, AP 29.2%.
X: OSO$_2$PhO—(CH$_2$)$_3$N$_3$; HPLC analysis: tR = 11.19 min, AP 27%.

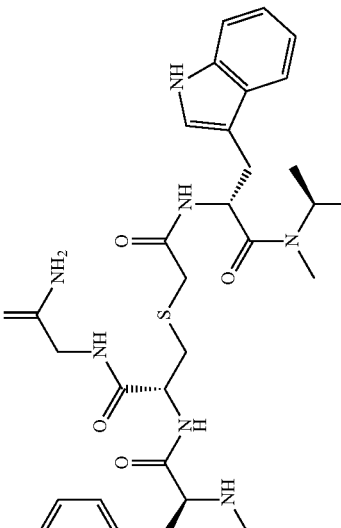

HPLC analysis: tR = 5.64 min, AP 69.0%.
HRMS-ESI: m/z calcd for C$_{65}$H$_{89}$O$_{17}$N$_{17}$S (M + H)$^+$ 1412.6400, found 1412.6411.

TABLE 6-continued

Characterization data for linear and cyclized products of TABLE 1 entries.

| | Capped Linear Peptide | Macrocyclization Product |
|---|---|---|
| | Linear peptides Sequence: dW $^{Me}$A DV $^{Me}$SGR$^{Me}$F$^{Me}$GY$^{Me}$FCG (SEQ ID NO: 52) | |
| 8 | 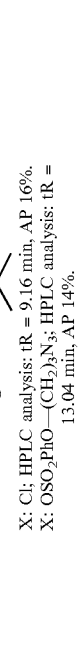<br>X: Cl; HPLC analysis: tR = 9.16 min, AP 16%.<br>X: OSO$_2$PhO—(CH$_2$)$_3$N$_3$; HPLC analysis: tR = 13.04 min, AP 14%. | 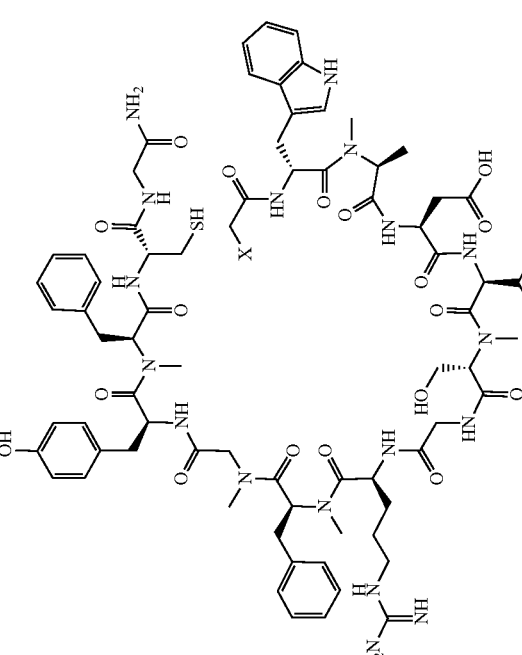<br>HPLC analysis: tR = 8.76 min, AP 69%.<br>HRMS-ESI: m/z calcd for C$_{75}$H$_{100}$O$_{18}$N$_{18}$S (M + 2H)$^{2+}$ 787.36646, found 787.36646. |

TABLE 6-continued

Characterization data for linear and cyclized products of TABLE 1 entries.

| | Capped Linear Peptide | Macrocyclization Product |
|---|---|---|
| 9 | Linear peptidesSequence: dW $^{Me}$ADV $^{Me}$SGR$^{Me}$F$^{Me}$GY$^{Me}$FPCG (SEQ ID NO: 53) | |

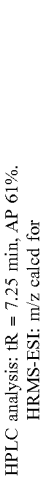

X: Cl; HPLC analysis: tR = 8.64 min, AP 13%.
X: OSO$_2$PhO—(CH$_2$)$_3$N$_3$; HPLC analysis: tR = 12.5 min, AP 13%.

HPLC analysis: tR = 7.25 min, AP 61%.
HRMS-ESI: m/z calcd for C$_{80}$H$_{107}$O$_{19}$N$_{19}$S (M + H)$^+$ 1670.77841, found 1670.76698.

TABLE 6-continued

Characterization data for linear and cyclized products of TABLE 1 entries.

| Capped Linear Peptide | Macrocyclization Product |
|---|---|

Linear peptides Sequence: dW CDV ᴹᵉSGRᴹᵉPᴹᵉGYᴹᵉFPCG (SEQ ID NO: 54)

10

X: Cl; HPLC analysis: tR = 8.50 min, AP 16%.
X: OSO₂PhO—(CH₂)₃N₃; HPLC analysis: tR = 12.38 min, AP 16%.

HPLC analysis: tR = 7.67 min, AP 91%. HRMS-ESI: m/z calcd for C₇₉H₁₀₅O₁₉N₁₉S₂ (M + H)⁺ 1688.73483, found 1688.73145.

TABLE 6-continued

Characterization data for linear and cyclized products of TABLE 1 entries.

| | Capped Linear Peptide | Macrocyclization Product |
|---|---|---|
| | Linear peptides Sequence: dWP $^{Me}$A DV $^{Me}$SGR$^{Me}$p$^{Me}$GY$^{Me}$FPCG (SEQ ID NO: 55) | |
| 11 | 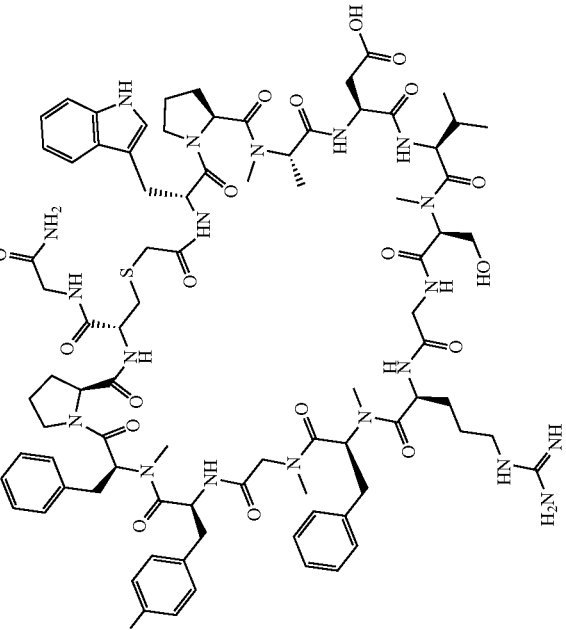 X: Cl; HPLC analysis: tR = 8.60 min, AP 7%. X: OSO$_2$PhO—(CH$_2$)$_3$N$_3$; HPLC analysis: tR = 12.34 min, AP 8%. | HPLC analysis: tR = 7.51 min, AP 60%. HRMS-ESI: m/z calcd for C$_{85}$H$_{114}$O$_{20}$N$_{20}$S (M + 2H)$^{+2}$ 884.41922, found 884.41968. |

TABLE 6-continued

Characterization data for linear and cyclized products of TABLE 1 entries.

| | Capped Linear Peptide | Macrocyclization Product |
|---|---|---|
| 12 | Linear peptides Sequence: dWDP $^{Me}$ADV $^{Me}$SGR $^{Me}$F $^{Me}$GY $^{Me}$FPCG (SEQ ID NO: 56)  X: Cl; HPLC analysis: tR = 7.83 min, AP 8%. X: OSO$_2$PhO—(CH$_2$)$_3$N$_3$; HPLC analysis: tR = 11.69 min, AP 7%. | 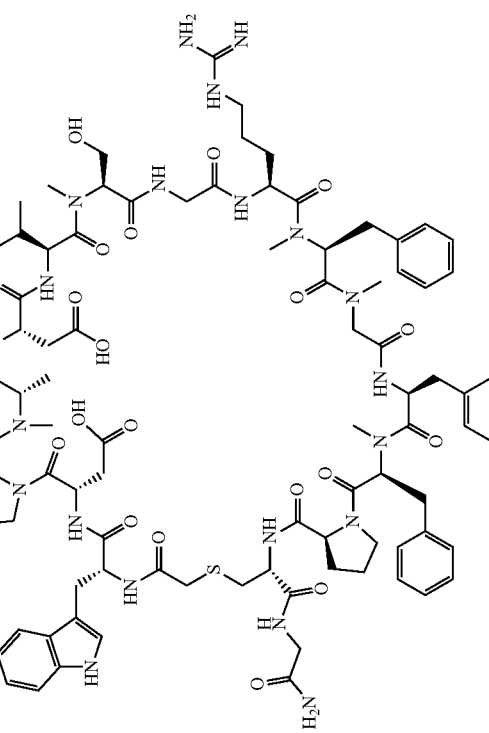 HPLC analysis: tR = 6.55 min, AP 81%. HRMS-ESI: m/z calcd for C$_{89}$H$_{119}$O$_{23}$N$_{21}$S (M + 2H)$^{+2}$ 941.93270, found 941.93335. |

TABLE 6-continued

Characterization data for linear and cyclized products of TABLE 1 entries.

| | Capped Linear Peptide | Macrocyclization Product |
|---|---|---|
| 13 | Linear peptides Sequence: dWGDP $^{Me}$ADV $^{Me}$SGR $^{Me}$P $^{Me}$eGY $^{Me}$FPCG (SEQ ID NO: 57) X: Cl; HPLC analysis: tR = 7.56 min, AP 6.0%. X: OSO$_2$PhO—(CH$_2$)$_3$N$_3$; HPLC analysis: tR = 11.37 min, AP 5%. | HPLC analysis: tR = 6.41 min, AP 74%. HRMS-ESI: m/z calcd for C$_{91}$H$_{122}$O$_{24}$N$_{22}$S (M + 2H)$^{+2}$ 970.44343, found 970.44305. |

TABLE 6-continued

Characterization data for linear and cyclized products of TABLE 1 entries.

| | Capped Linear Peptide | Macrocyclization Product |
|---|---|---|
| 14 | Linear peptides Sequence: dW $^{Me}$SGDP $^{Me}$ADV $^{Me}$SGR $^{Me}$F $^{Me}$GY $^{Me}$FPCG (SEQ ID NO: 58)<br><br>X: Cl; HPLC analysis: tR = 7.30 min, AP 5.0%.<br>X: OSO$_2$PhO—(CH$_2$)$_3$N$_3$; HPLC analysis: tR = 11.01 min, AP 5%. | HPLC analysis: tR = 6.20 min, AP 70%.<br>HRMS-ESI: m/z calcd for C$_{95}$H$_{129}$O$_{26}$N$_{23}$S (M + 2H)$^{+2}$ 1021.47118, found 1021.46765. |

TABLE 6-continued

Characterization data for linear and cyclized products of TABLE 1 entries.

| | Capped Linear Peptide | Macrocyclization Product |
|---|---|---|
| 15 | Linear peptides Sequence: dW D$^{Me}$SGDP $^{Me}$ADV $^{Me}$SGR$^{Me}$F$^{Me}$GY$^{Me}$FPCG (SEQ ID NO: 59) [structure] X: Cl; HPLC analysis: tR = 7.00 min, AP 5.0%. X: OSO$_2$PhO—(CH$_2$)$_3$N$_3$; HPLC analysis: tR = 10.69 min, AP 4%. | [structure] HPLC analysis: tR = 5.97 min, AP 75%. HRMS-ESI: m/z calcd for C$_{99}$H$_{134}$O$_{29}$N$_{24}$S (M + 2H)$^{+2}$ 1078.98465, found 1078.98315. |

TABLE 6-continued

Characterization data for linear and cyclized products of TABLE 1 entries.

| | Capped Linear Peptide | Macrocyclization Product |
|---|---|---|
| 16 | Linear peptides Sequence: dWY D$^{Me}$SGDP $^{Me}$ADV $^{Me}$SGR$^{Me}$F$^{Me}$GY$^{Me}$FPCG (SEQ ID NO: 60) <br><br> X: Cl; HPLC analysis: tR = 7.44 min, AP 5%. <br> X: OSO$_2$PhO—(CH$_2$)$_3$N$_3$; HPLC analysis: tR = 10.98 min, AP 5%. | HPLC analysis: tR = 6.43 min, AP 75%. <br> HRMS-ESI: m/z calcd for C$_{108}$H$_{143}$O$_{31}$N$_{25}$S (M + 2H)$^{+2}$ 1160.01240, found 1160.01378. |

TABLE 6-continued

Characterization data for linear and cyclized products of TABLE 1 entries.

| | Capped Linear Peptide | Macrocyclization Product |
|---|---|---|
| 17 | Linear peptides Sequence: dW $^{Me}$AY D$^{Me}$SGDP $^{Me}$ADV $^{Me}$SGR$^{Me}$F$^{Me}$GY$^{Me}$FPCG (SEQ ID NO: 61)<br>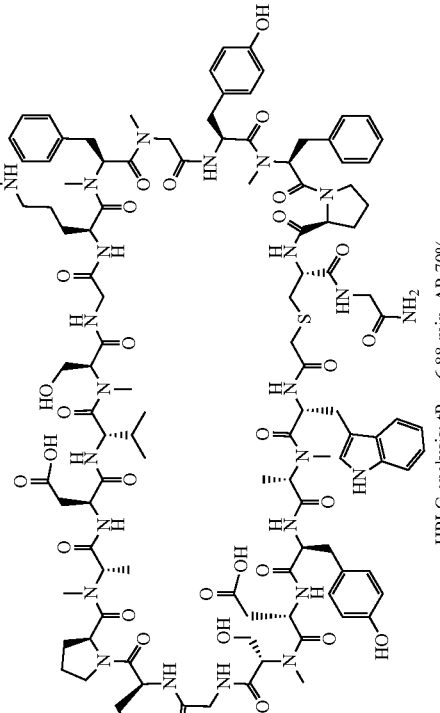<br>X: Cl; HPLC analysis: tR = 8.05 min, AP 4%.<br>X: OSO$_2$PhO—(CH$_2$)$_3$N$_3$; HPLC analysis: tR = 11.49 min, AP 4%. | 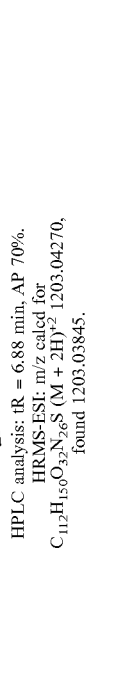<br>HPLC analysis: tR = 6.88 min, AP 70%.<br>HRMS-ESI: m/z calcd for C$_{112}$H$_{150}$O$_{32}$N$_{26}$S (M + 2H)$^{+2}$ 1203.04270, found 1203.03845. |

TABLE 7

Characterization data for linear and cyclized products of TABLE 4 entries.

| Capped Linear Peptide | Macrocyclization Product |
|---|---|
| Linear peptides Sequence: FVE$^{Me}$GCG (SEQ ID NO: 1) | |

1

Linear peptide structure with X = OSO$_2$PhO—(CH$_2$)$_3$N$_3$
HPLC analysis: tR = 10.95 min, AP 72%.

Macrocyclization product:
HPLC analysis: tR = 4.78 min, AP 93%.
HRMS-ESI: m/z calcd for C$_{29}$H$_{41}$O$_9$N$_7$S (M + H)$^+$ 664.27592, found 664.27637.

TABLE 7-continued

Characterization data for linear and cyclized products of TABLE 4 entries.

| | Capped Linear Peptide | Macrocyclization Product |
|---|---|---|
| 2 | Linear peptides Sequence: FVE$^{Me}$GYCG (SEQ ID NO: 2)<br><br>[structure of linear peptide with X: OSO$_2$PhO—(CH$_2$)$_3$N$_3$]<br><br>X: OSO$_2$PhO—(CH$_2$)$_3$N$_3$<br>HPLC analysis: tR = 11.42 min, AP 62%. | [structure of macrocyclization product]<br><br>HPLC analysis: tR = 5.71 min, AP 98%.<br>HRMS-ESI: m/z calcd for C$_{38}$H$_{50}$O$_{11}$N$_8$S (M + H)$^+$ 827.33925, found 827.33954. |

TABLE 7-continued
Characterization data for linear and cyclized products of TABLE 4 entries.
| | Capped Linear Peptide | Macrocyclization Product |
|---|---|---|
| 3 | Linear peptides Sequence: FVE$^{Me}$GY$^{Me}$FCG (SEQ ID NO: 3)<br>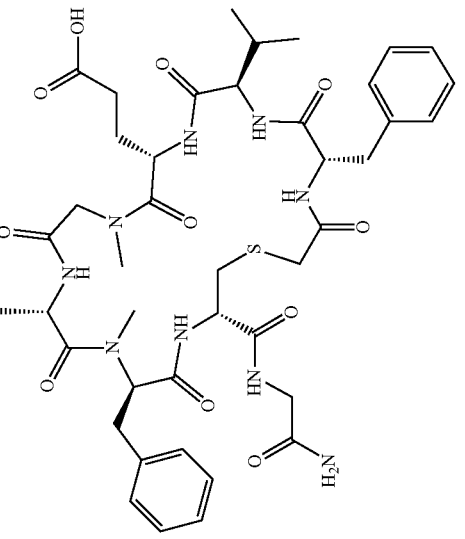<br>X: OSO$_2$PhO—(CH$_2$)$_3$N$_3$.<br>HPLC analysis: tR = 14.06 min, AP 64%. | 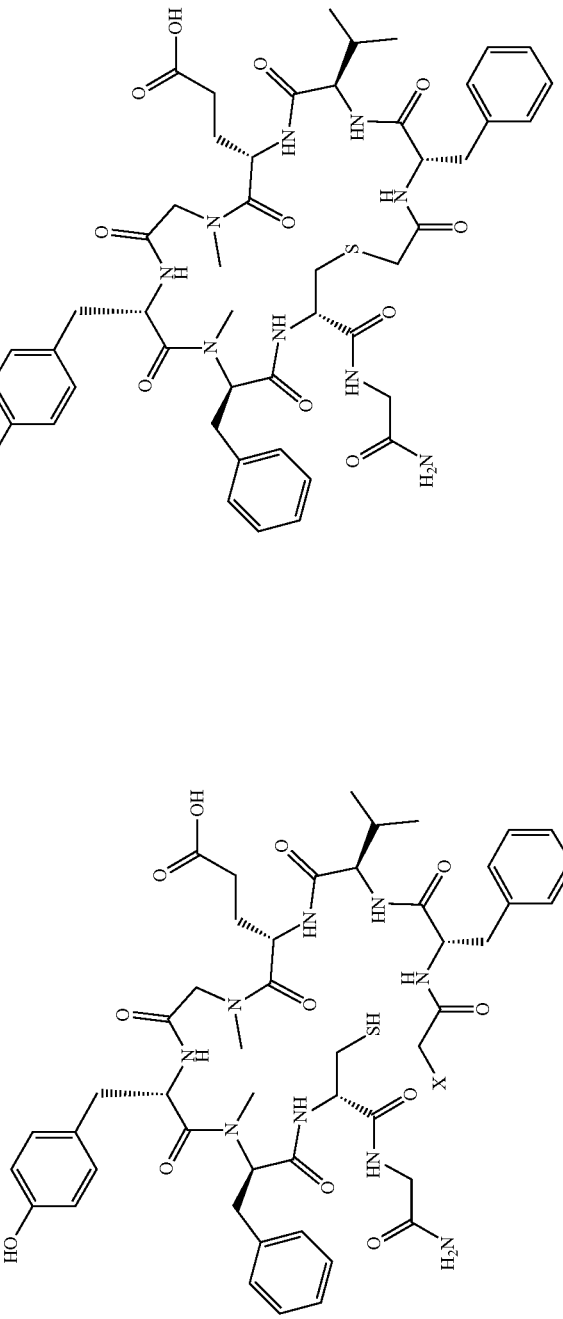<br>HPLC analysis: tR = 8.35 min, AP 92%.<br>HRMS-ESI: m/z calcd for C$_{48}$H$_{61}$O$_{12}$N$_9$S (M + H)$^+$ 988.42332, found 988.42346. |

TABLE 7-continued

Characterization data for linear and cyclized products of TABLE 4 entries.

| | Capped Linear Peptide | Macrocyclization Product |
|---|---|---|
| 4 | Linear peptides Sequence: FVE$^{Me}$GY$^{Me}$F$^{Me}$GCG (SEQ ID NO: 4)<br><br>X: OSO$_2$PhO—(CH$_2$)$_3$N$_3$<br>HPLC analysis: tR = 13.21 min, AP 62% | HPLC analysis: tR = 7.45 min, AP 97%.<br>HRMS-ESI: m/z calcd for C$_{51}$H$_{66}$O$_{13}$N$_{10}$S (M + H)$^+$ 1059.46043, found 1059.46033. |

TABLE 7-continued
Characterization data for linear and cyclized products of TABLE 4 entries.
| Capped Linear Peptide | Macrocyclization Product |
|---|---|
Linear peptides Sequence: FVE$^{Me}$GY$^{Me}$F$^{Me}$GTCG (SEQ ID NO: 5)
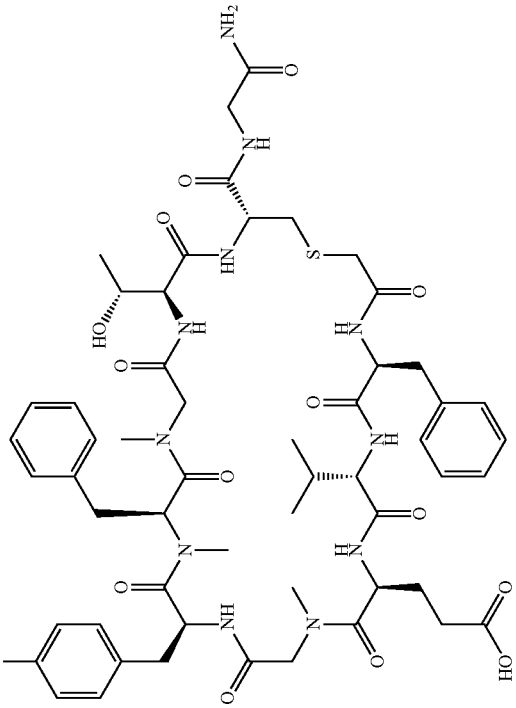
5

TABLE 7-continued
Characterization data for linear and cyclized products of TABLE 4 entries.
| | Capped Linear Peptide | Macrocyclization Product |
|---|---|---|
| 6 | Linear peptides Sequence: FVE$^{Me}$GY$^{Me}$F$^{Me}$GT$^{Me}$FCG (SEQ ID NO: 6) 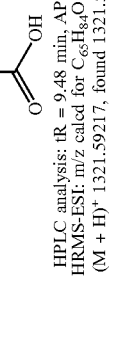 X: OSO$_2$PhO—(CH$_2$)$_3$N$_3$ HPLC analysis: tR = 14.93 min, AP 12%. | 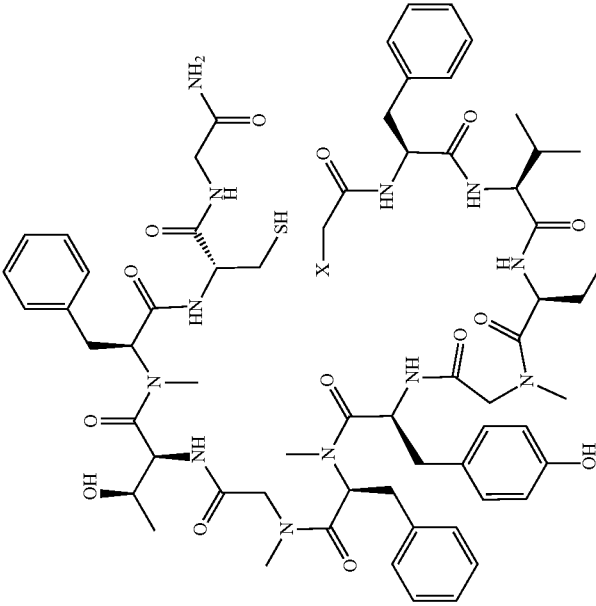 HPLC analysis: tR = 9.48 min, AP 96%. HRMS-ESI: m/z calcd for C$_{65}$H$_{84}$O$_{16}$N$_{12}$S (M + H)$^+$ 1321.59217, found 1321.59570. |

TABLE 7-continued

Characterization data for linear and cyclized products of TABLE 4 entries.

| Capped Linear Peptide | Macrocyclization Product |
|---|---|
| Linear peptides Sequence: FVE$^{Me}$GY$^{Me}$F$^{Me}$GT$^{Me}$FPCG (SEQ ID NO: 7)<br><br>X: OSO$_2$PhO—(CH$_2$)$_3$N$_3$<br>HPLC analysis: tR = 14.40 min, AP 31%. | HPLC analysis: tR = 8.52 min, AP 92.0%<br>HRMS-ESI: m/z calcd for C$_{70}$H$_{91}$O$_{17}$N$_{13}$S<br>(M + H)$^+$ 1418.64494, found 1418.64828. |

TABLE 7-continued

Characterization data for linear and cyclized products of TABLE 4 entries.

| | Capped Linear Peptide | Macrocyclization Product |
|---|---|---|
| 8 | Linear peptides Sequence: FVE^MeGY^MeF^MeGWT^MeFPCG (SEQ ID NO: 8)<br><br>X: OSO₂PhO—(CH₂)₃N₃<br>HPLC analysis: tR = 15.92 min, AP 12%. | HPLC analysis: tR = 10.85 min, AP 96%.<br>HRMS-ESI: m/z calcd for C₈₁H₁₀₁O₁₈N₁₅S<br>(M + H)⁺ 1604.72425, found 1604.72729. |

TABLE 7-continued
Characterization data for linear and cyclized products of TABLE 4 entries.
| Capped Linear Peptide | Macrocyclization Product |
|---|---|
9 Linear peptides Sequence: FVE$^{Me}$G$^{Me}$GY$^{Me}$F$^{Me}$FGRWT$^{Me}$FPCG (SEQ ID NO: 9)
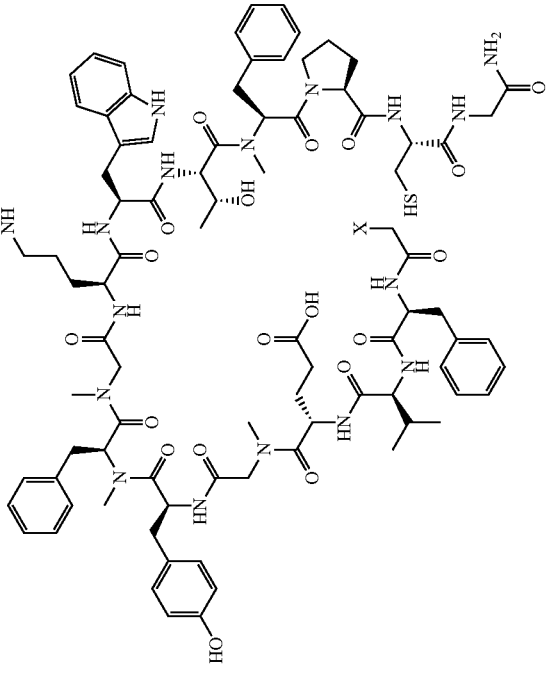
X: OSO$_2$PhO—(CH$_2$)$_3$N$_3$
HPLC analysis: tR = 13.86 min, AP 18%
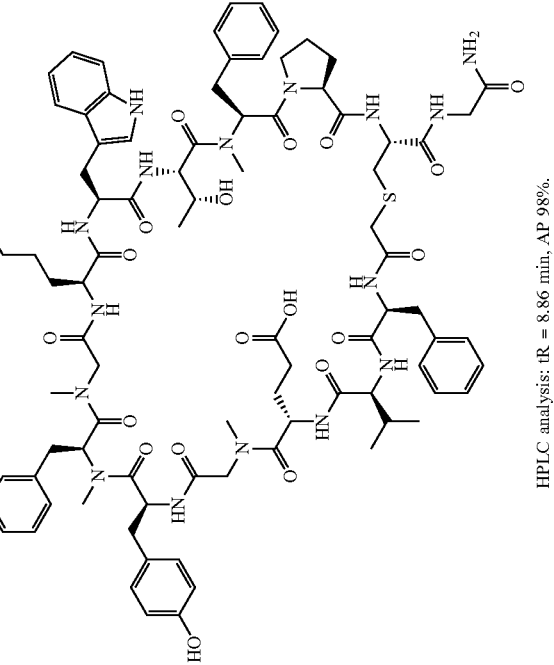
HPLC analysis: tR = 8.86 min, AP 98%.
HRMS-ESI: m/z calcd for C$_{87}$H$_{113}$O$_{19}$N$_{19}$S
(M + 2H)$^{+2}$ 880.91632, found 880.91760.

TABLE 7-continued
Characterization data for linear and cyclized products of TABLE 4 entries.
| | Capped Linear Peptide | Macrocyclization Product |
|---|---|---|
| 10 | Linear peptides Sequence: FVE$^{Me}$G$^{Me}$Y$^{Me}$F$^{Me}$GRAWT$^{Me}$FPCG (SEQ ID NO: 10) | |
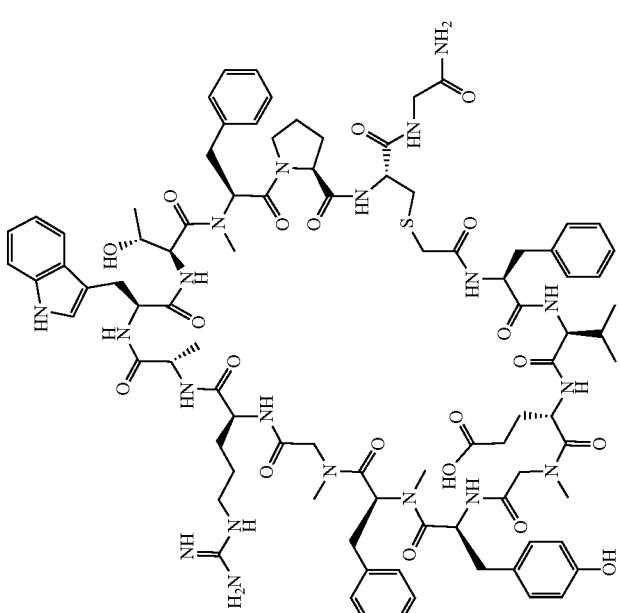

TABLE 7-continued

Characterization data for linear and cyclized products of TABLE 4 entries.

| | Capped Linear Peptide | Macrocyclization Product |
|---|---|---|
| 11 | Linear peptides Sequence: FVE$^{Me}$GY$^{Me}$F$^{Me}$GRAYWT$^{Me}$FPCG (SEQ ID NO: 11)<br>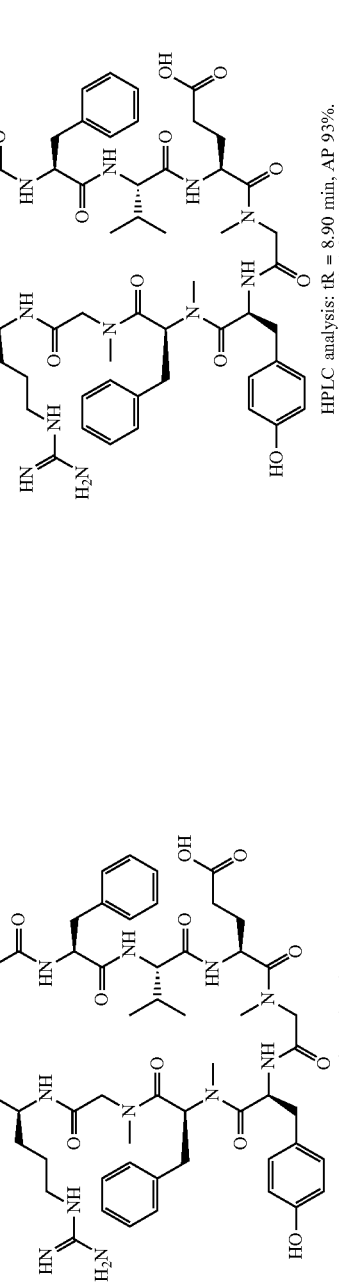<br>X: OSO$_2$PhO—(CH$_2$)$_3$N$_3$<br>HPLC analysis: tR = 13.83 min, AP 11% | 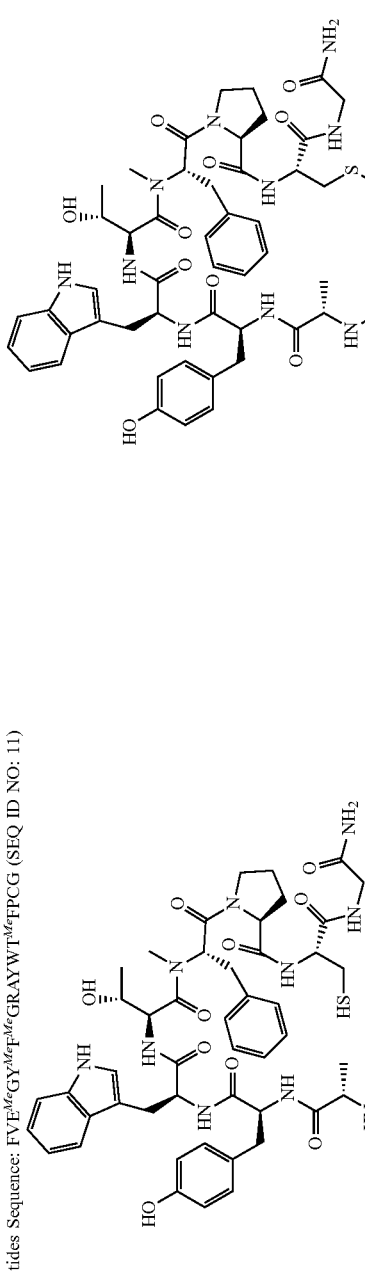<br>HPLC analysis: tR = 8.90 min, AP 93%.<br>HRMS-ESI: m/z calcd for C$_{99}$H$_{127}$O$_{22}$N$_{21}$S (M + 2H)$^{+2}$ 997.96654, found 997.96859. |

TABLE 7-continued

Characterization data for linear and cyclized products of TABLE 4 entries.

| | Capped Linear Peptide | Macrocyclization Product |
|---|---|---|
| 12 | Linear peptides Sequence: FVE$^{Me}$GY$^{Me}$F$^{Me}$GRAWT$^{Me}$FPCG (SEQ ID NO: 10)<br><br>X: OSO$_2$PhO—(CH$_2$)$_3$N$_3$<br>HPLC analysis: tR = 13.22 min, AP 8%. | HPLC analysis: tR = 8.28 min, AP 95%.<br>HRMS-ESI: m/z calcd for C$_{103}$H$_{133}$O$_{24}$N$_{23}$S (M + 2H)$^{+2}$ 1054.98800, found 1054.98914. |

TABLE 8

Characterization data for linear and cyclized products of TABLE 5 entries.

| Capped Linear Peptide | Macrocyclization Product |
|---|---|
| Linear peptides Sequence: $^{Me}$GY$^{Me}$fPDapG (SEQ ID NO: 13)<br>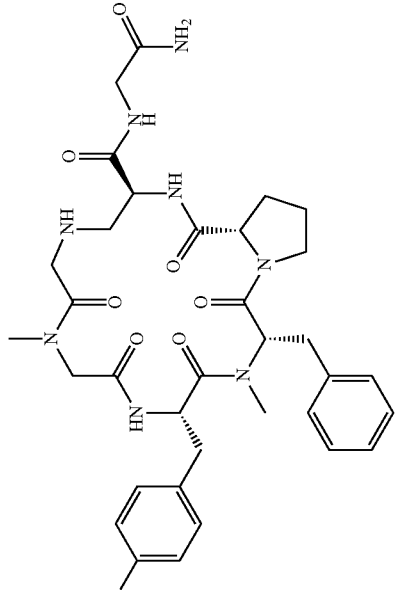<br>X: Cl; HPLC analysis: tR = 4.22 min, AP 82%.<br>X: OSO$_2$PhO—(CH$_2$)$_3$N$_3$; HPLC analysis: tR = 7.98 min, AP 72%. | 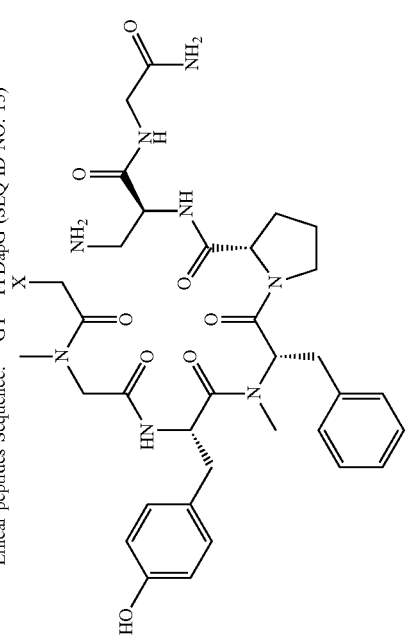<br>HPLC analysis: tR = 4.57 min, AP 96%<br>HRMS-ESI: m/z calcd for C$_{34}$H$_{44}$O$_8$N$_8$<br>(M + H)$^+$ 693.33549, found 693.33405. |
| 1 | |

TABLE 8-continued

Characterization data for linear and cyclized products of TABLE 5 entries.

| | Capped Linear Peptide | Macrocyclization Product |
|---|---|---|
| 2 | Linear peptides Sequence: $^{Me}F^{Me}GY^{Me}FPDapG$ (SEQ ID NO: 14)<br><br>X: Cl; HPLC analysis: tR = 7.16 min, AP 51%.<br>X: OSO$_2$PhO—(CH$_2$)$_3$N$_3$; HPLC analysis: tR = 12.22 min, AP 63%. | HPLC analysis: tR = 6.64 min, AP 93%.<br>HRMS-ESI: m/z calcd for C$_{44}$H$_{55}$O$_9$N$_9$<br>(M + H)$^+$ 854.41955, found 854.41742. |

TABLE 8-continued

Characterization data for linear and cyclized products of TABLE 5 entries.

| | Capped Linear Peptide | Macrocyclization Product |
|---|---|---|

Linear peptides Sequence: K(Alloc)$^{Me}$F$^{Me}$GY$^{Me}$FPDapG (SEQ ID NO: 15)

3

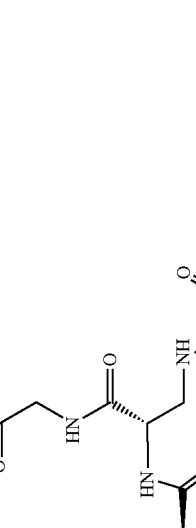

X: Cl; HPLC analysis: tR = 8.48 min, AP 5%.
X: OSO$_2$PhO—(CH$_2$)$_3$N$_3$; HPLC analysis: tR = 13.53 min, AP 4%.

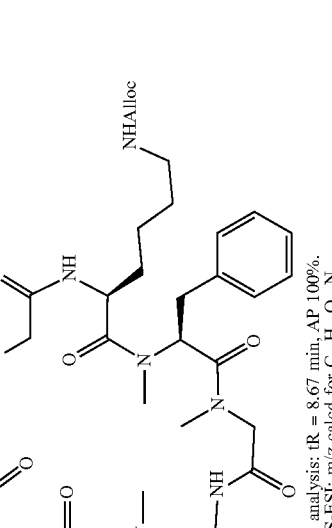

HPLC analysis: tR = 8.67 min, AP 100%.
HRMS-ESI: m/z calcd for C$_{54}$H$_{71}$O$_{12}$N$_{11}$ (M + H)$^+$ 1066.53564, found 1066.53516.

TABLE 8-continued

Characterization data for linear and cyclized products of TABLE 5 entries.

| | Capped Linear Peptide | Macrocyclization Product |
|---|---|---|
| 4 | Linear peptides Sequence: GK(Alloc)$^{Me}$F$^{Me}$GY$^{Me}$FPDapG (SEQ ID NO: 16)<br>X: Cl; HPLC analysis: tR = 7.74 min, AP 8%.<br>X: OSO$_2$PhO—(CH$_2$)$_3$N$_3$; HPLC analysis: tR = 12.88 min, AP 5%. | HPLC analysis: tR = 8.65 min, AP 100%.<br>HRMS-ESI: m/z calcd for C$_{56}$H$_{74}$O$_{13}$N$_{12}$ (M + H)$^+$ 1123.55711, found 1123.55554. |

TABLE 8-continued

Characterization data for linear and cyclized products of TABLE 5 entries.

| Capped Linear Peptide | Macrocyclization Product |
| --- | --- |

Linear peptides Sequence: SGK(Alloc)<sup>Me</sup>F<sup>Me</sup>p<sup>Me</sup>GY<sup>Me</sup>FPDapG (SEQ ID NO: 17)

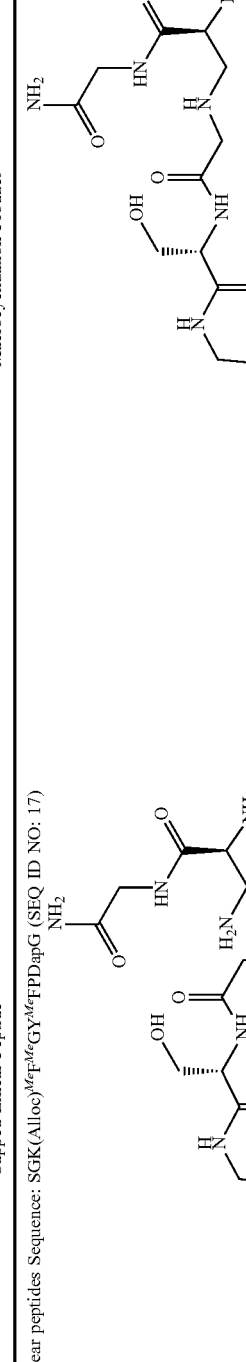

HPLC analysis: tR = 8.18 min, AP 86%.
HRMS-ESI: m/z calcd for C<sub>59</sub>H<sub>79</sub>O<sub>15</sub>N<sub>13</sub> (M + H)<sup>+</sup> 1210.58913, found 1210.58862.

5

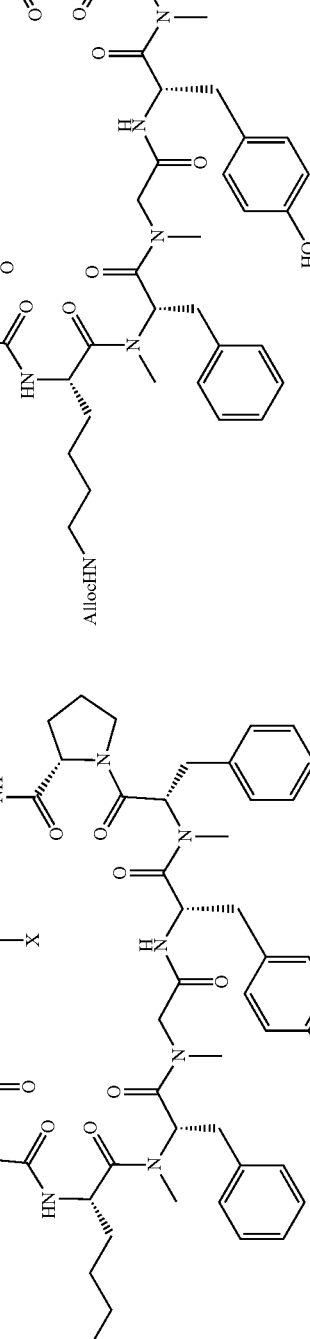

X: Cl; HPLC analysis: tR = 6.48 min, AP 7%.
X: OSO<sub>2</sub>PhO—(CH<sub>2</sub>)<sub>3</sub>N<sub>3</sub>; HPLC analysis: tR = 11.13 min, AP 5%.

TABLE 8-continued

Characterization data for linear and cyclized products of TABLE 5 entries.

| Capped Linear Peptide | Macrocyclization Product |
|---|---|

Linear peptides Sequence: VSGK(Alloc)$^{Me}$F$^{Me}$GY$^{Me}$FPDapG (SEQ ID NO: 18)

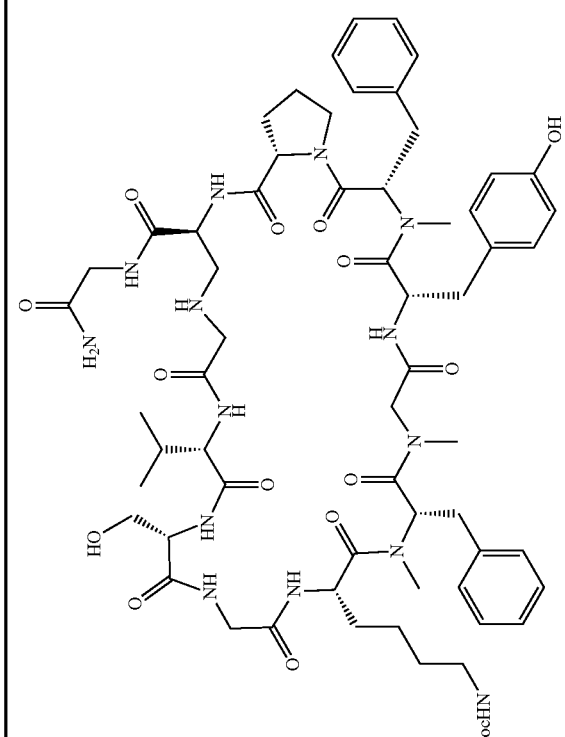

6

X: Cl; HPLC analysis: tR = 8.04 min, AP 6%.
X: OSO$_2$PhO—(CH$_2$)$_3$-N$_3$; HPLC analysis: tR = 12.67 min, AP 6%.

HPLC analysis: tR = 8.82 min, AP 76%.
HRMS-ESI: m/z calcd for C$_{64}$H$_{88}$O$_{16}$N$_{14}$ (M + H)$^+$ 1309.65755, found 1309.65723.

TABLE 8-continued

Characterization data for linear and cyclized products of TABLE 5 entries.

| | Capped Linear Peptide | Macrocyclization Product |
|---|---|---|
| 7 | Linear peptides Sequence: $^{Me}$ADVSGK(Alloc)$^{Me}$p$^{Me}$GY$^{Me}$FPDapG (SEQ ID NO: 19)<br><br>X: Cl; HPLC analysis: tR = 6.73 min, AP 8%.<br>X: OSO$_2$PhO—(CH$_2$)$_3$N$_3$; HPLC analysis: tR = 10.78 min, AP 8%. | HPLC analysis: tR = 6.87 min, AP 55%.<br>HRMS-ESI: m/z calcd for C$_{72}$H$_{100}$O$_{20}$N$_{16}$ (M + H)$^+$ 1509.73726, found 1509.73621. |

TABLE 8-continued

Characterization data for linear and cyclized products of TABLE 5 entries.

| | Capped Linear Peptide | Macrocyclization Product |
|---|---|---|
| 8 | Linear peptides Sequence: dW$^{Me}$AYYSGK(Alloc)$^{Me}$F$^{Me}$GY$^{Me}$FPDapG (SEQ ID NO: 62) | |

HPLC analysis: tR = 11.12 min, AP 68%.
HRMS-ESI: m/z calcd for $C_{88}H_{114}O_{20}N_{18}$ (M + H)$^{+}$ 1744.86078, found 1744.85339

X: Cl; HPLC analysis: tR = 11.11 min, AP 16%.
X: OSO$_2$PhO—(CH$_2$)$_3$N$_3$; HPLC analysis: tR = 14.79 min, AP 16%.

TABLE 8-continued

Characterization data for linear and cyclized products of TABLE 5 entries.

| Capped Linear Peptide | Macrocyclization Product |
|---|---|

Linear peptides Sequence: dW$^{Me}$ADVSGR$^{Me}$pMeGY$^{Me}$FPDapG (SEQ ID NO: 63)

9

Macrocyclization Product:
HPLC analysis: tR = 6.99 min, AP 59%.
HRMS-ESI: m/z calcd for C$_{79}$H$_{106}$O$_{19}$N$_{20}$
(M + 2H)$^{+2}$ 820.40443, found 820.40290

Capped Linear Peptide:
X: Cl; HPLC analysis: tR = 6.62 min, AP 23%.
X: OSO$_2$PhO—(CH$_2$)$_3$N$_3$; HPLC analysis: tR = 10.66 min, AP 18%.

TABLE 8-continued

Characterization data for linear and cyclized products of TABLE 5 entries.

| Linear peptides | Sequence: F^Me AYVSGK(Alloc)^Me F^Me GY^Me FPDapG (SEQ ID NO: 20) | |
|---|---|---|
| | Capped Linear Peptide | Macrocyclization Product |
| 10 | | |

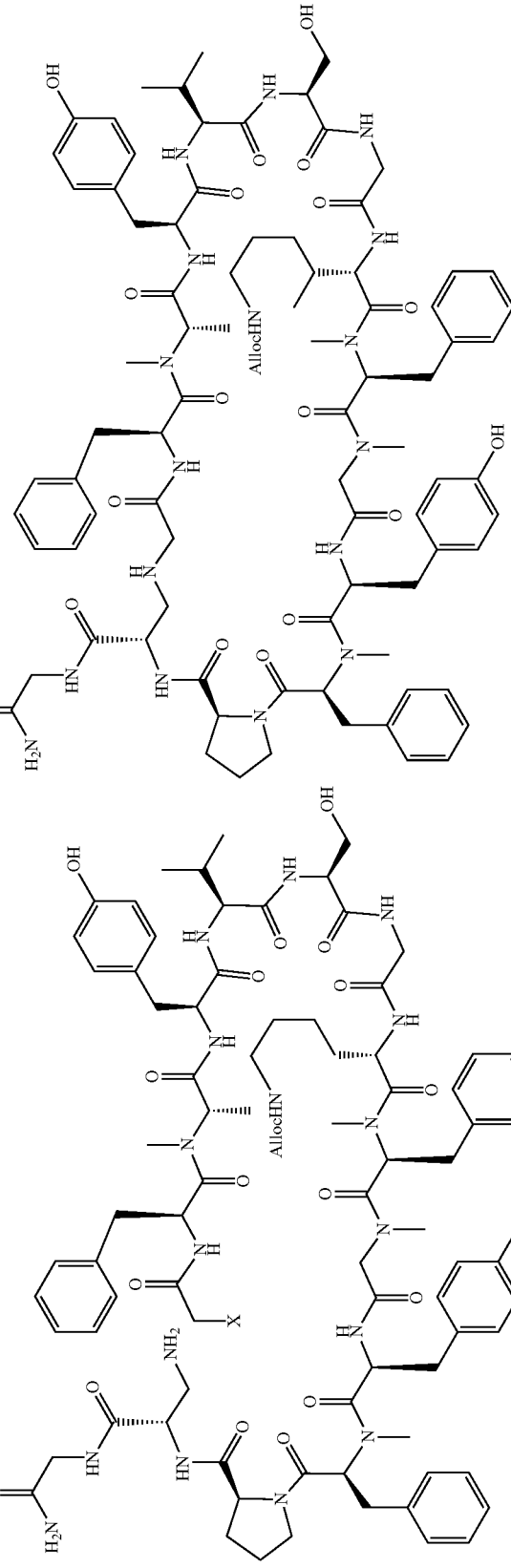

X: Cl; HPLC analysis: tR = 10.53 min, AP 5%.
X: OSO$_2$PhO—(CH$_2$)$_3$N$_3$; HPLC analysis: tR = 14.34 min, AP 4%.

HPLC analysis: tR = 11.38 min, AP 76%.
HRMS-ESI: m/z calcd for C$_{86}$H$_{113}$O$_{20}$N$_{17}$ (M + 2H)$^{+2}$ 852.92467, found 852.92456

TABLE 8-continued

Characterization data for linear and cyclized products of TABLE 5 entries.

| | Capped Linear Peptide | Macrocyclization Product |
|---|---|---|
| 11 | Linear peptides Sequence: F^Me AYVSGR^Me F^Me GY^Me FPDapG (SEQ ID NO: 21)

X: Cl; HPLC analysis: tR = 8.14 min, AP 9%.
X: OSO₂PhO—(CH₂)₃N₃; HPLC analysis: tR = 12.16 min, AP 7%. | Exact Mass: 1647.8198
HPLC analysis: tR = 8.07 min, AP 100%.
HRMS-ESI: m/z calcd for C₈₂H₁₀₉O₁₈N₁₉ (M + 2H)⁺² 824.91718, found 824.91604 |

TABLE 8-continued

Characterization data for linear and cyclized products of TABLE 5 entries.

| Capped Linear Peptide | Macrocyclization Product |
|---|---|
| 12 | |

Linear peptidesSequence: FP$^{Me}$AYVSGK(Alloc)$^{Me}$F$^{Me}$GY$^{Me}$FPDapG (SEQ ID NO: 22)

Macrocyclization Product:
HPLC analysis: tR = 11.17 min, AP 100%.
HRMS-ESI: m/z calcd for C$_{82}$H$_{109}$O$_{18}$N$_{19}$
(M + 2H)$^{+2}$ 824.91718, found 824.91604

Capped Linear Peptide:
X: Cl; HPLC analysis: tR = 8.83 min, AP 1%.
X: OSO$_2$PhO—(CH$_2$)$_3$N$_3$; HPLC analysis: tR = 14.63 min, AP 0.7%.

TABLE 8-continued

Characterization data for linear and cyclized products of TABLE 5 entries.

| Capped Linear Peptide | Macrocyclization Product |
|---|---|
| Linear peptides Sequence: F$^{Me}$GP$^{Me}$AYVSGK(Alloc)$^{Me}$F$^{Me}$GY$^{Me}$FPDapG (SEQ ID NO: 23) | |
| 13 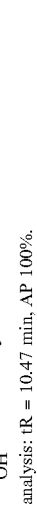<br>X: Cl; HPLC analysis: tR = 10.42 min, AP 1%.<br>X: OSO$_2$PhO—(CH$_2$)$_3$-N$_3$; HPLC analysis: tR = 14.29 min, AP 0.8%. | 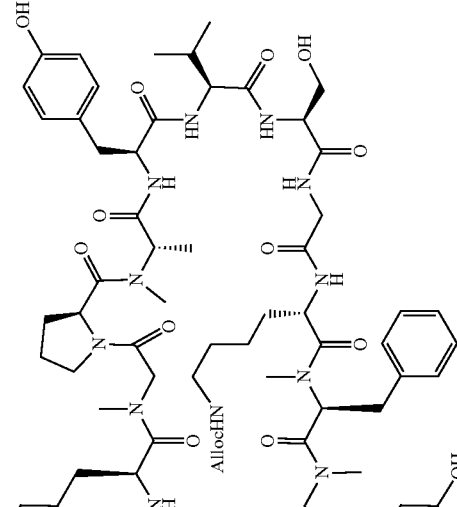<br>HPLC analysis: tR = 10.47 min, AP 100%.<br>HRMS-ESI: m/z calcd for C$_{94}$H$_{125}$O$_{22}$N$_{19}$ (M + 2H)$^{+2}$ 936.96233, found 936.97034 |

TABLE 8-continued

Characterization data for linear and cyclized products of TABLE 5 entries.

| | Capped Linear Peptide | Macrocyclization Product |
|---|---|---|
| 14 | Linear peptides Sequence: FL$^{Me}$GP$^{Me}$AYVSGK(Alloc)$^{Me}$F$^{Me}$GY$^{Me}$FPDapG (SEQ ID NO: 24) | |

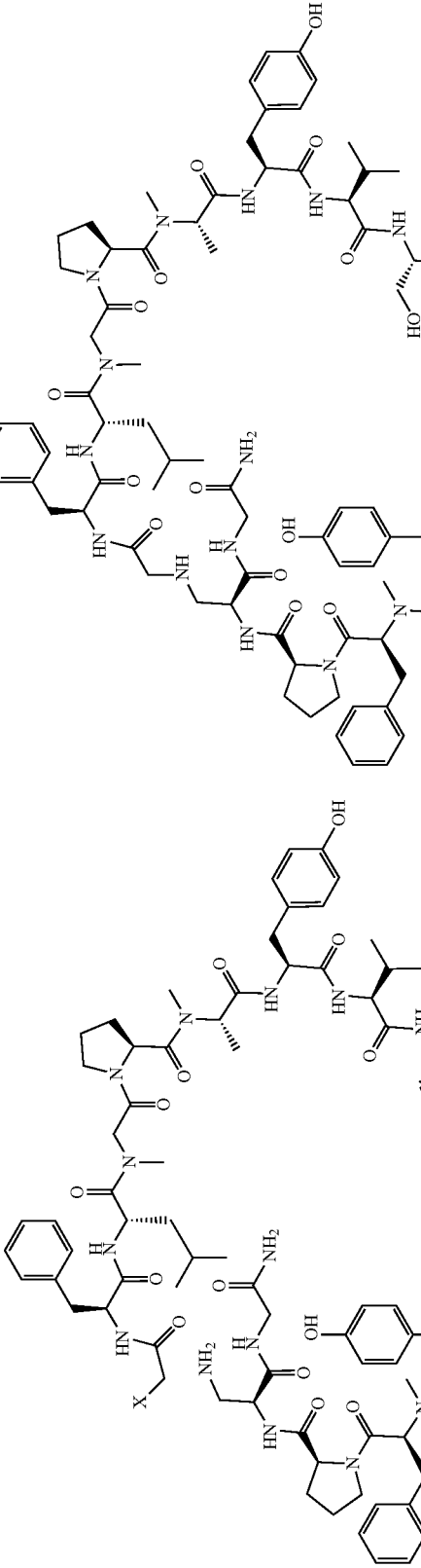

Capped Linear Peptide:
X: Cl; HPLC analysis: tR = 11.80 min, AP 1%.
X: OSO$_2$PhO—(CH$_2$)$_3$-N$_3$; HPLC analysis: tR = 13.76 min, AP 0.7%.

Macrocyclization Product:
HPLC analysis: tR = 11.43 min, AP 100%.
HRMS-ESI: m/z calcd for C$_{94}$H$_{125}$O$_{22}$N$_{19}$ (M + 2H)$^{+2}$ 993.51164, found 993.51166

TABLE 8-continued

Characterization data for linear and cyclized products of TABLE 5 entries.

| Capped Linear Peptide | Macrocyclization Product |
|---|---|

Linear peptides Sequence: FYL$^{Me}$GP$^{Me}$AYVSGK(Alloc)$^{Me}$F$^{Me}$GY$^{Me}$FPDapG (SEQ ID NO: 25)

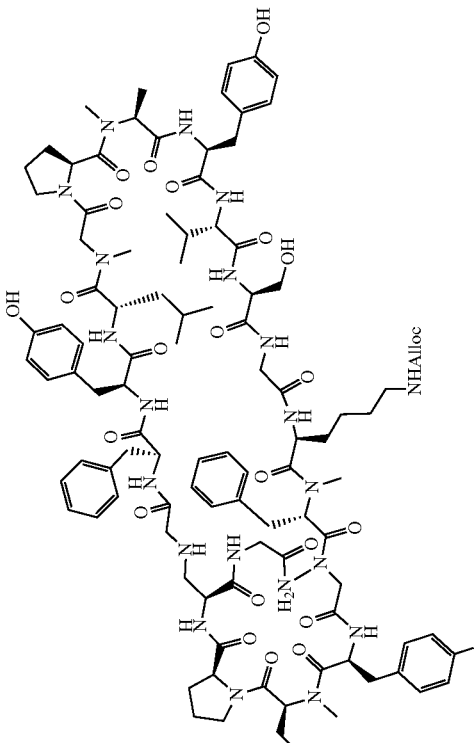

15

X: Cl; HPLC analysis: tR = 11.93 min AP 1%.
X: OSO$_2$PhO—(CH$_2$)$_3$-N$_3$; HPLC analysis: tR = 13.71 min, AP 0.9%.

HPLC analysis: tR = 11.49 min, AP 100%.
HRMS-ESI: m/z calcd for C$_{109}$H$_{145}$O$_{25}$N$_{21}$
(M + 2H)$^{+2}$ 1075.04330, found 1075.04367

What is claimed:
1. A compound of formula (I)
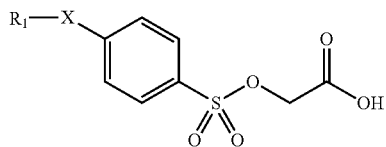
(I)
wherein
X is a bond, —O—, —C(O)—, —OC(O)—, —NH—, —N(C$_{1-6}$alkyl)-, —N(aryl)-, —NH—C(O)—, —N(C$_{1-6}$alkyl)C(O)—, or —N(aryl)C(O)—; and
R$^1$ is
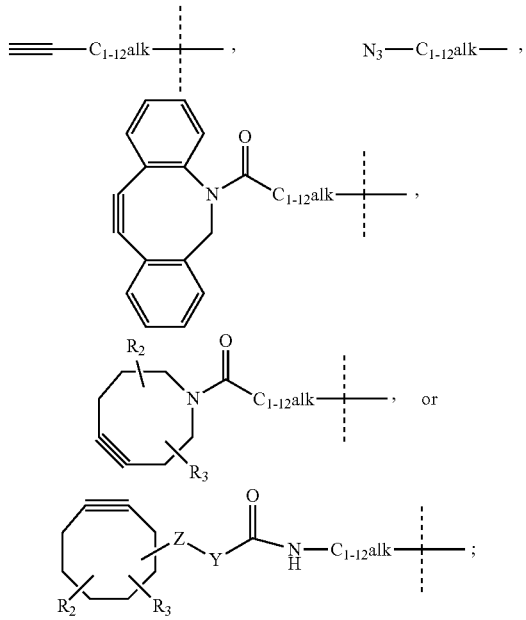
wherein R$_2$ and R$_3$ are each independently H, halo, C$_{1-6}$alkyl, or OC$_{1-6}$alkyl;
Z is C$_{1-6}$alk or —O—C$_{1-6}$alk-; and
Y is a bond or arylene.
2. The compound according to claim 1 that is
Cap A
Cap B
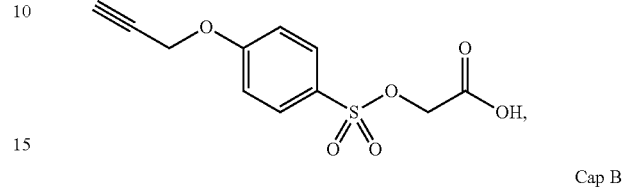
Cap C
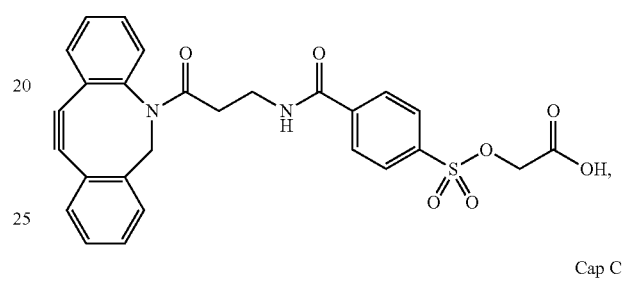
or
Cap D
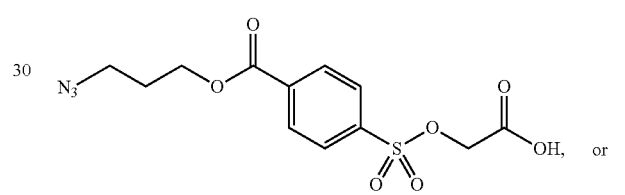
* * * * *

UNITED STATES PATENT AND TRADEMARK OFFICE
CERTIFICATE OF CORRECTION

PATENT NO. : 12,018,097 B2
APPLICATION NO. : 17/943532
DATED : June 25, 2024
INVENTOR(S) : Gardner S. Creech et al.

Page 1 of 1

It is certified that error appears in the above-identified patent and that said Letters Patent is hereby corrected as shown below:

On the Title Page

Item (72), In Inventors,

Under Column no. 1, Line no. 5, delete "H" insert --H.--

In Other Publications,

Under Column no. 2, Line no. 6, delete "InternationalEdition" insert --International Edition--

Under Column no. 2, Line no. 18, delete "InternationalEdition" insert --International Edition--

Under Column no. 2, Line no. 21, delete "NMethylation" insert --N-Methylation--

In the Claims

Under Column no. 169, Claim 1, Line no. 16, delete "$R^1$" insert --$R_1$--

Signed and Sealed this
Twelfth Day of November, 2024

Katherine Kelly Vidal
*Director of the United States Patent and Trademark Office*

SEQUENCE LISTING

```
Sequence total quantity: 63
SEQ ID NO: 1                moltype = AA  length = 6
FEATURE                     Location/Qualifiers
REGION                      1..6
                            note = Description of Artificial Sequence: Synthetic peptide
MOD_RES                     4
                            note = N-methylated Gly
source                      1..6
                            mol_type = protein
                            organism = synthetic construct
SEQUENCE: 1
FVEGCG                                                                          6

SEQ ID NO: 2                moltype = AA  length = 7
FEATURE                     Location/Qualifiers
REGION                      1..7
                            note = Description of Artificial Sequence: Synthetic peptide
MOD_RES                     4
                            note = N-methylated Gly
source                      1..7
                            mol_type = protein
                            organism = synthetic construct
SEQUENCE: 2
FVEGYCG                                                                         7

SEQ ID NO: 3                moltype = AA  length = 8
FEATURE                     Location/Qualifiers
REGION                      1..8
                            note = Description of Artificial Sequence: Synthetic peptide
MOD_RES                     4
                            note = N-methylated Gly
MOD_RES                     6
                            note = N-methylated Phe
source                      1..8
                            mol_type = protein
                            organism = synthetic construct
SEQUENCE: 3
FVEGYFCG                                                                        8

SEQ ID NO: 4                moltype = AA  length = 9
FEATURE                     Location/Qualifiers
REGION                      1..9
                            note = Description of Artificial Sequence: Synthetic peptide
MOD_RES                     4
                            note = N-methylated Gly
MOD_RES                     6
                            note = N-methylated Phe
MOD_RES                     7
                            note = N-methylated Gly
source                      1..9
                            mol_type = protein
                            organism = synthetic construct
SEQUENCE: 4
FVEGYFGCG                                                                       9

SEQ ID NO: 5                moltype = AA  length = 10
FEATURE                     Location/Qualifiers
REGION                      1..10
                            note = Description of Artificial Sequence: Synthetic peptide
MOD_RES                     4
                            note = N-methylated Gly
MOD_RES                     6
                            note = N-methylated Phe
MOD_RES                     7
                            note = N-methylated Gly
source                      1..10
                            mol_type = protein
                            organism = synthetic construct
SEQUENCE: 5
FVEGYFGTCG                                                                      10

SEQ ID NO: 6                moltype = AA  length = 11
FEATURE                     Location/Qualifiers
REGION                      1..11
                            note = Description of Artificial Sequence: Synthetic peptide
MOD_RES                     4
                            note = N-methylated Gly
MOD_RES                     6
```

|   |   |   |
|---|---|---|
| MOD_RES | 7 | |
| | note = N-methylated Phe | |
| MOD_RES | 9 | |
| | note = N-methylated Gly | |
| | note = N-methylated Phe | |
| source | 1..11 | |
| | mol_type = protein | |
| | organism = synthetic construct | |
| SEQUENCE: 6 | | |
| FVEGYFGTFC G | | 11 |
| | | |
| SEQ ID NO: 7 | moltype = AA  length = 12 | |
| FEATURE | Location/Qualifiers | |
| REGION | 1..12 | |
| | note = Description of Artificial Sequence: Synthetic peptide | |
| MOD_RES | 4 | |
| | note = N-methylated Gly | |
| MOD_RES | 6 | |
| | note = N-methylated Phe | |
| MOD_RES | 7 | |
| | note = N-methylated Gly | |
| MOD_RES | 9 | |
| | note = N-methylated Phe | |
| source | 1..12 | |
| | mol_type = protein | |
| | organism = synthetic construct | |
| SEQUENCE: 7 | | |
| FVEGYFGTFP CG | | 12 |
| | | |
| SEQ ID NO: 8 | moltype = AA  length = 13 | |
| FEATURE | Location/Qualifiers | |
| REGION | 1..13 | |
| | note = Description of Artificial Sequence: Synthetic peptide | |
| MOD_RES | 4 | |
| | note = N-methylated Gly | |
| MOD_RES | 6 | |
| | note = N-methylated Phe | |
| MOD_RES | 7 | |
| | note = N-methylated Gly | |
| MOD_RES | 10 | |
| | note = N-methylated Phe | |
| source | 1..13 | |
| | mol_type = protein | |
| | organism = synthetic construct | |
| SEQUENCE: 8 | | |
| FVEGYFGWTF PCG | | 13 |
| | | |
| SEQ ID NO: 9 | moltype = AA  length = 14 | |
| FEATURE | Location/Qualifiers | |
| REGION | 1..14 | |
| | note = Description of Artificial Sequence: Synthetic peptide | |
| MOD_RES | 4 | |
| | note = N-methylated Gly | |
| MOD_RES | 6 | |
| | note = N-methylated Phe | |
| MOD_RES | 7 | |
| | note = N-methylated Gly | |
| MOD_RES | 11 | |
| | note = N-methylated Phe | |
| source | 1..14 | |
| | mol_type = protein | |
| | organism = synthetic construct | |
| SEQUENCE: 9 | | |
| FVEGYFGRWT FPCG | | 14 |
| | | |
| SEQ ID NO: 10 | moltype = AA  length = 15 | |
| FEATURE | Location/Qualifiers | |
| REGION | 1..15 | |
| | note = Description of Artificial Sequence: Synthetic peptide | |
| MOD_RES | 4 | |
| | note = N-methylated Gly | |
| MOD_RES | 6 | |
| | note = N-methylated Phe | |
| MOD_RES | 7 | |
| | note = N-methylated Gly | |
| MOD_RES | 12 | |
| | note = N-methylated Phe | |
| source | 1..15 | |
| | mol_type = protein | |

```
                          organism = synthetic construct
SEQUENCE: 10
FVEGYFGRAW TFPCG                                                           15

SEQ ID NO: 11             moltype = AA   length = 16
FEATURE                   Location/Qualifiers
REGION                    1..16
                          note = Description of Artificial Sequence: Synthetic peptide
MOD_RES                   4
                          note = N-methylated Gly
MOD_RES                   6
                          note = N-methylated Phe
MOD_RES                   7
                          note = N-methylated Gly
MOD_RES                   13
                          note = N-methylated Phe
source                    1..16
                          mol_type = protein
                          organism = synthetic construct
SEQUENCE: 11
FVEGYFGRAY WTFPCG                                                          16

SEQ ID NO: 12             moltype = AA   length = 17
FEATURE                   Location/Qualifiers
REGION                    1..17
                          note = Description of Artificial Sequence: Synthetic peptide
MOD_RES                   4
                          note = N-methylated Gly
MOD_RES                   6
                          note = N-methylated Phe
MOD_RES                   7
                          note = N-methylated Gly
MOD_RES                   14
                          note = N-methylated Phe
source                    1..17
                          mol_type = protein
                          organism = synthetic construct
SEQUENCE: 12
FVEGYFGRNA YWTFPCG                                                         17

SEQ ID NO: 13             moltype = AA   length = 6
FEATURE                   Location/Qualifiers
REGION                    1..6
                          note = Description of Artificial Sequence: Synthetic peptide
MOD_RES                   1
                          note = N-methylated Gly
MOD_RES                   3
                          note = N-methylated Phe
MOD_RES                   5
                          note = 2,3-diaminopropionic acid
source                    1..6
                          mol_type = protein
                          organism = synthetic construct
SEQUENCE: 13
GYFPXG                                                                     6

SEQ ID NO: 14             moltype = AA   length = 7
FEATURE                   Location/Qualifiers
REGION                    1..7
                          note = Description of Artificial Sequence: Synthetic peptide
MOD_RES                   1
                          note = N-methylated Phe
MOD_RES                   2
                          note = N-methylated Gly
MOD_RES                   4
                          note = N-methylated Phe
MOD_RES                   6
                          note = 2,3-diaminopropionic acid
source                    1..7
                          mol_type = protein
                          organism = synthetic construct
SEQUENCE: 14
FGYFPXG                                                                    7

SEQ ID NO: 15             moltype = AA   length = 8
FEATURE                   Location/Qualifiers
REGION                    1..8
                          note = Description of Artificial Sequence: Synthetic peptide
MOD_RES                   1
```

|            |                                           |
|------------|-------------------------------------------|
| MOD_RES    | note = Allyloxycarbonyl Lys               |
|            | 2                                         |
| MOD_RES    | note = N-methylated Phe                   |
|            | 3                                         |
| MOD_RES    | note = N-methylated Gly                   |
|            | 5                                         |
| MOD_RES    | note = N-methylated Phe                   |
|            | 7                                         |
|            | note = 2,3-diaminopropionic acid          |
| source     | 1..8                                      |
|            | mol_type = protein                        |
|            | organism = synthetic construct            |

SEQUENCE: 15
KFGYFPXG                                                                        8

| SEQ ID NO: 16 | moltype = AA   length = 9                                      |
|---------------|----------------------------------------------------------------|
| FEATURE       | Location/Qualifiers                                            |
| REGION        | 1..9                                                           |
|               | note = Description of Artificial Sequence: Synthetic peptide   |
| MOD_RES       | 2                                                              |
|               | note = Allyloxycarbonyl Lys                                    |
| MOD_RES       | 3                                                              |
|               | note = N-methylated Phe                                        |
| MOD_RES       | 4                                                              |
|               | note = N-methylated Gly                                        |
| MOD_RES       | 6                                                              |
|               | note = N-methylated Phe                                        |
| MOD_RES       | 8                                                              |
|               | note = 2,3-diaminopropionic acid                               |
| source        | 1..9                                                           |
|               | mol_type = protein                                             |
|               | organism = synthetic construct                                 |

SEQUENCE: 16
GKFGYFPXG                                                                       9

| SEQ ID NO: 17 | moltype = AA   length = 10                                     |
|---------------|----------------------------------------------------------------|
| FEATURE       | Location/Qualifiers                                            |
| REGION        | 1..10                                                          |
|               | note = Description of Artificial Sequence: Synthetic peptide   |
| MOD_RES       | 3                                                              |
|               | note = Allyloxycarbonyl Lys                                    |
| MOD_RES       | 4                                                              |
|               | note = N-methylated Phe                                        |
| MOD_RES       | 5                                                              |
|               | note = N-methylated Gly                                        |
| MOD_RES       | 7                                                              |
|               | note = N-methylated Phe                                        |
| MOD_RES       | 9                                                              |
|               | note = 2,3-diaminopropionic acid                               |
| source        | 1..10                                                          |
|               | mol_type = protein                                             |
|               | organism = synthetic construct                                 |

SEQUENCE: 17
SGKFGYFPXG                                                                      10

| SEQ ID NO: 18 | moltype = AA   length = 11                                     |
|---------------|----------------------------------------------------------------|
| FEATURE       | Location/Qualifiers                                            |
| REGION        | 1..11                                                          |
|               | note = Description of Artificial Sequence: Synthetic peptide   |
| MOD_RES       | 4                                                              |
|               | note = Allyloxycarbonyl Lys                                    |
| MOD_RES       | 5                                                              |
|               | note = N-methylated Phe                                        |
| MOD_RES       | 6                                                              |
|               | note = N-methylated Gly                                        |
| MOD_RES       | 8                                                              |
|               | note = N-methylated Phe                                        |
| MOD_RES       | 10                                                             |
|               | note = 2,3-diaminopropionic acid                               |
| source        | 1..11                                                          |
|               | mol_type = protein                                             |
|               | organism = synthetic construct                                 |

SEQUENCE: 18
VSGKFGYFPX G                                                                    11

| SEQ ID NO: 19 | moltype = AA   length = 13                                     |
|---------------|----------------------------------------------------------------|
| FEATURE       | Location/Qualifiers                                            |
| REGION        | 1..13                                                          |
|               | note = Description of Artificial Sequence: Synthetic peptide   |

```
MOD_RES          1
                 note = N-methylated Ala
MOD_RES          6
                 note = Allyloxycarbonyl Lys
MOD_RES          7
                 note = N-methylated Phe
MOD_RES          8
                 note = N-methylated Gly
MOD_RES          10
                 note = N-methylated Phe
MOD_RES          12
                 note = 2,3-diaminopropionic acid
source           1..13
                 mol_type = protein
                 organism = synthetic construct
SEQUENCE: 19
ADVSGKFGYF PXG                                                                13

SEQ ID NO: 20    moltype = AA  length = 14
FEATURE          Location/Qualifiers
REGION           1..14
                 note = Description of Artificial Sequence: Synthetic peptide
MOD_RES          2
                 note = N-methylated Ala
MOD_RES          7
                 note = Allyloxycarbonyl Lys
MOD_RES          8
                 note = N-methylated Phe
MOD_RES          9
                 note = N-methylated Gly
MOD_RES          11
                 note = N-methylated Phe
MOD_RES          13
                 note = 2,3-diaminopropionic acid
source           1..14
                 mol_type = protein
                 organism = synthetic construct
SEQUENCE: 20
FAYVSGKFGY FPXG                                                               14

SEQ ID NO: 21    moltype = AA  length = 14
FEATURE          Location/Qualifiers
REGION           1..14
                 note = Description of Artificial Sequence: Synthetic peptide
MOD_RES          2
                 note = N-methylated Ala
MOD_RES          8
                 note = N-methylated Phe
MOD_RES          9
                 note = N-methylated Gly
MOD_RES          11
                 note = N-methylated Phe
MOD_RES          13
                 note = 2,3-diaminopropionic acid
source           1..14
                 mol_type = protein
                 organism = synthetic construct
SEQUENCE: 21
FAYVSGRFGY FPXG                                                               14

SEQ ID NO: 22    moltype = AA  length = 15
FEATURE          Location/Qualifiers
REGION           1..15
                 note = Description of Artificial Sequence: Synthetic peptide
MOD_RES          3
                 note = N-methylated Ala
MOD_RES          8
                 note = Allyloxycarbonyl Lys
MOD_RES          9
                 note = N-methylated Phe
MOD_RES          10
                 note = N-methylated Gly
MOD_RES          12
                 note = N-methylated Phe
MOD_RES          14
                 note = 2,3-diaminopropionic acid
source           1..15
                 mol_type = protein
                 organism = synthetic construct
```

```
SEQUENCE: 22
FPAYVSGKFG YFPXG                                                                 15

SEQ ID NO: 23           moltype = AA  length = 16
FEATURE                 Location/Qualifiers
REGION                  1..16
                        note = Description of Artificial Sequence: Synthetic peptide
MOD_RES                 2
                        note = N-methylated Gly
MOD_RES                 4
                        note = N-methylated Ala
MOD_RES                 9
                        note = Allyloxycarbonyl Lys
MOD_RES                 10
                        note = N-methylated Phe
MOD_RES                 11
                        note = N-methylated Gly
MOD_RES                 13
                        note = N-methylated Phe
MOD_RES                 15
                        note = 2,3-diaminopropionic acid
source                  1..16
                        mol_type = protein
                        organism = synthetic construct
SEQUENCE: 23
FGPAYVSGKF GYFPXG                                                                16

SEQ ID NO: 24           moltype = AA  length = 17
FEATURE                 Location/Qualifiers
REGION                  1..17
                        note = Description of Artificial Sequence: Synthetic peptide
MOD_RES                 3
                        note = N-methylated Gly
MOD_RES                 5
                        note = N-methylated Ala
MOD_RES                 10
                        note = Allyloxycarbonyl Lys
MOD_RES                 11
                        note = N-methylated Phe
MOD_RES                 12
                        note = N-methylated Gly
MOD_RES                 14
                        note = N-methylated Phe
MOD_RES                 16
                        note = 2,3-diaminopropionic acid
source                  1..17
                        mol_type = protein
                        organism = synthetic construct
SEQUENCE: 24
FLGPAYVSGK FGYFPXG                                                               17

SEQ ID NO: 25           moltype = AA  length = 18
FEATURE                 Location/Qualifiers
REGION                  1..18
                        note = Description of Artificial Sequence: Synthetic peptide
MOD_RES                 4
                        note = N-methylated Gly
MOD_RES                 6
                        note = N-methylated Ala
MOD_RES                 11
                        note = Allyloxycarbonyl Lys
MOD_RES                 12
                        note = N-methylated Phe
MOD_RES                 13
                        note = N-methylated Gly
MOD_RES                 15
                        note = N-methylated Phe
MOD_RES                 17
                        note = 2,3-diaminopropionic acid
source                  1..18
                        mol_type = protein
                        organism = synthetic construct
SEQUENCE: 25
FYLGPAYVSG KFGYFPXG                                                              18

SEQ ID NO: 26           moltype = AA  length = 6
FEATURE                 Location/Qualifiers
source                  1..6
                        mol_type = protein
```

```
                        organism = Synthetic construct
SITE                    1
                        note = D-Tryptophan
MOD_RES                 2
                        note = N-methylated alanine
SEQUENCE: 26
WADVCG                                                                        6

SEQ ID NO: 27           moltype = AA   length = 7
FEATURE                 Location/Qualifiers
source                  1..7
                        mol_type = protein
                        organism = Synthetic construct
SITE                    1
                        note = D-Tryptophan
MOD_RES                 2
                        note = N-methylated alanine
MOD_RES                 5
                        note = N-methylated serine
SEQUENCE: 27
WADVSCG                                                                       7

SEQ ID NO: 28           moltype = AA   length = 8
FEATURE                 Location/Qualifiers
source                  1..8
                        mol_type = protein
                        organism = Synthetic construct
SITE                    1
                        note = D-Tryptophan
MOD_RES                 2
                        note = N-methylated alanine
MOD_RES                 5
                        note = N-methylated serine
SEQUENCE: 28
WADVSGCG                                                                      8

SEQ ID NO: 29           moltype = AA   length = 9
FEATURE                 Location/Qualifiers
source                  1..9
                        mol_type = protein
                        organism = Synthetic construct
SITE                    1
                        note = D-Tryptophan
MOD_RES                 2
                        note = N-methylated alanine
MOD_RES                 5
                        note = N-methylated serine
SEQUENCE: 29
WADVSGRCG                                                                     9

SEQ ID NO: 30           moltype = AA   length = 10
FEATURE                 Location/Qualifiers
source                  1..10
                        mol_type = protein
                        organism = Synthetic construct
SITE                    1
                        note = D-Tryptophan
MOD_RES                 2
                        note = N-methylated alanine
MOD_RES                 5
                        note = N-methylated serine
MOD_RES                 8
                        note = N-methylated Phenylalanine
SEQUENCE: 30
WADVSGRFCG                                                                   10

SEQ ID NO: 31           moltype = AA   length = 11
FEATURE                 Location/Qualifiers
source                  1..11
                        mol_type = protein
                        organism = Synthetic construct
SITE                    1
                        note = D-Tryptophan
MOD_RES                 2
                        note = N-methylated alanine
MOD_RES                 5
                        note = N-methylated serine
MOD_RES                 8
                        note = N-methylated Phenylalanine
```

| | | |
|---|---|---|
| MOD_RES | 9 | |
| | note = N-methylated glycine | |
| SEQUENCE: 31 | | |
| WADVSGRFGC G | | 11 |
| | | |
| SEQ ID NO: 32 | moltype = AA  length = 12 | |
| FEATURE | Location/Qualifiers | |
| source | 1..12 | |
| | mol_type = protein | |
| | organism = Synthetic construct | |
| SITE | 1 | |
| | note = D-Tryptophan | |
| MOD_RES | 2 | |
| | note = N-methylated alanine | |
| MOD_RES | 5 | |
| | note = N-methylated serine | |
| MOD_RES | 8 | |
| | note = N-methylated Phenylalanine | |
| MOD_RES | 9 | |
| | note = N-methylated glycine | |
| SEQUENCE: 32 | | |
| WADVSGRFGY CG | | 12 |
| | | |
| SEQ ID NO: 33 | moltype = AA  length = 13 | |
| FEATURE | Location/Qualifiers | |
| source | 1..13 | |
| | mol_type = protein | |
| | organism = Synthetic construct | |
| SITE | 1 | |
| | note = D-Tryptophan | |
| MOD_RES | 2 | |
| | note = N-methylated alanine | |
| MOD_RES | 5 | |
| | note = N-methylated serine | |
| MOD_RES | 8 | |
| | note = N-methylated Phenylalanine | |
| MOD_RES | 11 | |
| | note = N-methylated Phenylalanine | |
| MOD_RES | 9 | |
| | note = N-methylated glycine | |
| SEQUENCE: 33 | | |
| WADVSGRFGY FCG | | 13 |
| | | |
| SEQ ID NO: 34 | moltype = AA  length = 14 | |
| FEATURE | Location/Qualifiers | |
| source | 1..14 | |
| | mol_type = protein | |
| | organism = Synthetic construct | |
| SITE | 1 | |
| | note = D-Tryptophan | |
| MOD_RES | 2 | |
| | note = N-methylated alanine | |
| MOD_RES | 5 | |
| | note = N-methylated serine | |
| MOD_RES | 8 | |
| | note = N-methylated Phenylalanine | |
| MOD_RES | 11 | |
| | note = N-methylated Phenylalanine | |
| MOD_RES | 9 | |
| | note = N-methylated glycine | |
| SEQUENCE: 34 | | |
| WADVSGRFGY FPCG | | 14 |
| | | |
| SEQ ID NO: 35 | moltype = AA  length = 14 | |
| FEATURE | Location/Qualifiers | |
| source | 1..14 | |
| | mol_type = protein | |
| | organism = Synthetic construct | |
| SITE | 1 | |
| | note = D-Tryptophan | |
| MOD_RES | 5 | |
| | note = N-methylated serine | |
| MOD_RES | 8 | |
| | note = N-methylated Phenylalanine | |
| MOD_RES | 11 | |
| | note = N-methylated Phenylalanine | |
| MOD_RES | 9 | |
| | note = N-methylated glycine | |
| SEQUENCE: 35 | | |

```
WCDVSGRFGY FPCG                                                        14

SEQ ID NO: 36          moltype = AA  length = 15
FEATURE                Location/Qualifiers
source                 1..15
                       mol_type = protein
                       organism = Synthetic construct
SITE                   1
                       note = D-Tryptophan
MOD_RES                3
                       note = N-methylated alanine
MOD_RES                6
                       note = N-methylated serine
MOD_RES                9
                       note = N-methylated Phenylalanine
MOD_RES                12
                       note = N-methylated Phenylalanine
MOD_RES                10
                       note = N-methylated glycine
SEQUENCE: 36
WPADVSGRFG YFPCG                                                       15

SEQ ID NO: 37          moltype = AA  length = 16
FEATURE                Location/Qualifiers
source                 1..16
                       mol_type = protein
                       organism = Synthetic construct
SITE                   1
                       note = D-Tryptophan
MOD_RES                4
                       note = N-methylated alanine
MOD_RES                7
                       note = N-methylated serine
MOD_RES                10
                       note = N-methylated Phenylalanine
MOD_RES                13
                       note = N-methylated Phenylalanine
MOD_RES                11
                       note = N-methylated glycine
SEQUENCE: 37
WDPADVSGRF GYFPCG                                                      16

SEQ ID NO: 38          moltype = AA  length = 17
FEATURE                Location/Qualifiers
source                 1..17
                       mol_type = protein
                       organism = Synthetic construct
SITE                   1
                       note = D-Tryptophan
MOD_RES                5
                       note = N-methylated alanine
MOD_RES                8
                       note = N-methylated serine
MOD_RES                11
                       note = N-methylated Phenylalanine
MOD_RES                14
                       note = N-methylated Phenylalanine
MOD_RES                12
                       note = N-methylated glycine
SEQUENCE: 38
WGDPADVSGR FGYFPCG                                                     17

SEQ ID NO: 39          moltype = AA  length = 18
FEATURE                Location/Qualifiers
source                 1..18
                       mol_type = protein
                       organism = Synthetic construct
SITE                   1
                       note = D-Tryptophan
MOD_RES                6
                       note = N-methylated alanine
MOD_RES                2
                       note = N-methylated serine
MOD_RES                9
                       note = N-methylated serine
MOD_RES                12
                       note = N-methylated Phenylalanine
MOD_RES                15
                       note = N-methylated Phenylalanine
```

| | | |
|---|---|---|
| MOD_RES | 13 | |
| | note = N-methylated glycine | |
| SEQUENCE: 39 | | |
| WSGDPADVSG RFGYFPCG | | 18 |
| | | |
| SEQ ID NO: 40 | moltype = AA  length = 19 | |
| FEATURE | Location/Qualifiers | |
| source | 1..19 | |
| | mol_type = protein | |
| | organism = Synthetic construct | |
| SITE | 1 | |
| | note = D-Tryptophan | |
| MOD_RES | 7 | |
| | note = N-methylated alanine | |
| MOD_RES | 3 | |
| | note = N-methylated serine | |
| MOD_RES | 10 | |
| | note = N-methylated serine | |
| MOD_RES | 13 | |
| | note = N-methylated Phenylalanine | |
| MOD_RES | 16 | |
| | note = N-methylated Phenylalanine | |
| MOD_RES | 14 | |
| | note = N-methylated glycine | |
| SEQUENCE: 40 | | |
| WDSGDPADVS GRFGYFPCG | | 19 |
| | | |
| SEQ ID NO: 41 | moltype = AA  length = 20 | |
| FEATURE | Location/Qualifiers | |
| source | 1..20 | |
| | mol_type = protein | |
| | organism = Synthetic construct | |
| SITE | 1 | |
| | note = D-Tryptophan | |
| MOD_RES | 8 | |
| | note = N-methylated alanine | |
| MOD_RES | 4 | |
| | note = N-methylated serine | |
| MOD_RES | 11 | |
| | note = N-methylated serine | |
| MOD_RES | 14 | |
| | note = N-methylated Phenylalanine | |
| MOD_RES | 17 | |
| | note = N-methylated Phenylalanine | |
| MOD_RES | 15 | |
| | note = N-methylated glycine | |
| SEQUENCE: 41 | | |
| WYDSGDPADV SGRFGYFPCG | | 20 |
| | | |
| SEQ ID NO: 42 | moltype = AA  length = 21 | |
| FEATURE | Location/Qualifiers | |
| source | 1..21 | |
| | mol_type = protein | |
| | organism = Synthetic construct | |
| SITE | 1 | |
| | note = D-Tryptophan | |
| MOD_RES | 2 | |
| | note = N-methylated alanine | |
| MOD_RES | 9 | |
| | note = N-methylated alanine | |
| MOD_RES | 5 | |
| | note = N-methylated serine | |
| MOD_RES | 12 | |
| | note = N-methylated serine | |
| MOD_RES | 15 | |
| | note = N-methylated Phenylalanine | |
| MOD_RES | 18 | |
| | note = N-methylated Phenylalanine | |
| MOD_RES | 16 | |
| | note = N-methylated glycine | |
| SEQUENCE: 42 | | |
| WAYDSGDPAD VSGRFGYFPC G | | 21 |
| | | |
| SEQ ID NO: 43 | moltype = AA  length = 14 | |
| FEATURE | Location/Qualifiers | |
| source | 1..14 | |
| | mol_type = protein | |
| | organism = Synthetic construct | |
| SITE | 1 | |

```
                    note = D-Tryptophan
MOD_RES             2
                    note = N-methylated alanine
MOD_RES             8
                    note = N-methylated Phenylalanine
MOD_RES             11
                    note = N-methylated Phenylalanine
MOD_RES             9
                    note = N-methylated glycine
MOD_RES             7
                    note = Allyloxycarbonyl Lys
MOD_RES             13
                    note = 2,3-diaminopropionic acid
SEQUENCE: 43
WAYVSGKFGY FPXG                                                         14

SEQ ID NO: 44       moltype = AA  length = 14
FEATURE             Location/Qualifiers
source              1..14
                    mol_type = protein
                    organism = Synthetic construct
SITE                1
                    note = D-Tryptophan
MOD_RES             2
                    note = N-methylated alanine
MOD_RES             8
                    note = N-methylated Phenylalanine
MOD_RES             11
                    note = N-methylated Phenylalanine
MOD_RES             9
                    note = N-methylated glycine
MOD_RES             13
                    note = 2,3-diaminopropionic acid
SEQUENCE: 44
WADVSGRFGY FPXG                                                         14

SEQ ID NO: 45       moltype = AA  length = 6
FEATURE             Location/Qualifiers
source              1..6
                    mol_type = protein
                    organism = Synthetic construct
SITE                1
                    note = D-Tryptophan
MOD_RES             2
                    note = N-methylated alanine
SEQUENCE: 45
WADVCG                                                                  6

SEQ ID NO: 46       moltype = AA  length = 7
FEATURE             Location/Qualifiers
source              1..7
                    mol_type = protein
                    organism = Synthetic construct
SITE                1
                    note = D-Tryptophan
MOD_RES             2
                    note = N-methylated alanine
MOD_RES             5
                    note = N-methylated serine
SEQUENCE: 46
WADVSCG                                                                 7

SEQ ID NO: 47       moltype = AA  length = 8
FEATURE             Location/Qualifiers
source              1..8
                    mol_type = protein
                    organism = Synthetic construct
SITE                1
                    note = D-Tryptophan
MOD_RES             2
                    note = N-methylated alanine
MOD_RES             5
                    note = N-methylated serine
SEQUENCE: 47
WADVSGCG                                                                8

SEQ ID NO: 48       moltype = AA  length = 9
FEATURE             Location/Qualifiers
source              1..9
```

```
                    mol_type = protein
                    organism = Synthetic construct
SITE                1
                    note = D-Tryptophan
MOD_RES             2
                    note = N-methylated alanine
MOD_RES             5
                    note = N-methylated serine
SEQUENCE: 48
WADVSGRCG                                                                 9

SEQ ID NO: 49       moltype = AA  length = 10
FEATURE             Location/Qualifiers
source              1..10
                    mol_type = protein
                    organism = Synthetic construct
SITE                1
                    note = D-Tryptophan
MOD_RES             2
                    note = N-methylated alanine
MOD_RES             5
                    note = N-methylated serine
MOD_RES             8
                    note = N-methylated Phenylalanine
SEQUENCE: 49
WADVSGRFCG                                                               10

SEQ ID NO: 50       moltype = AA  length = 11
FEATURE             Location/Qualifiers
source              1..11
                    mol_type = protein
                    organism = Synthetic construct
SITE                1
                    note = D-Tryptophan
MOD_RES             2
                    note = N-methylated alanine
MOD_RES             5
                    note = N-methylated serine
MOD_RES             8
                    note = N-methylated Phenylalanine
MOD_RES             9
                    note = N-methylated glycine
SEQUENCE: 50
WADVSGRFGC G                                                             11

SEQ ID NO: 51       moltype = AA  length = 12
FEATURE             Location/Qualifiers
source              1..12
                    mol_type = protein
                    organism = Synthetic construct
SITE                1
                    note = D-Tryptophan
MOD_RES             2
                    note = N-methylated alanine
MOD_RES             5
                    note = N-methylated serine
MOD_RES             8
                    note = N-methylated Phenylalanine
MOD_RES             9
                    note = N-methylated glycine
SEQUENCE: 51
WADVSGRFGY CG                                                            12

SEQ ID NO: 52       moltype = AA  length = 13
FEATURE             Location/Qualifiers
source              1..13
                    mol_type = protein
                    organism = Synthetic construct
SITE                1
                    note = D-Tryptophan
MOD_RES             2
                    note = N-methylated alanine
MOD_RES             5
                    note = N-methylated serine
MOD_RES             8
                    note = N-methylated Phenylalanine
MOD_RES             11
                    note = N-methylated Phenylalanine
MOD_RES             9
```

|  |  |  |
|---|---|---|
| | note = N-methylated glycine | |
| SEQUENCE: 52 | | |
| WADVSGRFGY FCG | | 13 |
| | | |
| SEQ ID NO: 53 | moltype = AA   length = 14 | |
| FEATURE | Location/Qualifiers | |
| source | 1..14 | |
| | mol_type = protein | |
| | organism = Synthetic construct | |
| SITE | 1 | |
| | note = D-Tryptophan | |
| MOD_RES | 2 | |
| | note = N-methylated alanine | |
| MOD_RES | 5 | |
| | note = N-methylated serine | |
| MOD_RES | 8 | |
| | note = N-methylated Phenylalanine | |
| MOD_RES | 11 | |
| | note = N-methylated Phenylalanine | |
| MOD_RES | 9 | |
| | note = N-methylated glycine | |
| SEQUENCE: 53 | | |
| WADVSGRFGY FPCG | | 14 |
| | | |
| SEQ ID NO: 54 | moltype = AA   length = 14 | |
| FEATURE | Location/Qualifiers | |
| source | 1..14 | |
| | mol_type = protein | |
| | organism = Synthetic construct | |
| SITE | 1 | |
| | note = D-Tryptophan | |
| MOD_RES | 5 | |
| | note = N-methylated serine | |
| MOD_RES | 8 | |
| | note = N-methylated Phenylalanine | |
| MOD_RES | 11 | |
| | note = N-methylated Phenylalanine | |
| MOD_RES | 9 | |
| | note = N-methylated glycine | |
| SEQUENCE: 54 | | |
| WCDVSGRFGY FPCG | | 14 |
| | | |
| SEQ ID NO: 55 | moltype = AA   length = 15 | |
| FEATURE | Location/Qualifiers | |
| source | 1..15 | |
| | mol_type = protein | |
| | organism = Synthetic construct | |
| SITE | 1 | |
| | note = D-Tryptophan | |
| MOD_RES | 3 | |
| | note = N-methylated alanine | |
| MOD_RES | 6 | |
| | note = N-methylated serine | |
| MOD_RES | 9 | |
| | note = N-methylated Phenylalanine | |
| MOD_RES | 12 | |
| | note = N-methylated Phenylalanine | |
| MOD_RES | 10 | |
| | note = N-methylated glycine | |
| SEQUENCE: 55 | | |
| WPADVSGRFG YFPCG | | 15 |
| | | |
| SEQ ID NO: 56 | moltype = AA   length = 16 | |
| FEATURE | Location/Qualifiers | |
| source | 1..16 | |
| | mol_type = protein | |
| | organism = Synthetic construct | |
| SITE | 1 | |
| | note = D-Tryptophan | |
| MOD_RES | 4 | |
| | note = N-methylated alanine | |
| MOD_RES | 7 | |
| | note = N-methylated serine | |
| MOD_RES | 10 | |
| | note = N-methylated Phenylalanine | |
| MOD_RES | 13 | |
| | note = N-methylated Phenylalanine | |
| MOD_RES | 11 | |
| | note = N-methylated glycine | |

```
SEQUENCE: 56
WDPADVSGRF GYFPCG                                                     16

SEQ ID NO: 57           moltype = AA  length = 17
FEATURE                 Location/Qualifiers
source                  1..17
                        mol_type = protein
                        organism = Synthetic construct
SITE                    1
                        note = D-Tryptophan
MOD_RES                 5
                        note = N-methylated alanine
MOD_RES                 8
                        note = N-methylated serine
MOD_RES                 11
                        note = N-methylated Phenylalanine
MOD_RES                 14
                        note = N-methylated Phenylalanine
MOD_RES                 12
                        note = N-methylated glycine
SEQUENCE: 57
WGDPADVSGR FGYFPCG                                                    17

SEQ ID NO: 58           moltype = AA  length = 18
FEATURE                 Location/Qualifiers
source                  1..18
                        mol_type = protein
                        organism = Synthetic construct
SITE                    1
                        note = D-Tryptophan
MOD_RES                 6
                        note = N-methylated alanine
MOD_RES                 2
                        note = N-methylated serine
MOD_RES                 9
                        note = N-methylated serine
MOD_RES                 12
                        note = N-methylated Phenylalanine
MOD_RES                 15
                        note = N-methylated Phenylalanine
MOD_RES                 13
                        note = N-methylated glycine
SEQUENCE: 58
WSGDPADVSG RFGYFPCG                                                   18

SEQ ID NO: 59           moltype = AA  length = 19
FEATURE                 Location/Qualifiers
source                  1..19
                        mol_type = protein
                        organism = Synthetic construct
SITE                    1
                        note = D-Tryptophan
MOD_RES                 7
                        note = N-methylated alanine
MOD_RES                 3
                        note = N-methylated serine
MOD_RES                 10
                        note = N-methylated serine
MOD_RES                 13
                        note = N-methylated Phenylalanine
MOD_RES                 16
                        note = N-methylated Phenylalanine
MOD_RES                 14
                        note = N-methylated glycine
SEQUENCE: 59
WDSGDPADVS GRFGYFPCG                                                  19

SEQ ID NO: 60           moltype = AA  length = 20
FEATURE                 Location/Qualifiers
source                  1..20
                        mol_type = protein
                        organism = Synthetic construct
SITE                    1
                        note = D-Tryptophan
MOD_RES                 8
                        note = N-methylated alanine
MOD_RES                 4
                        note = N-methylated serine
MOD_RES                 11
```

```
                         note = N-methylated serine
MOD_RES                  14
                         note = N-methylated Phenylalanine
MOD_RES                  17
                         note = N-methylated Phenylalanine
MOD_RES                  15
                         note = N-methylated glycine
SEQUENCE: 60
WYDSGDPADV SGRFGYFPCG                                                  20

SEQ ID NO: 61            moltype = AA  length = 21
FEATURE                  Location/Qualifiers
source                   1..21
                         mol_type = protein
                         organism = Synthetic construct
SITE                     1
                         note = D-Tryptophan
MOD_RES                  2
                         note = N-methylated alanine
MOD_RES                  9
                         note = N-methylated alanine
MOD_RES                  5
                         note = N-methylated serine
MOD_RES                  12
                         note = N-methylated serine
MOD_RES                  15
                         note = N-methylated Phenylalanine
MOD_RES                  18
                         note = N-methylated Phenylalanine
MOD_RES                  16
                         note = N-methylated glycine
SEQUENCE: 61
WAYDSGDPAD VSGRFGYFPC G                                                21

SEQ ID NO: 62            moltype = AA  length = 14
FEATURE                  Location/Qualifiers
source                   1..14
                         mol_type = protein
                         organism = Synthetic construct
SITE                     1
                         note = D-Tryptophan
MOD_RES                  2
                         note = N-methylated alanine
MOD_RES                  8
                         note = N-methylated Phenylalanine
MOD_RES                  11
                         note = N-methylated Phenylalanine
MOD_RES                  9
                         note = N-methylated glycine
MOD_RES                  7
                         note = Allyloxycarbonyl Lys
MOD_RES                  13
                         note = 2,3-diaminopropionic acid
SEQUENCE: 62
WAYVSGKFGY FPXG                                                        14

SEQ ID NO: 63            moltype = AA  length = 14
FEATURE                  Location/Qualifiers
source                   1..14
                         mol_type = protein
                         organism = Synthetic construct
SITE                     1
                         note = D-Tryptophan
MOD_RES                  2
                         note = N-methylated alanine
MOD_RES                  8
                         note = N-methylated Phenylalanine
MOD_RES                  11
                         note = N-methylated Phenylalanine
MOD_RES                  9
                         note = N-methylated glycine
MOD_RES                  13
                         note = 2,3-diaminopropionic acid
SEQUENCE: 63
WADVSGRFGY FPXG                                                        14
```